United States Patent
Plavec et al.

(10) Patent No.: US 7,266,458 B2
(45) Date of Patent: Sep. 4, 2007

(54) BIOMAP ANALYSIS

(75) Inventors: Ivan Plavec, Sunnyvale, CA (US);
Ellen L. Berg, Palo Alto, CA (US);
Eugene C. Butcher, Portola Valley, CA (US)

(73) Assignee: Bioseek, Inc., Burlingame, CA (US)

( * ) Notice: Subject to any disclaimer, the term of this patent is extended or adjusted under 35 U.S.C. 154(b) by 486 days.

(21) Appl. No.: 10/236,558

(22) Filed: Sep. 5, 2002

(65) Prior Publication Data
US 2003/0138811 A1 Jul. 24, 2003

Related U.S. Application Data

(63) Continuation-in-part of application No. PCT/US01/07190, filed on Mar. 6, 2001.

(60) Provisional application No. 60/195,672, filed on Apr. 7, 2000, provisional application No. 60/186,976, filed on Mar. 6, 2000.

(51) Int. Cl.
*G06F 19/00* (2006.01)
(52) U.S. Cl. .................................................. 702/19
(58) Field of Classification Search .................. None
See application file for complete search history.

(56) References Cited

U.S. PATENT DOCUMENTS

| | | | |
|---|---|---|---|
| 4,568,649 A | 2/1986 | Bertoglio-Matte | |
| 5,569,588 A | 10/1996 | Ashby et al. | |
| 5,631,153 A | 5/1997 | Capecchi et al. | |
| 5,777,888 A | 7/1998 | Rine et al. | |
| 5,994,076 A | 11/1999 | Chenchik et al. | |
| 6,004,755 A | 12/1999 | Wang | |
| 6,013,437 A | 1/2000 | Luria et al. | |
| 6,146,830 A | 11/2000 | Friend et al. | |

FOREIGN PATENT DOCUMENTS

WO WO95/06132 3/1995
WO WO96/23075 8/1996

OTHER PUBLICATIONS

Giuliani et al. (Journal of Cell Science (1999).*
Collins et al. (FASEB (1995) vol. 9, pp. 899-909).*
Altschul et al. (Feb. 1994), "Issues in Searching Molecular Sequence Databases." *Nature Genetics*, vol. 6:119-129.
Blackstock et al. (Mar. 1999), "Proteomics: Quantitative and Physical Mapping of Cellular Proteins." *TIBTECH*, vol. 17:121-127.
Hatzimanikatis et al. (1999), "Proteomics: Theoretical and Experimental Considerations." *Biotechnol.*, vol. 15:312-318.
Mullner et al. (1998), "Proteomics: A New Way for Drug Target Discovery." *Arzneim-Forsch.*, vol. 48(1):93-95.
Nellen et al. (Nov. 1993), "What Makes an mRNA Anti-Sense-Itive?" *TIBS*, vol. 18:419-423.
Heller et al., Discovery and Analysis of Inflammatory Disease-Related Genes Using cDNA Microarrays, Proc. Natl. Acad. Sci., (1997), 94: 2150-2155.
May et al., Effects of Protein Tyrosine Kinase Inhibitors on Cytokine-Induced Adhesion Molecule Expression by Human Umbilical Vein Endothelial Cells, Brit. Journal, of Pharmacology, 1996, 118(7): 1761-1771.
Rice et al., Development of a Heigh Volume Screen to Identify Inhibitors of Endothelial Cell Activation, Analytical Biochem., 1996, 241(2): 254-259.
Hausner et al., The Comparative Growth Assay: Examining The Interplay of Anti-Cancer Agents With Cells Carrying Single Gene Alterations, Neoplasia, Doyma, 1999, 1(4): 356-367.

* cited by examiner

*Primary Examiner*—Lori A. Clow
(74) *Attorney, Agent, or Firm*—Bozicevic, Field & Francis LLP; Pamela J. Sherwood; Kevin Kaster

(57) ABSTRACT

The involvement of an expression product in a cell in a pathway is determined by genetically modifying the cell, incubating the cell with predetermined factors in induce a physiological state and measuring parameters affected by the pathway. Changes in the levels of the parameters as a result of the presence of the expressed product indicate that the expression product is involved with the pathway.

21 Claims, 16 Drawing Sheets

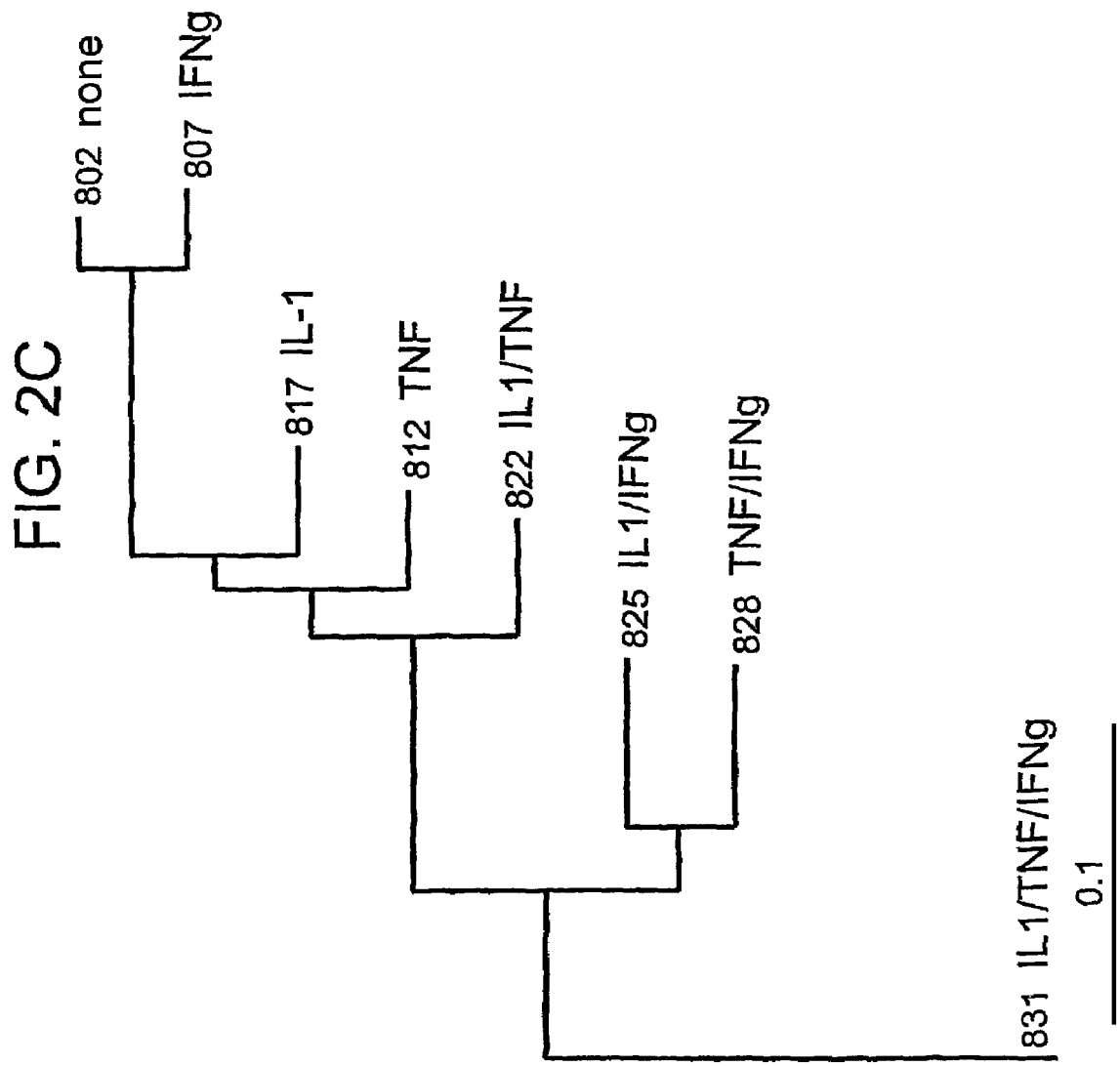

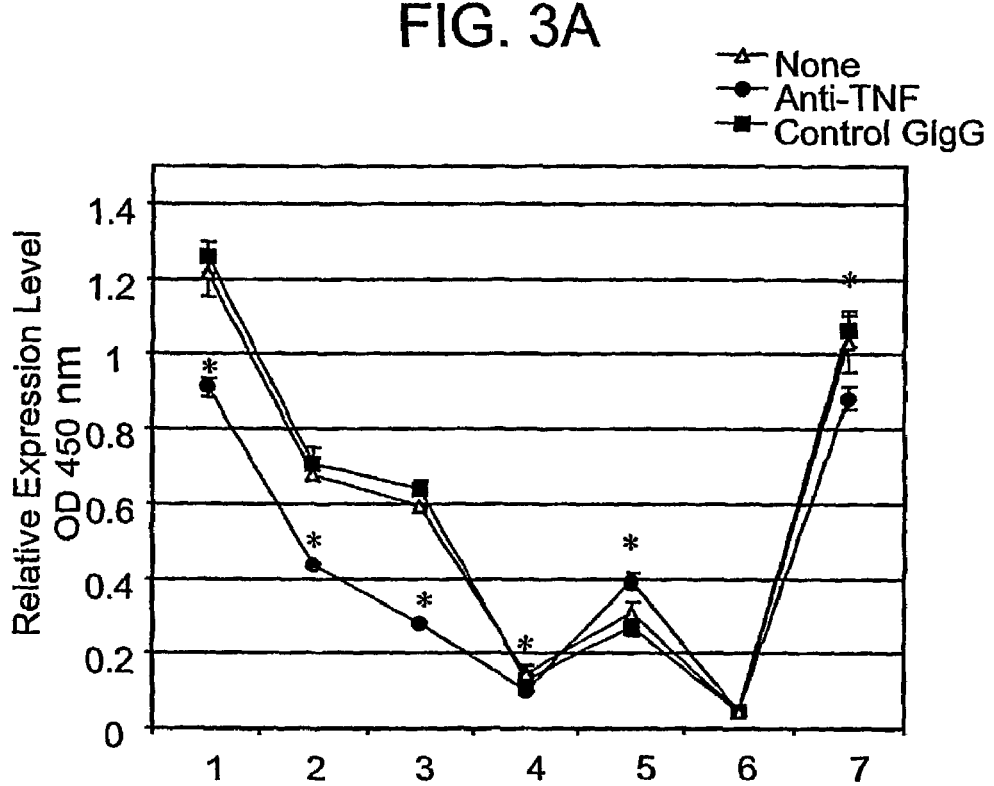
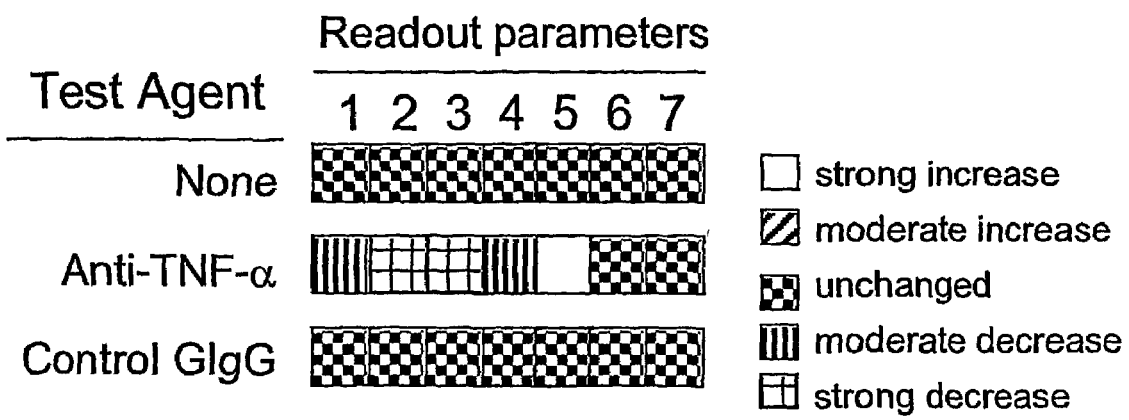

FIG. 5

Assay Combinations

| Treatment: | no cytokine | IL-1 | TNF-α | IFNg | IL-1/TNF/IFNg |
|---|---|---|---|---|---|
| Control | 1 2 3 4 5 | 1 2 3 4 5 | 1 2 3 4 5 | 1 2 3 4 5 | 1 2 3 4 5 |
| Anti-TNF-α | | | | | |
| AA861 | | | | | |
| NHGA | | | | | |

Parameters

- ☐ strong increase
- ▨ moderate increase
- ▩ unchanged
- ⊟ moderate decrease
- ⊞ strong decrease

FIG. 6

Assay Combinations

| Test agent: | no cytokine | IL-1 | *Act-anti-p55 | TNF-α |
|---|---|---|---|---|
| None | 1 2 3 4 5 | 1 2 3 4 5 | 1 2 3 4 5 | 1 2 3 4 5 |
| Anti-TNF-α | 1 2 3 4 5 | 1 2 3 4 5 | 1 2 3 4 5 | 1 2 3 4 5 |

Parameters

Legend:
- ☐ strong increase
- ▨ moderate increase
- ▦ unchanged
- ▥ moderate decrease
- ▤ strong decrease

FIG. 8

Assay Combinations

| Test gene: | no cytokine | IL-1 | TNF-α | IL-1/TNF/IFNγ |
|---|---|---|---|---|
| Control | ▦ 1234567 | ▦ 1234567 | ▦ 1234567 | ▦ 1234567 |
| Bcl-3 | ▦▨ 1234567 | ▦▨ 1234567 | ▦ 1234567 | ▦ 1234567 |

Parameters

- ☐ strong increase
- ▨ moderate increase
- ▦ unchanged
- ▥ moderate decrease
- ▦ strong decrease

FIG. 9

Assay Combinations

| Test gene: | media | Ceramide | TNF-α | Ceramide+TNF-α |
|---|---|---|---|---|
| Control | | | | |
| bcl-2 | | | | |
| bcl-xl | | | | |
| | 1 2 3 4 | 1 2 3 4 | 1 2 3 4 | 1 2 3 4 |

Parameters

- ☐ strong increase
- ▨ moderate increase
- ▦ unchanged
- ▥ moderate decrease
- ▤ strong decrease

BIOMAP ANALYSIS

This application is a continuation-in-part of application Ser. No. PCT/US01/07190, International Publication No. WO 01/67103, filed Mar. 6, 2001, and claims priority to provisional applications No. 60/186,976, filed Mar. 6, 2000 and No. 60/195,672, filed Apr. 7, 2000, the entire contents of each of which is incorporated herein by reference.

BACKGROUND

The increase in the number of potential new drug targets generated by technological advances in genomics over the past decade has fed the need for more rapid and informative methods to validate and prioritize novel targets for drug development. The efficacy of drug development, as measured by the number of clinical failures, is expected to worsen over the next 5-10 years, due in part to the relative lack of information about new targets (so-called unprecedented targets), for which compounds will enter clinical trials. The process of drug development is long and expensive, taking on average 12 years and over $500M from the discovery to FDA approval of a new chemical entity. Much of the cost of new drug development is due to failure in clinical testing. Fewer than 1 of every 9 drugs that enters clinical testing becomes approved, and thus there are relatively few new drugs, that enter the market every year. The pharmaceutical industry has addressed this lack of pipeline efficiency by increasing capacity for high-through-put screening of large libraries of chemical compounds. However, despite significant increases in high-through-put screening capacity over the last decade the numbers of newly lunched drugs has remained the same (Lehman Brothers, "The Fruits of Genomics" report, January, 2001).

The main reason for the inefficiency of the drug development process is attributed to the lack of in depth understanding of the biology of targets against which new drugs are being developed. Historically pharmaceutical companies benefited from target identification and validation efforts provided over many years by academic and government-funded laboratories. Over the past decade, however advances in genomics and other approaches have led to an overload of poorly validated potential new therapeutic targets. Due to the need to maintain growth, pharmaceutical companies are pressured to advance many targets into high throughput screening programs even when only limited biological information and rationale is available to support further development.

Several strategies have led to identification of these potential targets. Some targets have been identified based on expression profiles, e.g. highly expressed in disease tissues, or mutated in human disease; by homology to well known drug targets, e.g. G-protein coupled receptors; and/or by activity in model systems, e.g. induction of cytotoxicity or cytostasis in cancer cell lines. Given the number of potential targets that have been identified by such criteria, target prioritization has become a key activity in the drug development process. Target prioritization requires additional information on the relative biological relevance of the target. This information typically comes from studies of the function of gene targets in model systems.

Model organisms such as yeast, *C. elegans*, drosophila and zebrafish are useful systems for characterizing gene functions as they are easy to genetically modify and can be screened rapidly. However, although these models provide complex systems that allow functional characterization of genes and the ability to distinguish a variety of gene functions, the behavior of genes in these systems will not always predict their behavior in mammalian systems. Some pathways may be generally conserved, such as those involved in cholesterol synthesis, etc., however, the regulation of even these conserved pathways in mammals show important differences. Knock-out and transgenic mice have proven to be important mammalian model systems for gene function, characterization and target validation. On the negative side, generating knock-out mice is expensive and time consuming. In addition, for conventional knock-out mice that lack the targeted gene throughout their life, the functional role of a target in the adult may be masked by its role during development. While animal models of disease, including genetically modified mice as well as conventional models such as in rats, pigs and primates remain the preferred systems for biological studies because of their ability to reflect more of the complex mechanisms of the disease process, they are less useful for predicting gene function. Either technologies for testing gene function in a particular animal species are not yet available or the animal models do not sufficiently predict human disease.

Human cell lines have also been used for study of gene function, and for therapeutic drug development. However, there is mounting evidence that there are significant differences in signal transduction pathways between cell lines and primary cells, and that data from cell lines can not be extrapolated to primary cells. Therefor, even though they are frequently more difficult to culture, primary human cells are a preferred model for biological profiling of genes that are intended as targets for therapeutic drug development. Primary cells retain most of the complex intracellular regulatory networks that control biological processes in vivo, and have not been exposed to selective pressures, which shape the signal transduction pathways in immortalized cell lines. Thus, biological models that more accurately take into account the complexity of signal transduction pathways and human disease pathophysiology are better suited to address the growing need for biological characterization of newly identified drug targets.

There are many methods and technologies available for cellular profiling. These include gene array and proteomics techniques, cell imaging, flow cytometry and other new technologies. One feature of gene arrays is that many transcripts can be evaluated simultaneously. However, the monetary and time cost for chip-based screening is prohibitive for routine evaluation of large numbers of samples, and many array techniques do not detect low abundance mRNA, cannot distinguish between subtle differences in mRNA levels, and require many repeats to generate statistically significant data. In addition, the measurement of mRNA levels suffers from the substantial problem that the mRNA levels of many genes do not correlate with expression or "functionally relevant" expression of their protein products. Even in the relatively simple organism, yeast, only 50% of proteins, which showed altered levels in response to change in nutrients, had altered levels of the corresponding mRNAs. Gene array techniques also do not provide information on lipids or carbohydrates nor on the conformational state of the expressed protein, such as heterodimer or other complex formation, localization, or modifications such as phosphorylation, prenylation or carbohydrate modification.

Proteomics techniques have also been applied to cellular profiling. Some methods require technically complex analysis and comparison of high-resolution two-dimensional gels, followed by mass spectrometry. Newer methods rely on alternative separation strategies, but are still limited to the analysis of proteins within certain molecular weight ranges and/or with certain physicochemical properties. Furthermore, most techniques do not distinguish between molecules that are expressed on the cell surface and those that are intracellular. For example, the adhesion molecule P-selectin is expressed constitutively by endothelial cells, but is held in intracellular stores until released to the cell surface upon thrombin or histamine activation.

Relevant Publications

Steiner et al (2001) Toxicol. Lett 120, 369-77; Wodicka et al. (1997) Nat Biotech 15, 1359-67; Dimster-Denk et al. (1999) J Lipid Research, 40, 850-860; Matthews and Kopczynski (2001) Drug Discov. Today 6, 141-149; Xing et al. (2000) J Recept Signal Transduct Res 20, 189-210; Weinstein et al. (1997) Science 275, 343-9; Rao (2001) J Leukoc Biol 69, 3-10; Sigurdson et al. (2002) J Biomed Mater Res 59, 357-65; Guastadisegni et al. (1997) FEBS Lett 413, 314-8; Liu et al. (2002) Microcirculation 9, 13-22 (2002); Finkelstein et al. (2002) Plant Mol Biol 48, 119-31; Ideker, et al. (2001) Science 292, 929-934; Dove (1999) Nat Biotechnol 17, 233-6; Wagner (1993) Thromb Haemost 70, 105-10.

In many assays, cell-free components such as enzymes and their substrates are used for compound screening. For example, U.S. Pat. No. 4,568,649 describes ligand detection systems that employ scintillation counting. In these methods, the therapeutic utility of compounds identified in such assays is presumed from a large body of other evidence previously identifying that a particular enzyme or target may be important to a disease process.

Cell based assays include a variety of methods to measure metabolic activities of cells including: uptake of tagged molecules or metabolic precursors, receptor binding methods, incorporation of tritiated thymidine as a measure of cellular proliferation, uptake of protein or lipid biosynthesis precursors, the binding of radiolabeled or otherwise labeled ligands; assays to measure calcium flux, and a variety of techniques to measure the expression of specific genes or their gene products.

Compounds have also been screened for their ability to inhibit the expression of specific genes in gene reporter assays. For example, Ashby et al. U.S. Pat. No. 5,569,588; Rine and Ashby U.S. Pat. No. 5,777,888 describe a genome reporter matrix approach for comparing the effect of drugs on a panel of reporter genes to reveal effects of a compound on the transcription of a spectrum of genes in the genome.

Methods utilizing genetic sequence microarrays allow the detection of changes in expression patterns in response to stimulus. A few examples include U.S. Pat. No. 6,013,437; Luria et al., "Method for identifying translationally regulated genes"; U.S. Pat. No. 6,004,755, Wang, "Quantitative microarray hybridization assays"; and U.S. Pat. No. 5,994,076, Chenchik et al., "Methods of assaying differential expression". U.S. Pat. No. 6,146,830, Friend et al. "Method for determining the presence of a number of primary targets of a drug".

Proteomics techniques have potential for application to pharmaceutical drug screening. These methods require technically complex analysis and comparison of high resolution two-dimensional gels or other separation methods, often followed by mass spectrometry (for reviews see Hatzimanikatis et al. (1999) Biotechnol Prog 15(3):312-8;

Blackstock et al. (1999) Trends Biotechnol 17(3):121-7. A discussion of the uses of proteomics in drug discovery may be found in Mullner et al. (1998) Arzneimittelforschung 48(1):93-5.

Various methods have been used to determine the function of a genetic sequence. The initial effort is often performed from sequence information alone. Such techniques can reasonably determine if a new gene encodes a soluble or membrane-bound protein, a member of a known gene family such as the immunoglobulin gene family or the tetraspan gene family, or contains domains associated with particular functions (e.g. calcium binding, SH2 domains etc.). Multiple alignments against a database of known sequences are frequently calculated using an heuristic approach, as described in Altschul et al. (1994) Nat. Genet. 6:119.

Alternatively, "reverse genetics" is used to identify gene function. Techniques include the use of genetically modified cells and animals. A targeted gene may be "knocked out" by site specific recombination, introduction of anti-sense constructs or constructs encoding dominant negative mutations, and the like (see, for some examples, U.S. Pat. No. 5,631,153, Capecchi et al. for methods of creating transgenic animals; Lagna et al. (1998) Curr Top Dev Biol 36:75-98 for an overview of the use of dominant negative constructs; and Nellen et al. (1993) Trends Biochem Sci 18(11):419-23 for a review of anti-sense constructs).

Cells and animals may also be modified by the introduction of genetic function, through the introduction of functional coding sequences corresponding to the genetic sequence of interest. General techniques for the creation of transgenic animals may be found in Mouse Genetics and Transgenics: A Practical Approach (Practical Approach Series) by Ian J. Jackson (Editor), Catherine M. Abbott (Editor). While they have proven useful in many ways, however, transgenic animals frequently suffer from problems of time and expense, as well as compensatory mechanisms, redundancies, pleiotropic genetic effects, and the lethality of certain mutations.

Another approach for discovering the function of genes utilizes gene chips or microarrays. DNA sequences representing all the genes in an organism can be placed on miniature solid supports and used as hybridization substrates to quantitate the expression of all the genes represented in a complex mRNA sample, and assess the effect of a perturbation on gene expression. Methods utilizing genetic sequence microarrays can be applied to pharmaceutical target validation. In these methods, genetic modifications are evaluated for their effects on the expression of particular genes. A few examples include U.S. Pat. No. 6,013,437; Luria et al., "Method for identifying translationally regulated genes"; U.S. Pat. No. 6,004,755, Wang, "Quantitative microarray hybridization assays"; U.S. Pat. No. 6,340,565, Oliner, "Determining signal transduction pathways", and U.S. Pat. No. 5,994,076, Chenchik et al., "Methods of assaying differential expression".

Gene reporter assays can also be used to characterize the effect of genetic modifications by their ability to inhibit the expression of specific genes in gene reporter assays. For example, Ashby et al. U.S. Pat. No. 5,569,588; Rine and Ashby U.S. Pat. No. 5,777,888 describe a genome reporter matrix approach for comparing the effect of drugs on a panel of reporter genes to reveal effects of a compound on the transcription of a spectrum of genes in the genome.

SUMMARY OF THE INVENTION

The involvement of an expression product in a cell in a pathway is determined by introduction of an expression construct that provides for over-expression of a gene of interest in a cell in which a pathway is active or is activated by the over-expression of the gene. The cell is incubated with predetermined factors, and parameters affected by the pathway are measured to produce a BioMAP. By comparing the resulting BioMAP with BioMAPs of pathways of known response of the parameters to the factors, the relation of the gene of interest to a pathway can be determined.

BRIEF DESCRIPTION OF THE DRAWINGS

FIG. 1A. Expression of selected readout parameters on selected assay combinations of HUVEC treated with proinflammatory cytokines. FIG. 1B. Expression of selected readout parameters on selected assay combinations of HUVEC treated with cytokine combinations.

FIG. 1C. Expression of selected readout parameters on selected assay combinations of HUVEC treated with cytokine combinations.

FIGS. 2A-2C. FIG. 2A, Assay combinations for screening inflammatory modulators. FIG. 2B. A graphical representation of the data shown in FIG. 2A. FIG. 2C. A tree diagram representation of the biomaps prepared from data shown in FIGS. 2A and 2B.

FIGS. 3A-3B. Effect of neutralizing anti-TNF-α antibody on the expression of readout parameters in the inflammatory assay combination containing three factors (IL-1+TNF-α+IFN-γ). FIG. 3A. The relative expression of each parameter is shown along the y-axis as average value of the OD measured at 450 nm. FIG. 3B. A color-coded representation of biomaps prepared from the data shown in FIG. 3A.

FIG. 4A, Confluent cultures of HUVEC cells were treated with TNF-α (5 ng/ml)+IFN-γ (200 ng/ml)+IL-1 (20 ng/ml) in the presence or absence of 10 μM NHGA, 200 μM PDTC or 9 μM PD098059. FIG. 4B, 125-500 μM ibuprofen. FIG. 4C shows a visual representation of how these reference biomaps can be compared by pattern similarity and cluster analysis.

FIG. 5. Effect of neutralizing anti-TNF-α antibody or NFκB inhibitors M861 and nordihydroguaiaretic acid (NHGA) on readout patterns in multiple assay combinations.

FIG. 6. Effect of a neutralizing anti-TNF-α antibody on readout patterns in multiple assay combinations.

FIG. 8. Effect of Bcl-3 gene over-expression on readout patterns in multiple BioMap systems of inflammation.

FIG. 9. Effect of over-expression of bcl-2 and bcl-xl proteins on a panel of assay combinations.

DETAILED DESCRIPTION OF THE EMBODIMENTS

Figure 1A:
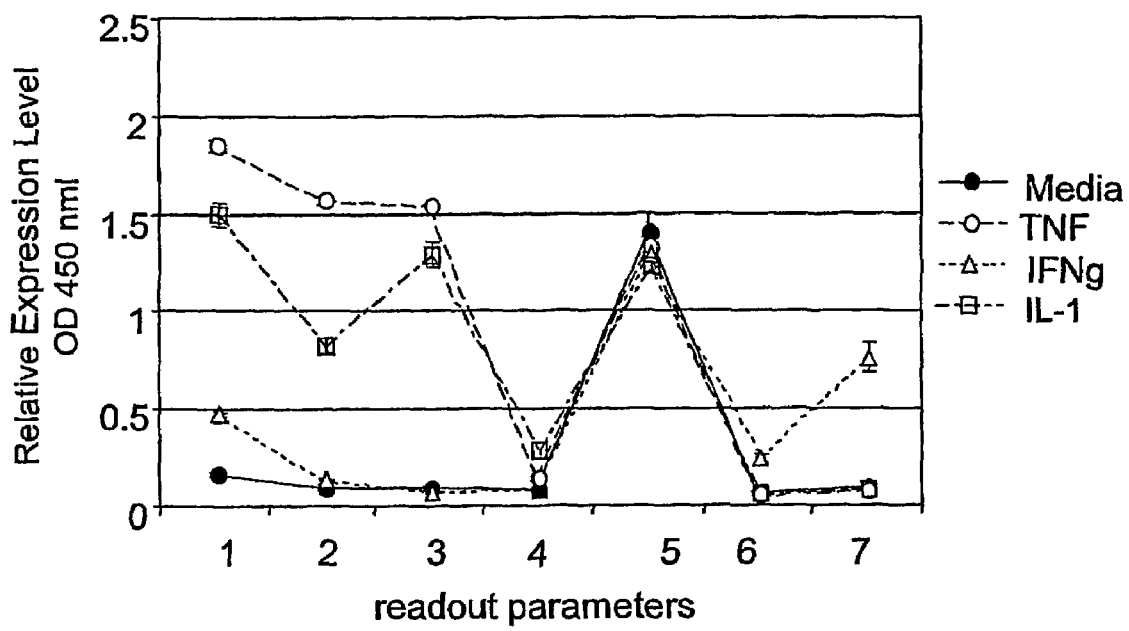
FIGS. 1A, 1B, 1C. Assay combinations for screening inflammatory modulators.

Methods and compositions are provided for screening or identifying cellular pathways with which genes are associated. The method employs BioMAPs, which are developed by the introduction of an expression construct that provides for over-expression of a gene of interest in a cell in which a pathway is active or is activated by the over-expression of the gene. The cell is incubated with predetermined factors that affect one or more pathways, and parameters affected by the pathway are measured to produce a BioMAP.

In performing the subject method, one or more cell types may be used, each having one or more pathways of interest, where each pathway is affected by certain factors, and provides for associated parameters. A basal BioMAP is used to define the response of the cells to individual and/or combinations of factors. The cells are then transformed with an expression construct for expressing the gene of interest to determine the relationship of the gene with one or more pathways. After ascertaining that there are cells in the culture that are expressing the gene of interest, the cells are then treated with one or more factors individually and/or in combination and the effect of the factors on the selected parameters determined. The BioMAP thus produced is compared to known BioMAPs. Where the variation in the parameter responses tracks the variations observed with known pathways, the result is highly suggestive that the gene of interest is associated with the particular pathway(s). Further studies may include inhibition of the gene of interest in cells expressing such gene and determining the cellular responses to the different factors.

Assay combinations, usually employing cell cultures, are provided that simulate physiological cell states of interest, particularly physiological cell states in vivo, usually using the same type of cells or combinations of cells. These cell cultures are created by the addition of a sufficient number of different factors to provoke a response that simulates cellular physiology of the state of interest and to allow for the status of cells in culture to be determined in relation to the enhanced expression of the gene of interest. The state of interest will normally involve a plurality of pathways where the pathways regulate a plurality of parameters or markers identifying a phenotype associated with the state of interest.

The phenotype can be generated by including one or more factors that induce pathways affecting the production of the phenotype by the up or down regulation of formation of the parameters as detectable products, or may be based on the nature of the cell, e.g. neoplastic primary cells, cell lines, etc., where the factors enhance the response of the cells in vitro to more closely approximate the response of interest. The factors are naturally occurring compounds, e.g. known compounds that have surface membrane receptors and induce a cellular signal that results in a modified phenotype, or synthetic compounds that mimic the naturally occurring factors. In some instances, the factors will act intracellularly by passing through the cell surface membrane and entering the cytosol with binding to components in the cytosol, nucleus or other organelle. In providing the environment by use of the factors or mimetics, one provides the activities of the factors to the environment, using the naturally occurring factors or their mimetics. In referring to factors, it is understood that it is the activities of the factors that are of interest and not necessarily a particular naturally occurring factor itself.

The nature and number of parameters measured generally reflects the response of a plurality of pathways. The subject approach provides for robust results having enhanced predictability in relation to the physiological state of interest. The results may be compared to the basal condition and/or the condition in the presence of one or more of the factors, and/or the condition in the presence and absence of agent or other condition appropriate for comparison. The effects of different environments are conveniently provided in BioMAPs, where the results can be mathematically compared.

The above-described approach is used for screening of genetic agents to identify the relationship of the gene product to one or more cellular pathways. Genetic agents are introduced into cells, which cells are placed in a medium where one or more factors are present to provide a desired environment in which various combinations of cell signaling pathways are stimulated. Of particular interest is an environment that resembles a physiological environment involved with an aberrant, e.g. diseased, state. Parameters associated with the pathways are monitored, in particular those that are related to the physiological state. Where the parameters show a pattern indicating the up or down regulation of a pathway, the genetic agent is deduced to encode, or to affect the expression of, a member of the pathway or a member that communicates with the pathway under the selected environmental conditions. In this way one can determine the role a gene product plays in the physiological state of interest, as well as define targets for therapeutic application.

Numerous factors are known that induce pathways in cells that are responsive to the factor. For the most part, factors bind to cell surface receptors, although other receptors may be involved, such as receptors at the nuclear membrane. In addition, where a factor is able to penetrate the surface membrane, through passive or active transport or through endocytosis, the factor may bind to components of a membrane, cytosol or an organelle, e.g. nucleus. By using a combination of multiple factors to provoke a cellular response, and determining multiple parameters associated with a physiological state of interest, one can investigate multiple individual cellular physiological pathways and simulate the physiological response so that over expression of a gene can be related to a particular pathway(s).

At least one factor, often multiple factors are employed, which provide a robust simulation of the physiologic pathways of interest and allow for reliable responses that can be correlated with in vivo cellular responses. Alternatively, factors can be employed that simulate the environment of the cells in vivo (particularly a living animal, but may be cells, tissue, organelles, etc.), so that the cell physiology of the cells in culture more closely approximates the cell physiology in vivo.

In referring to simulation to a physiological state for preparing the BioMAP as a standard, the simulation will usually include at least two, usually at least three, and may be, four or more different regulated features (parameters) shared with in vivo cell counterparts in normal or diseased states. Alternatively, the simulation may include a cell, culture system that will allow discrimination of a modification in at least two different signaling pathways or cell functions operative in vivo under conditions of interest.

The results can be entered into a data processor to provide a BioMAP dataset. Algorithms are used for the comparison and analysis of BioMAPs obtained under different conditions. The effect of factors and agents is read out by determining changes in multiple parameters in the BioMAP. The BioMAP will include the results from assay combinations with the genetically modified cells, and may also include one or more of the control state, the simulated state, and the results from other assay combinations using other agents or genetic modifications performed under other conditions. For rapid and easy comparisons, the results may be presented visually in a graph of a BioMAP, and can include numbers, graphs, color representations, etc.

BioMAP

The BioMAP is prepared from values obtained by measuring parameters or markers of the cells in the presence and absence of different factors, as well as comparing the presence of the expression product of interest and at least one other state, usually the control state, which may include the state without the genetic construct or with a different genetic construct or other appropriate situation. The parameters include cellular products or epitopes thereof, as well as functional states, whose levels vary in the presence of the factors. Desirably, the results are normalized against a standard, usually a "control value or state," to provide a normalized data set. Values obtained from test conditions can be normalized by subtracting the unstimulated control values from the test values, and dividing the corrected test value by the corrected simulated control value. In referring to "unstimulated" is intended that factors not be employed to simulate a physiological state or phenotype. Other methods of normalization can also be used; and the logarithm or other derivative of measured values or ratio of test to simulated or other control values may be used. Data is normalized to control data on the same cell type under control conditions, but a BioMAP may comprise normalized data from one, two or multiple cell types and assay conditions.

By referring to a BioMAP it is intended that the dataset will preferably comprise values of the levels of at least two sets of parameters obtained under different assay combinations. Depending on the use of the BioMAP, the BioMAP may also include the parameter, values for each the factors, included in the assay combination, individually and/or together with less than the entire assay combination. Compilations of BioMAPs' are developed that, provide the values for a sufficient number of alternative assay combinations to allow comparison of values obtained where factors have not been added. The parameter values are usually created electronically and stored in a data processor for comparison with other BioMAPs and databases compiled from the BioMAPs.

A graph of a BioMAP can be presented visually as numerical values, symbols, color gradations, or the like, indicating the parameter values. The graph is conveniently presented where color and/or design provide an indication of the level of the particular marker. The indicators may be vertical or horizontal as to the individual markers and the assay combinations, so that by looking at the graph, one can immediately compare the levels of the different markers for each of the combinations and discern patterns related to the assay combinations and the differences between assay combinations. In this way, one can rapidly relate different pathways, the pathways the genes affect and their efficacy in modulating the individual pathways.

Optionally, a BioMAP can be annotated to indicate information about the sources of information for the dataset. Annotations may include, for example, the number of assay conditions in a panel (n); controls used for normalization (N); parameters (P), which may be designated for the number and identity of the parameters; environmental changes, such as the addition of factors and/or agents or a change in the physical conditions (V); cell type (C); and the like. The annotation may further specify specific factors or conditions present in one of the assay combinations, e.g. n1, n2, n3, etc., where the presence of factors in the assay combination is designated (F), temperature may be designated (T), pH, etc. The parameters may also be designated in this as, e.g. P1=ICAM-1, P2=VCAM-1, P3=E-selectin, etc. Written out, the annotation may be set forth as: (v) B {n; N; P; C; F}.

As an example: a BioMAP is produced from monitoring endothelial cells for four parameters in four assay combinations. The assay combinations include a basal control, a stimulated control, and a control where the pathway of interest is blocked by the addition of neutralizing antibody. The gene of interest being evaluated is Gene A. The BioMAP (B) may be annotated as:

(Gene A) B {n=1-4; N=basal/stim.; P=1-4; Cendothelial; F(n1-4)=n1, n2, n3, n4}

A database of BioMAPs can be compiled from sets of experiments, where different pathways are stimulated and different BioMAPs are obtained by the addition of different sets of factors. The same set of factors may be used with different cell types, so that different pattern will be observed depending upon the cell type, even though the same pathway(s) may be stimulated.

Mathematical systems can be used to compare BioMAPs, and to provide quantitative measures of similarities and differences between them. For example, the BioMAPs in the database can be analyzed by pattern recognition algorithms or clustering methods (e.g. hierarchical or k-means clustering, etc.) that use statistical analysis (correlation coefficients, etc.) to quantify relatedness of BioMAPs. These methods can be modified (by weighting, employing classification strategies, etc.) to optimize the ability of a BioMAP to discriminate different functional effects. For example, individual parameters can be given more or less weight when analyzing the dataset of the BioMAP, in order to enhance the discriminatory ability of the BioMAP. The effect of altering the weights assigned each parameter is assessed, and an iterative process is used to optimize pathway or cellular function discrimination.

Assay Combination

Cells for use in the assays of the invention can be an organism, a single cell type derived from an organism, or can be a mixture of cell types, as is typical of in vivo situations, or may be the different cells present in a specific environment, e.g. vessel tissue, liver, spleen, heart muscle, brain tissue, etc. The cells will usually be of the same type as the cells of the physiologic conditions, sharing at least a partially common phenotype. For example, both the culture and the in vivo physiologic condition could involve T-lymphocytes, where the culture would involve a T-lymphocyte cell line or primary T-lymphocyte. In some instances the cells in the culture or assay combination may be substantially different from the cells of the physiologic state of interest. Where it is known or can be shown that the pathways of the cells in culture are paradigmatic of the pathways of the cells of interest, the cells in culture may be selected for reasons of convenience, that a body of data has been built up with these cells, easy growth and maintenance, the use by others allowing for more accurate comparisons of the results, etc.

Of particular interest are primary cells that can be used in a culture, where the primary cells of interest are, in effect, synchronized in their phenotype, by the use of the factors. When the cells are not in synchrony, an average value will be obtained. The culture conditions will include the presence of factors that provide for the desired physiologic state, including the desired phenotype, but may also be varied, for example, as to temperature, pH, presence of other cell types, and the like. Each combination of cell(s) and culture conditions provides one "assay combination", which will generate a set of parameter readouts. In a typical screen, a panel of one or more assay combinations is used for each expression construct to be tested. For each assay combination, a set of parameter readouts will be obtained in the presence of an expression construct that is being tested. These readouts will be compared to readouts of an assay combination lacking the expression construct, which may be performed contemporaneously or may be performed at another time, either before or after the assay combination with the expression construct of interest. As indicated above, the comparison may be with the same type of cells in the absence of the factors, in the presence of the factors, or multiple stimulating or inhibiting factors or in the presence of a different expression construct or agent or other condition that serves to provide a meaningful comparison.

Single cell types are of interest for many screening applications, and in individual assay combinations will be provided with factors that induce the desired phenotype. The factors may be the products of other cell types, for example, expressed proteins associated with a disease, may be compounds that simulate naturally occurring factors, may be surface membrane proteins free of the membrane or as part of microsomes, or other reagent that induces the appropriate pathway to aid in the simulation of the phenotype or provides the appropriate environment to simulate the physiological condition. The factors (including mimetics thereof may be added individually or in combination, from feeder cells, may be added as a bolus or continuously, where the factor is degraded by the culture, etc. Illustrative naturally occurring factors include cytokines, soluble receptors, hormones, prostaglandins, steroids, etc, that may be isolated from natural sources or produced by recombinant technology or synthesis, compounds that mimic the action of other compounds or cell types, e.g. an antibody which acts like a factor or mimics a factor, or synthetic drugs that act as ligands for target receptors. For example, in the case of the T cell receptor, the action of an oligopeptide processed from an antigen and presented by an antigen-presenting cell, etc. can be employed. Where a family of related factors are referred to with a single designation, e.g. IL-1, VEGF, IFN, etc., in referring to the single description, any one or some or all of the members of the group are intended, where the literature will be aware of how the factors are to be used in the context of the assay combination.

The assay combinations find use in investigating complex states of cells, frequently resulting from cellular interactions, which may frequently involve at least about two, frequently three, or more different cell types and/or will involve a plurality of soluble factors that are present in a physiological fluid, particularly as the result of a physiological event, e.g. infection, neoplasia, autoimmune, etc. that is, frequently involving more than one cell type and more than one factor. The measured parameters may be obtained from one or, more of the cell types. The cells in the assay combination, either one or up to each of the different cell types can have identifying characteristics allowing them to be distinguished during analysis. Various techniques may be employed to identify the cells in the assay combination for analysis of the parameters of interest.

Conditions of interest include inflammatory processes that occur in response to infection, trauma, etc., autoimmune diseases, such as diabetes, lupus, arthritis, etc., cardiovascular diseases, such as stroke, atherosclerosis, etc., neoplasia, hyperplasia, addiction, infection, obesity, cellular degeneration, apoptosis, senescence, differentiation, and the like.

Multifactorial, usually involving multicellular, assay combinations, may reflect many of the conditions indicated above, such as inflammatory processes; autoimmune diseases; cardiovascular diseases; tumors, etc. That is, a multiplicity of factors is employed to influence a plurality of cellular pathways and a multiplicity of parameters is measured that reflect the status of the pathways. Degenerative diseases, including affected tissues and surrounding areas, may be exploited to determine both the response of the affected tissue, and the interactions with other cell types or other parts of the body.

The invention is suitable for use with any cell type, including primary cells, normal and transformed cell lines, transduced cells, transfected cells and cultured cells. The present invention is suitable for use with single cell types or cell lines; or combinations thereof. In assays the cultured cells may maintain the ability to respond to stimuli that elicit a response in their naturally occurring counterparts. Cultured cells may have gone through up to five passages or more, sometimes 10 passages or more. These may be derived from all sources, particularly mammalian, and with respect to species, e.g., human, simian, rodent, etc., although other sources of cells may be of interest in some instances, such as plant, fungus, etc.; tissue origin, e.g. heart, lung, liver, brain, vascular, lymph node, spleen, pancreas, thyroid, esophageal, intestine, stomach, thymus, etc.

In addition, cells that have been genetically altered with recombinant genes or by antisense technology, to provide a gain or loss of genetic function, may be utilized with the invention. Methods for generating genetically modified cells are known in the art, see for example "Current Protocols in Molecular Biology", Ausubel et al., eds, John Wiley & Sons, New York, N.Y., 2000. The genetic alteration may be a knock-out, usually where homologous recombination results in a deletion that knocks out expression of a targeted gene; or a knock-in, where a genetic sequence not normally present in the cell is stably introduced.

A variety of methods may be used in the present invention to achieve a knock-out, including site-specific recombination, expression of anti-sense or dominant negative mutations, and the like. Knockouts have a partial or complete loss of function in one or both alleles of the endogenous gene in the case of gene targeting. Preferably expression of the targeted gene product is undetectable or insignificant in the cells being analyzed. This may be achieved by introduction of a disruption of the coding sequence, e.g. insertion of one or more stop codons, insertion of a DNA fragment, etc., deletion of coding sequence, substitution of stop codons for coding sequence, etc. In some cases the introduced sequences are ultimately deleted from the genome, leaving a net change to the native sequence.

Different approaches may be used to achieve the "knock-out". A chromosomal deletion of all or part of the native gene may be induced, including deletions of the non-coding regions, particularly the promoter region, 3' regulatory sequences, enhancers, or deletions of gene that activate expression of the targeted genes. A functional knock-out may also be achieved by the introduction of an anti-sense construct that blocks expression of the native genes (for example, see Li and Cohen (1996) Cell 85:319-329). "Knock-outs" also include conditional knock-outs, for example where alteration of the target gene occurs upon exposure of the animal to a substance that promotes target gene alteration, introduction of an enzyme that promotes recombination at the target gene site (e.g. Cre in the Cre-lox system), or other method for directing the target gene alteration.

The genetic construct may be introduced into tissues or host cells by any number of routes, including calcium phosphate transfection, viral infection, microinjection, electroporation or fusion of vesicles. Jet injection may also be used for intramuscular administration, as described by Furth et al. (1992), Anal Biochem 205:365-368. The DNA may be coated onto gold microparticles, and delivered intradermally by a particle bombardment device, or "gene gun" as described in the literature (see, for example, Tang et al. (1992), Nature 356:152-154), where gold microprojectiles are coated with the DNA, then bombarded into cells.

A number of selection systems may be used for introducing the genetic changes, including but not limited to the herpes simplex virus thymidine kinase (Wigler, et al., 1977, Cell 11:223), hypoxanthine-guanine phosphoribosyltransferase (Szybalska & Szybalski, 1962, Proc. Natl. Acad. Sci. USA 48:2026), and adenine phosphoribosyltransferase (Lowy, et al., 1980, Cell 22:817) genes can be employed in tk.sup.-; hgprt.sup.- or aprt.sup.- cells, respectively. Also, antimetabolite resistance can be used as the basis of selection for the following genes: dhfr, which confers resistance to methotrexate (Wigler, et al., 1980, Natl. Acad. Sci. USA 77:3567; O'Hare, et al., 1981, Proc. Natl. Acad. Sci. USA 78:1527); gpt, which confers resistance to mycophenolic acid (Mulligan & Berg, 1981, Proc. Natl. Acad. Sci. USA 78:2072); neo, which confers resistance to the aminoglycoside G-418 (Colberre-Garapin, et al., 1981, J. Mol. Biol. 150:1); and hygro, which confers resistance to hygromycin (Santerre, et al., 1984, Gene 30:147).

The literature has ample evidence of cells involved with many physiological states of interest, factors involved in inducing changes in the phenotype, and parameters or markers resulting from the interaction between the factors and the target cells affected by the factors. Primary cells for tissues of interest are readily available commercially and can be expanded as required. Biopsies can serve as a source of cells, both normal and diseased cells.

Cell types that can find use in the subject invention, include endothelial cells, muscle cells, myocardial, smooth and skeletal muscle cells, mesenchymal cells, epithelial cells;

hematopoietic cells, such as lymphocytes, including T-cells, such as Th1 T cells, Th2 T cells, Th0 T cells, cytotoxic T cells; B cells, pre-B cells, etc.; monocytes; dendritic cells; neutrophils; and macrophages; natural killer cells; mast cells;, etc.; adipocytes, cells involved with particular organs, such as thymus, endocrine glands, pancreas, brain, such as neurons, glia, astrocytes, dendrocytes, etc. and genetically modified cells thereof. Hematopoietic cells will be associated with inflammatory processes, autoimmune diseases, etc., endothelial cells, smooth muscle cells, myocardial cells, etc. may be associated with cardiovascular diseases; almost any type of cell may be associated with neoplasias, such as sarcomas, carcinomas and lymphomas; liver diseases with hepatic cells; kidney diseases with kidney cells; etc.

The cells may also be transformed or neoplastic cells of different types, e.g. carcinomas of different cell origins, lymphomas of different cell types, etc. The American Type Culture Collection (Manassas, Va.) has collected and makes available over 4,000 cell lines from over 150 different species, over 950 cancer cell lines including 700 human cancer cell lines. The National Cancer Institute has compiled clinical, biochemical and molecular data from a large panel of human tumor cell lines, these are available from ATCC or the NCI (Phelps et al. (1996) Journal of Cellular Biochemistry Supplement 24:32-91). Included are different cell lines derived spontaneously, or selected for desired growth or response characteristics from an, individual cell line; and may include multiple cell lines derived from a similar tumor type but from distinct patients or sites.

In addition, cells may be environmentally induced variants of single cell lines e.g., a responsive cell line, such as a transformed endothelial cell line, split, into independent cultures and grown under distinct conditions, for example with or without cytokines, e.g. IL-1, with or without IFN-gamma (with or without endothelial growth factors, and in the presence or absence of other cytokines or combinations thereof. Each culture condition then induces specific distinctive changes in the cells, such that subsequent responses to an environment change are distinct, yielding a distinctive BioMAP. Alternatively, the cells may be transduced or otherwise genetically modified cells with genetic material other than the gene of interest.

The term "environment," or "culture condition" encompasses cells, media, factors, time and temperature. Environments may also include drugs and other compounds, particular atmospheric conditions, pH, salt composition, minerals, etc. The conditions will be controlled and the BioMAP will reflect the similarities and differences between each of the assay combinations involving a different environment or culture condition.

Culture of cells is typically performed in a sterile environment, for example, at 37° C. in an incubator containing a humidified 92-95% air/5-8% $CO_2$ atmosphere. Cell culture may be carried out in nutrient mixtures containing undefined biological fluids such as fetal calf serum, or media which is fully defined and serum free.

Some preferred environments include environments that discriminate or emphasize cell or tissue states associated with pathology in one or more diseases, for example, Th1 versus Th2 polarization of effector T cells; prothrombotic; inflammatory (e.g. NFκB, upregulated TNF-alpha cytokine production, downregulated IL-10, TGF", etc.; dysregulated proliferation (neoplasia); angiogenesis; etc.) Environments that facilitate discrimination of specific signaling pathways implicated in disease states are also of interest, e.g. NFκB, classic Th1 or Th2 induction environments, etc.

Physiologically Relevant Assay Combination

Cell culture conditions that reflect multiple aspects of a physiological state are termed herein a "representation" or "simulation" of the condition of interest, normally the in vivo condition. There are several important, and interrelated variables to be considered when setting up the in vitro counterpart conditions. These include the types of cells that are involved, the media employed, the conditions for the culture, the presence of biologically, active factors in the cell's physiological milieu; and the phenotype of the cells, which may be determined both in the absence and presence of pharmacologic agents or for genetically modified (other than the expression construct of interest) and unmodified cells. While a single cell can find use in an assay combination, normally the number of cells will be at least $10^2$, usually at least $10^3$, and conveniently are grown to confluence.

In many cases the literature has sufficient information to establish assay combinations to provide a useful BioMAP. Where the information is not available, by using the procedures described in the literature for identifying markers for diseases, using subtraction libraries, microarrays for RNA transcription comparisons, proteomic or immunologic comparisons, between normal and cells in the physiologic state of interest, using knock-out and knock-in animal models, using model animals that simulate the physiological state, by introducing cells or tissue from one species into a different species that can accept the foreign cells or tissue, e.g. immunocompromised host, one can ascertain the endogenous factors associated with the physiologic state and the markers that are produced by the cells associated with the physiologic state.

Once a BioMAP of the components of the assay combination have been shown to be relevant to a physiologic state of interest, BioMAP analysis can be used to optimize cell culture conditions that more accurately represent or simulate such physiologic state in vivo, e.g. in disease states of interest. That is, the values for various parameters from cells in vivo can be used as a template for the process of representing those same cells in culture. Additional markers can be deduced and added as a marker to the map. The greater the number of individual markers that vary independently of each other, the more robust the BioMAP. By optimizing culture conditions and selection of parameters, a BioMAP from a cell panel in vitro can be made representative of an in vivo phenotype. In other words, in vitro culture conditions can be manipulated in order to generate cells having a BioMAP that mimics the parameter readout obtained from similar cells in a specific in vivo state of interest. There will usually be employed for generation of the BioMAP at least about three parameter or marker readouts, more frequently 4 or more, generally not more than 20, more usually not more than about 10, that have similar response patterns in the in vitro and in vivo conditions. A larger number of shared parameters indicates a greater relevance of the cultured cells for the normal or disease state and will usually be indicative of a plurality of pathways associated with the physiologic state in vivo. The parameters selected will permit the readout of at least 2, more usually, at least about 3 or more cell pathways.

If desired, the parameters of the BioMAP can be optimized by obtaining. BioMAP parameters within an assay combination or panel of assay, combinations using different sets of readout, and using pattern recognition algorithms and statistical analyses to compare and contrast different BioMAPs of different parameter sets. Parameters are selected that provide a BioMAP that discriminates between changes in the environment of the cell-culture known to have different modes of action, i.e. the BioMAP is similar for agents with a common mode of action, and different for agents with a different mode of action. The optimization process allows the identification and selection of a minimal set of parameters, each of which provides a robust readout, and that together provide a BioMAP that enables discrimination of different modes of action resulting from gene over expression. The iterative process focuses on optimizing the assay combinations and readout parameters to maximize efficiency and the number of signaling pathways and/or functionally different cell states produced in the assay configurations that can be identified and distinguished, while at the same time minimizing the number of parameters or assay combinations required for such discrimination.

There are established protocols for the culture of diverse cell types that reflect their in vivo counterparts. Protocols may require the use of special conditions and selective media to enable cell growth or expression of specialized cellular functions. Such methods are described in the following: Animal Cell Culture Techniques (Springer Lab Manual), Clynes (Editor), Springer Verlag,1998; Animal Cell Culture Methods (Methods in Cell Biology, Vol 57, Barnes and Mather, Eds, Academic Press, 1998; Harrison and Rae, General Techniques of Cell Culture (Handbooks in Practical Animal Cell Biology), Cambridge University Press, 1997; Endothelial Cell Culture (Handbooks in Practical Animal Cell Biology), Bicknell (Editor), Cambridge University Press, 1996; Human Cell Culture, Cancer Cell Lines Part I: Human Cell Culture, Masters and Palsson, eds., Kluwer Academic Publishers, 1998; Human Cell Culture Volume II—Cancer Cell Lines Part 2 (Human Cell Culture Volume 2), Masters and Palsson, eds., Kluwer Academic Publishers, 1999; Wilson, Methods in Cell Biology: Animal Cell Culture Methods (Vol 57), Academic Press, 1998; Current Protocols in Immunology, Coligan et al., eds, John Wiley & Sons, New York, N.Y., 2000; Current Protocols in Cell Biology, Bonifacino et al., eds, John Wiley & Sons, New York, N.Y., 2000.

The, cell expression of various surface and intracellular markers, including protein, lipid, nucleic acid, e.g. genetic markers, and carbohydrate is known for a large number of different types of cells, and can be used as a reference for establishing the exact phenotype of cells-in vivo; for determining whether that same phenotype is present in the cultured cells, for determining the effect of gene expression, and ancillary to that, the effect of an agent, particularly a pharmacologic agent, ion the cells, and the like. The manner in which) cells respond to an agent in establishing the nature of the response of the cells, particularly to a pharmacologic agent, including the timing of responses, is an important reflection of the physiologic state of the cell in which the gene of interest is being expressed.

For example, one might determine by histologic and antibody staining the phenotypes of cells in a biopsy sample from a chronically inflamed tissue. This information would be used to determine the types of cells that are present, and their physiologic state, e.g. activated, responding to a cytokine, etc. and their environment, e.g. presence of cytokines. A corresponding assay combination is then established from the information, which provides the relevant cells in the appropriate state. A BioMAP is then derived from the assay combination and controls to provide an in vitro culture as an appropriate surrogate for the in vivo state. Usually, an in vivo response will match multiple parameter values (i.e. up or down regulation of parameters) to similarly responding cells in a "representative" assay combination.

As indicated previously, for many physiologic states, cell types, factors and markers are known. In addition, concentrations having the desired induction of change in phenotype are also known. Also as discussed above, these conditions can be further optimized by making variations in concentrations, ratios, choice of markers, etc. to provide more accurate simulations of the naturally occurring physiological state. Assay combinations that represent in vivo states may go through an iterative process. Based on the information in the literature or independently derived, one devises an initial set of culture conditions, which includes combinations of known biologically active factors. Depending on the desired BioMAP, these factors can include cytokines, chemokines, and other factors, e.g. growth factors, such factors include GM-CSF, G-CSF, M-CSF, TGF, FGF, EGF, TNF-alpha", GH, corticotropin, melanotropin, ACTH, etc., extracellular matrix components, surface membrane proteins, such as integrins and adhesins, and other components that are expressed by the targeted cells or their surrounding milieu in vivo. Components may also include soluble or immobilized recombinant or purified receptors, or antibodies against receptors or ligand mimetics.

For cells, either primary cells or cell lines, that have the appropriate phenotype, e.g. neoplastic cells, factors will be used to provide an environment that simulates the environment of the neoplastic cells in vivo. Depending on the type of cancer, the cancer cells will be perfused with different factors based on the different cells in the environment of the tumor, as well as other factors in the blood induced by factors secreted by the neoplastic cells. Since the physiology of the cells is influenced by these factors, which in turn will-influence the regulation of the parameters to be measured, providing these factors enhance the approximation of the cells in culture to the cells in vivo, providing for a more accurate readout of the effect of a genetic agent on the cells. Many of these factors will be the same factors described above, but additional factors include factors associated with angiogenesis, such as angiogenin, angiopoietin-1, HGF, PDGF, TNF-$\alpha$, VEGF, IL-1, IL-4, IL-6, IL-8 and fibronectin.

An initial set of readout parameters is selected, which normally includes parameters that are differentially produced, expressed, modulated or indirectly influenced in response to one or more of the components included in the environment. These parameters normally include molecules of functional importance to the cell and which are relevant to the state of interest. The readout response of cells is measured in response to a defined event, e.g. the modification of the genotype of the cell. The resulting BioMAP (normalized set of parameter values) comprising the presence and relative amount of the markers will simulate the BioMAP of the relevant cells in vivo. The assay conditions used to generate the BioMAP may be further refined to most closely match the BioMAP of the cells in vivo in the physiologic state of interest or mimic at least about 3 features of interest of such cells in vivo.

The pattern of factors and parameters is applicable with genetically modified cells, where the assay combination has the genetically modified cell as its variable. The genetically modified cells are scored for changes in parameters, as compared to the genetically unmodified cells. The results are used to develop a BioMAP, where the BioMAP of the genetically modified cell can be compared to the unmodified cells, one or the other or both of other genetically modified cells and assay combinations involving exogenous agents. The compiled database of BioMAPs can include both BioMAPs of genetic modifications, and BioMAPs for the effects of other compounds. The BioMAPs provide identification of the pathways involved, the relationship of the activities of exogenous agents to genes and how they affect target pathways, and how the cell modifies its biology in relation to these changes.

Genetic Agents

As used herein, the term "genetic agent" refers to polynucleotides and analogs thereof, which-agents are tested in the screening assays of the invention by addition of the genetic agent, to a cell. The introduction of the genetic agent results in an alteration of the total genetic composition of the cell. As employed herein, the genetic agent results in the expression of a protein and is being evaluated as to its effect on one or more target pathways. The genetic agents such as DNA result in an experimentally introduced change in the genome of a cell, generally through the integration of the sequence into a chromosome. Genetic changes can also be transient, where the exogenous sequence is not integrated but is maintained as an episomal agent. RNA viruses may be employed that comprise the gene of interest and are reverse transcribed and inserted into the genome of the host cell. Genetic agents (polypeptides or polynucleotides) can also be sythesized in vitro and delivered to cells by conjugation to a moiety (e.g antennapedia 16-amino acid "Penetratin-1 peptide, available from Qbiogene) that promotes transfer of the agent into a cell of interest. The effect of a genetic agent is to increase expression of a particular gene product in the cell with the potential for the increase and/or decrease of other products in the cell.

Introduction of an expression vector encoding a polypeptide can be used to express the encoded product in cells to over-express the product, in the presence or absence of expression of the product. Various promoters can be used that are constitutive or subject to external regulation, where in the latter situation, one can turn on or off the transcription of a gene. These coding sequences may include full-length cDNA or genomic clones, fragments derived therefrom, or chimeras that combine a naturally occurring sequence with functional or structural domains of other coding sequences. Alternatively, the introduced sequence may encode a dominant negative mutation, or dominant or constitutively active mutations of native sequences; altered regulatory sequences, etc.

In addition to sequences derived from the host cell species, other sequences of interest include, for example, genetic sequences of pathogens, for example coding regions of viral, bacterial and protozoan genes, particularly where the genes affect the function of human or other host cells, where knowledge of the pathway(s) affected by the infection is important in developing appropriate therapeutics. Sequences from other species may also be introduced, where there may or may not be a corresponding homologous sequence.

A large number of public resources are available as a source of genetic sequences, e.g. for human, other mammalian, and human pathogen sequences. A substantial portion of the human genome is sequenced, and can be accessed through public databases such as Genbank. Resources include the uni-gene set; as well as genomic sequences. For example, see Dunham et. al. (1999) Nature 402, 489-495; or Deloukas et al. (1998) Science 282, 744-746.

cDNA clones corresponding to many human gene sequences are available from the. IMAGE consortium. The international IMAGE Consortium laboratories develop and array cDNA clones for worldwide use. The clones are commercially available, for example from Genome Systems, Inc., St. Louis, Mo. Methods for cloning sequences by PCR based on DNA sequence information are also known in the art.

Dominant negative mutations are readily generated for corresponding proteins. These may act by several different mechanisms, including mutations in a substrate-binding domain; mutations in a catalytic domain; mutations in a protein-binding domain (e.g. multimer forming, effector, or activating protein binding domains); mutations in cellular localization domain, etc. See Rodriguez-Frade et al. (1999) P.N.A.S. 96:3628-3633; suggesting that a specific mutation in the DRY sequence of chemokine receptors can produce a dominant negative G protein linked receptor; and Mochly-Rosen (1995) Science 268:247.

A mutant polypeptide may interact with wild-type polypeptides (made from the other allele) and form a non-functional multimer. For example, as has been described for dominant negative mutants of the epidermal growth factor receptor and the chemokine receptor CCR2 (Kashles, 1991, Mol. Cell Biol, 11:1454; Rodriguez-Frade, 1999, PNAS 96:3628). Mutations or deletions of catalytic subunits of signaling molecules can also create dominant-negative mutants as, for example, dominant negative mutants of ras and rho family GTPases (Porfiri, 1996, J. Biol. Chem. 271:5871; de Pozo, Eur J. Immunol., 1999, 29:3609), protein tyrosine phosphatase 1B (Arregui, 1998, J. Cell Biol. 143:861), and the guanine nucleotide exchange factor CDC25(Mm) (Vanoni, 1999, J. Biol. Chem. 274:36656). Mutations that alter subcellular localization can also create dominant negative mutants, as for example, a protein kinase B dominant negative mutant described by van Weeren (1998, J. Biol. Chem. 273:13150). Mutations that alter adapter function also create dominant negative mutants, as for example dominant negative mutants of the SH2/SH3 adapters Nck and Grb2 (Gupta, 1998, Oncogene, 17:2155) and a deletion mutant of STAT5A (llaria, 1999, Blood, 93: 4154).

Preferably, the mutant polypeptide will be overproduced. Point mutations are made that have such an effect. In addition, fusion of different polypeptides of various lengths to the terminus of a protein, or deletion of specific domains can yield dominant negative mutants. General strategies are available for making dominant negative: mutants (see for example, Herskowitz (1987) Nature 329:219, and the references, cited above). Such techniques are used to create loss of function mutations, which are useful for determining protein function.

The level and timing of expression of the polypeptide can be controlled using various strategies. For example, tetracycline or ecdysone inducible expression systems are known in the art (e.g. Tet-On system from Clontech and Complete Control Inducible Expression System from Stratagene). Biological activity of the polypeptide can also be controlled by fusing the polypeptide to estrogen receptor (see for example Boehmelt (1992) EMBO 11:4641). The biological activity of such fusion protein is activated by addition of 4-hydroxytamoxifen into cell culture media.

Methods that are well known to those skilled in the art can be used to construct expression vectors containing coding sequences and appropriate transcriptional and translational control signals for increased expression of an exogenous gene introduced into a cell. These methods include, for example, in vitro recombinant DNA techniques, synthetic techniques, and in vivo genetic recombination. Alternatively, RNA capable of encoding gene product sequences may be chemically synthesized using, for example, synthesizers. See, for example, the techniques described in "Oligonucleotide Synthesis", 1984, Gait, M. J. ed., IRL Press, Oxford.

A variety of host-expression vector systems may be utilized to express a genetic coding sequence. Expression constructs may contain promoters derived from the genome of mammalian cells, e.g., metallothionein promoter, elongation factor promoter, actin promoter, etc., from mammalian viruses, e.g., the adenovirus late promoter; the vaccinia virus 7.5K promoter, SV40 late promoter, cytomegalovirus, etc.

In mammalian host cells, a number of viral-based expression systems may be utilized, e.g. retrovirus, lentivirus, adenovirus, herpesvirus, and the like. In cases where an adenovirus is used as an expression vector, the coding sequence of interest may be ligated to an adenovirus transcription/translation control complex, e.g., the late promoter and tripartite leader sequence. This gene may then be inserted in the adenovirus genome by in vitro or in vivo recombination. Insertion in a non-essential region of the viral genome (e.g., region E1 or E3) will result in a recombinant virus that is viable and capable of expressing the gene product in infected hosts (see Logan & Shenk, 1984, Proc. Natl. Acad. Sci. USA 81:3655-3659). Specific initiation signals may also be required for efficient translation of inserted gene product coding sequences. These signals include the ATG initiation codon and adjacent sequences. Standard systems, for generating adenoviral vectors for expression on inserted sequences are available from commercial sources, for example the Adeno-X™ expression system from Clontech (Clontechniques (January 2000) p 10-12).

In cases where an entire gene, including its own initiation codon and adjacent sequences, is inserted into the appropriate expression vector, no additional translational control signals may be needed. However, in cases where only the gene coding sequence is inserted, exogenous translational control signals, including, perhaps, the ATG initiation codon, must be provided. Furthermore, the initiation codon must be in phase with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc. (see Bittner et al., 1987, Methods in Enzymol. 153:516-544).

In a preferred embodiment, methods are used that achieve a high efficiency of transfection, and therefore circumvent the need for using selectable markers. These may include adenovirus infection (see, for example Wrighton, 1996, J. Exp. Med. 183: 1013; Soares, J. Immunol., 1998, 161: 4572; Spiecker, 2000, J. Immunol 164: 3316; and Weber, 1999, Blood 93: 3685); and lentivirus infection (for example, International Patent Application WO000600; or WO9851810). Adenovirus-mediated gene transduction of endothelial cells has been reported with 100% efficiency. Retroviral vectors also can have a high efficiency of infection with endothelial cells; Inaba et al. (1998, J Surg Res 78:31) report 40-77% efficiency. Other vectors of interest include lentiviral vectors, for examples, see Barry et al. (2000) Hum Gene Ther 11(2):323-32; and Wang et al. (2000) Gene Ther 7(3):196-200.

For the purpose of analysis of the effect of gene overexpression introduction of the test gene into a majority of cells (>50%) in a culture is sufficient. This can be achieved using viral vectors, including retroviral vectors (e.g. derived from MoMLV, MSCV, SFFV, MPSV, SNV etc), lentiviral vectors (e.g. derived from HIV-1, HIV-2, SIV, BIV, FIV etc.), adeno-associated virus (AAV) vectors, adenoviral vectors (e.g. derived from Ad5 virus), SV40-based vectors, Herpes Simplex Virus (HSV)-based vectors etc. A preferred vector construct will coordinately express a test gene and a marker gene such that expression of the marker gene can be used as an indicator for the expression of the test gene, as well as for analysis of gene transfer efficiency. This can be achieved by linking the test and a marker gene with an internal ribosomal entry site (IRES) sequence and expressing both genes from a single bi-cistronic mRNA. IRES sequence could be from a virus (e.g. EMCV, FMDV etc) or a cellular gene (e.g. eIF4G, BiP, Kv1.4 etc). The examples, of marker genes include drug resistance genes (neo; dhfr, hprt, gpt, bleo, puro etc) enzymes (9-galactosidase, alkaline phosphatase etc) fluorescent genes (e.g. GFP, RFP, BFP, YFP) or surface markers (e.g. CD24, NGFr, Lyt-2 etc). A preferred marker gene is biologically inactive and can be detected by standard immunological methods. Alternatively, an "epitope tag" could be added to the test gene for detection of protein expression. Examples of such "epitope tags" are c-myc and FLAG (Stratagene). A preferred viral vector will have minimal or no biological effect on the BioMAP apart from the genetic agent being tested. An example of such viral vectors is retroviral vectors derived from the MoMLV or related retroviruses, as listed above. By gating on the population of genetically modified cells, the unmodified cells in the culture can be excluded from analysis, or can be compared directly with the genetically modified cells in the same assay combination. For example, see Bowman et al. (1998) J. Biol. Chem. 273:28040-28048.

Screening Methods

Genetic agents are screened for biological activity by adding the to the cells comprising the agent at least one and usually a plurality of assay combinations to form a panel of assay combinations, usually in conjunction with assay combinations with cells lacking the genetic agent. The change in parameter readout in response to the genetic agent is measured, desirably normalized, and the resulting BioMAP may then be evaluated by comparison to reference BioMAPs. The reference BioMAPs may include basal readouts in the presence and absence of the factors, BioMAPs obtained with other genetic agents, which may or may not include known inhibitors of known pathways, etc. Genetic agents of interest for analysis include any biologically active protein with the capability of modulating, directly or indirectly, the phenotype of interest of a cell of interest.

In some instances, chemical agents of known activity may be added to the culture medium. These chemical agents may serve to activate a pathway, inhibit a pathway, etc., where there is interest in having a pathway other than the pathway of interest modulated and rather than using a natural factor, a chemical agent may be more convenient. The chemical agents are conveniently added in solution, or readily soluble form, to the medium of cells in culture. The chemical agents may be added in a flow-through system, as a stream, intermittent or continuous, or alternatively, adding a bolus of the compound, singly or incrementally, to an otherwise static solution. In a single solution method, a bolus of the chemical agent is added to the volume of medium surrounding the cells. The overall concentrations of the components of the culture medium should not change significantly with the addition of the bolus. Preferred chemical agent formulations do not include additional components, such as preservatives, that may have a significant effect on the, overall formulation. Thus preferred formulations consist essentially of a, biologically active compound and a physiologically acceptable carrier, e.g. water, ethanol, DMSO, etc. However, if a compound is liquid without a solvent, the formulation may consist essentially of the compound itself.

Various methods can be utilized for quantifying the presence of the selected markers. For measuring the amount of a molecule that is present, a convenient method is to label a molecule with a detectable moiety, which may be fluorescent, luminescent, radioactive, enzymatically active, etc., particularly a molecule specific for binding to the parameter with high affinity. Fluorescent moieties are readily available for labeling virtually any biomolecule, structure, or cell type. Immunofluorescent moieties can be directed to bind not only to specific proteins but also specific conformations, cleavage products, or site modifications like phosphorylation. Individual peptides and proteins can be engineered to autofluoresce, e.g. by expressing them as green fluorescent protein chimeras inside cells (for a review see Jones et al. (1999) Trends Biotechnol. 17(12):477-81). Thus, antibodies can be genetically modified to provide a fluorescent dye as part of their structure.

The use of high affinity antibody binding and/or structural linkage during labeling provides dramatically reduced non-specific backgrounds, leading to clean signals that are easily detected. Such extremely high levels of specificity enable the simultaneous use of several different fluorescent labels, where each preferably emits at a unique color. Fluorescence technologies have matured to the point where an abundance of useful dyes are now commercially available. These are available from many sources, including Sigma Chemical Company (St. Louis Mo.) and Molecular Probes (Handbook of Fluorescent Probes and Research Chemicals, Seventh Edition, Molecular Probes, Eugene Oreg.). Other fluorescent sensors have been designed to report on biological activities or environmental changes, e.g. pH, calcium concentration, electrical potential, proximity to other probes, etc. Methods of interest include calcium flux, nucleotide incorporation, quantitative PAGE (proteomics), etc.

Highly luminescent semiconductor quantum dots (zinc sulfide-capped cadmium selenide) have been covalently coupled to biomolecules for use in ultrasensitive biological detection (Stupp et al. (1997) Science 277(5330):1242-8; Chan et al. (1998) Science 281(5385):2016-8). Compared with conventional fluorophores, quantum dot nanocrystals have a narrow, tunable, symmetric emission spectrum and are photochemically stable (Bonadeo et al. (1998) Science 282(5393):-4736). The advantage of quantum dots is the potential for exponentially large numbers of independent readouts from a single source or sample.

Multiple fluorescent labels can be used on the same sample and individually detected quantitatively, permitting measurement of multiple cellular responses simultaneously. Many quantitative techniques have been developed to harness the unique properties of fluorescence including: direct fluorescence measurements, fluorescence resonance energy transfer (FRET), fluorescence polarization or anisotropy (FP), time resolved fluorescence (TRF), fluorescence lifetime measurements (FLM), fluorescence correlation spectroscopy (FCS), and fluorescence photobleaching recovery (FPR) (Handbook of Fluorescent Probes and Research Chemicals, Seventh Edition, Molecular Probes, Eugene Oreg.).

Depending upon the label chosen, parameters may be measured using other than fluorescent labels, using such immunoassay techniques as radioimmunoassay (RIA) or enzyme linked immunosorbance assay (ELISA), homogeneous enzyme immunoassays, and related non-enzymatic techniques. These techniques utilize specific antibodies as reporter molecules, which are particularly useful due to their high degree of specificity for attaching to a single molecular target. U.S. Pat. No. 4,568,649 describes ligand detection systems, which employ scintillation counting. These techniques are particularly useful for protein or modified protein parameters or epitopes, or carbohydrate determinants. Cell readouts for proteins and other cell determinants can be obtained using fluorescent or otherwise tagged reporter molecules. Cell based ELISA or related non-enzymatic or fluorescence-based methods enable measurement of cell surface parameters and secreted parameters. Capture ELISA and related non-enzymatic methods usually employ two specific antibodies or reporter molecules and are useful for measuring parameters in solution. Flow cytometry methods are useful for measuring cell surface and intracellular parameters, as well as shape change and granularity and for analyses of beads used as antibody- or probe-linked reagents. Readouts from such assays may be the mean fluorescence associated with individual fluorescent antibody-detected cell surface molecules, or the average fluorescence intensity, the median fluorescence intensity, the variance in fluorescence intensity, or some relationship among these.

As an example, Luminex beads or other fluorescent beads, or beads varying in light scattering parameters can be conjugated to antibodies or other parameters, or conjugated to protein receptors for parameters. The conjugated beads are added to the cells, cell lysate, or to the removed supernatant, allowing bead binding to target parameters. Also, fluorescent antibody to a distinct epitope of the target parameter is used to measure the level of target parameter bound. The fluorescence and light scatter characteristics of the beads constitute an identifier of the target parameter, and fluorescence derived from added antibody to the target parameter is an indication of the quantity of target parameter bound, and hence a readout of the individual parameter.

Flow cytometry may be used to quantitate parameters such as the presence of cell surface proteins or conformational or posttranslational modification thereof; intracellular or secreted protein, where permeabilization allows antibody (or probe) access, and the like. Flow cytometry methods are known in the art, and described in the following: Flow Cytometry and Cell Storing (Springer Lab Manual), Radbruch, Ed., Springer Verlag, 2000; Ormerod, Flow Cytometry, Springer Verlag, 1999; Flow Cytometry Protocols (Methods in Molecular Biology, No 91), Jaroszeski and Heller, Eds., Humana Press, 1998; Current Protocols in Cytometry, Robinson et al., eds, John Wiley & Sons, New York, N.Y., 2000. The readouts of selected parameters are capable of being read simultaneously, or in sequence during a single analysis, as for example through the use of fluorescent antibodies to cell surface molecules. As an example, these can be tagged with different fluorochromes, fluorescent bead, tags, e.g. quantum dots, etc., allowing analysis of up to 4 or more fluorescent colors simultaneously by flow cytometry. Plug-flow flow cytometry that has the potential to automate the delivery of small samples from unpressurized sources at rates compatible with many screening and assay applications, may allow higher throughput, compatible with high throughput screening, Edwards et al. (1999) Cytometry 37:156-9.

Both single cell multiparameter and multicell multiparameter multiplex assays, where input cell types are identified and parameters are read by quantitative imaging and fluorescence and confocal microscopy are used in the art, see Confocal Microscopy Methods and Protocols (Methods in Molecular Biology Vol. 122.) Paddock, Ed., Humana Press, 1998. These methods are described in U.S. Pat. No. 5,989,833 issued Nov. 23, 1999.

The quantitation of nucleic acids, especially messenger RNAs, is also of interest as a parameter. These can be measured by hybridization techniques that depend on the sequence of nucleic acid nucleotides. Techniques include polymerase chain reaction methods as well as gene array techniques. See Current Protocols in Molecular Biology, Ausubel et al., eds, John Wiley & Sons, New York, N.Y., 2000; Freeman, et al. (0.1999) Biotechniques 26(1):112-225, Kawamoto et al. (1999) Genome Res 9(12):1305-12; and Chen et al. (1998)Genomics 51(3):313-24, for examples.

Identifiers of individual cells, for example different cell types or cell type variants, may be fluorescent, as for example labeling of different unit cell types with different levels of a fluorescent compound, and the like. If two cell types are to be mixed, one may be labeled and the other not. If three or more are to be included, each may be labeled to different levels of fluorescence by incubation with different concentrations of a labeling compound, or for different times. As identifiers of large numbers of cells, a matrix of fluorescence labeling intensities of two or more different fluorescent colors may be used, such that the number of distinct unit cell types that are identified is a number of fluorescent levels of one color, e.g., carboxyfluorescein succinimidyl ester (CFSE), times the number of fluorescence levels employed of the second color, e.g. tetramethylrhodamine isothiocyanate (TRITC), or the like, times the number of levels of a third color, etc. Alternatively, intrinsic light scattering properties of the different cell types, or characteristics of the BioMAPs of the test parameters included in the analysis, can be used in addition to or in place of fluorescent labels as unit cell type identifiers.

Data Analysis

The comparison of a BioMAP obtained from a test genetic agent, and a reference BioMAP(s) is accomplished by the use of suitable deduction protocols, AI systems, statistical comparisons, etc. Preferably, the BioMAP is compared with a database of reference BioMAPs. Similarity to reference BioMAPs induced by assay combinations involving known pathway stimuli or inhibitors can provide an initial indication of the cellular pathways targeted or altered by the test genetic agent.

A database of reference BioMAPs can be compiled. These databases may include reference BioMAPs from panels that include known genetic agents or combinations of genetic agents that target specific pathways, as well as references from the analysis of cells treated under environmental conditions in which single or multiple environmental conditions or parameters are removed or specifically altered. In this way, a database is developed that can reveal the contributions of individual pathways to a complex response.

The effectiveness of pattern search algorithms in classifying BioMAPs can involve the optimization of the number of parameters and assay combinations. The disclosed techniques for selection of parameters provide for computational requirements resulting in physiologically relevant outputs. Moreover, these techniques for pre-filtering data sets (or potential data sets) using cell activity and disease-relevant biological information improve the likelihood that the outputs returned from database searches will be relevant to predicting gene expression product mechanisms and when of interest in vivo agent effects.

For the development of an expert system for classification of genetic agents, the following procedures are employed. For every reference and test pattern, typically a data matrix is generated, where each point of the data matrix corresponds to a readout from a parameter, where data for each parameter may come from replicate determinations, e.g. multiple individual cells of the same type. As previously described a data point may be quantitative, semi-quantitative, or qualitative, depending on the nature of the parameter.

The readout may be a mean, average, median or the variance or other statistically or mathematically derived value associated with the measurement. The parameter readout information may be further refined by direct comparison with the corresponding reference readout. The absolute values obtained for each parameter under identical conditions will display a variability that is inherent in live biological systems and also reflects individual cellular variability as well as the variability inherent between individuals.

Classification rules are constructed from sets of training data (i.e. data matrices) obtained from multiple repeated experiments. Classification rules are selected as correctly identifying repeated reference patterns and successfully distinguishing distinct reference patterns. Classification rule-learning algorithms may include decision tree methods, statistical methods, naive Bayesian algorithms, and the like.

A knowledge database will be of sufficient complexity to permit novel test BioMAPs to be effectively identified and classified. Several approaches for generating a sufficiently encompassing set of classification patterns and sufficiently powerful mathematical/statistical methods for discriminating between them can accomplish this.

A database can be compiled by preparing BioMAPs using different combinations of a plurality of biologically active factors, in conjunction with BioMAPs involving the use of genetically modified cells, where the genetic modification affects one or more of the pathways affected by one or more of the factors used to create the phenotype. The biologically active factors will usually be selected to influence a pathway that is of interest in its relationship to a pathway that the overexpressed protein is believed to affect. Usually, the cells employed will not have been subject to genetic modification except for the modification providing the expression construct of the gene of interest. However, once the pathway(s) for the gene of interest is determined, there may well be an interest in determining the effect of inhibiting or enhancing other pathways where the gene of interest is being overexpressed. The extent of the database associated with assay combinations to screen candidates for specific phenotypes, e.g. indications, will vary with the nature of the phenotype, the amount of information desired, the complexity of the system, and the like.

As indicated, genetic agents may be analyzed in the absence of any factors or with a limited number of factors. The assay is performed as previously described and the values of the parameters can be compared to the BioMAP reflecting the values for the parameters of the physiologic state of interest, the values of the parameters for the response to one or more factors, and the basal response. In this way, the effect of the genetic agent under physiological conditions can be evaluated. Similarly, one may have datasets compiled from combinations of genetic agents to determine their effect when combined on cell physiology. Again, with a comparison of the values obtained for the parameters with the values obtained from the parameters with assay combinations employing factors, one can evaluate the effect of the genetic agent combination on various cells in vivo.

A preferred knowledge database contains reference BioMAPs comprising data from optimized panels of cells, environments and parameters. For complex environments, data reflecting small variations in the environment may also be included in the knowledge database, e.g. environments where one or more factors or cell types of interest are excluded or included or quantitatively altered in, for example, concentration or time of exposure, etc.

Pathway Discrimination

BioMAPs are useful for pathway discrimination where the BioMAPs associated with genetic agents that have a common target and mode of action are reproducibly and robustly similar, where BioMAPs are associated with genetic agents that stimulate or inhibit different pathways of interest reproducibly, and with BioMAPs that discriminate a plurality of different pathways in a common set of assay combinations.

A pathway may be defined for the purposes of the invention as a set of interacting cellular events that produces or contributes to a specific phenotype. Pathways are mediated by sets of interacting molecules of the cell. Variables that act on the same cellular pathway result in similar BioMAPs. Similarly, variables that act on different cellular pathways result in different BioMAPs. Variables that act on multiple pathways can stimulate pathway interactions and thus also yield distinctive BioMAPs.

Comparison of a BioMAP produced by the action of a genetic agent to BioMAPs in the database will indicate whether-the variable yields a cellular state similar to those generated by other conditions, and thus may indicate a mechanism of action in the cell, and/or may indicate specific relevance of the biological activity to a particular state.

Optimization Techniques

Optimized assay combinations can be developed by repeating the procedure of testing parameter readouts in response to stimuli until the selected environment is sufficiently differentiated from the normal or another selected condition and an optimized parameter set is selected.

Optimization of an initial assay combination includes the identification of optimal concentrations of added biologically active factors, the timing of their addition, addition or deletion of factors, and selection of an optimal time course. The time course will depend upon whether one is interested in the effect of a genetic agent prior to the addition or at the time of the addition of the factors influencing the parameters or after the physiological condition has been established, as well as having cells that do and do not present the physiologic condition. The factors may have been present from about 0 to 72 h or longer prior to the addition of the transformation with the genetic agent, usually from about 0 to 48 h, and frequently from about 0 to 24 h. Where the cells may be at various stages of the physiologic condition, e.g. unchanged, intermediate stage and final stage, the factors will usually have been present from about 2 to 48 h or longer, more usually from about 6 to 24 h. Optimization also includes modification of the basal medium (e.g. the addition or removal of particular growth factors, extracellular matrix components etc.) to reflect differences between physiologic states of interest.

For the most part, the concentration of the factors for providing the physiologic condition will be known and frequently the response will not be sensitive to small changes in the concentration. Where the concentration has not been reported, one can determine a useful concentration by determining the concentration that provides saturation. This can be achieved using cells and titrating the number of receptors with a labeled factor, e.g. fluorescently labeled factor. Once the saturation level is known, one may cut back to about 25 to 75% of the saturation value and determine the response by analyzing for the parameters of interest and the effect of the reduced concentration as compared to the response at saturation. Alternatively, the factor may be taken to a plateau of a dependent functional response, and more or less added to define levels maximal to response measures.

Active compounds alter the cellular responses and readout patterns when included in a selected assay combination. Such alteration may include returning the levels of one or more parameters to their levels in the basal condition, or otherwise altering the cellular responses, particularly when such alterations reflect changes towards a desirable cellular state (e.g. converting Th1-like to Th2-like response, or vice versa).

Cell Families

Endothelial Cells

As exemplary of the subject situation, primary endothelial cells are employed in one embodiment of the invention, as these cells respond to a large variety of cellular stimuli. Endothelial cells are highly sensitive to their environment, and they contain a large number of signaling pathways. This provides an opportunity to evaluate the effect of genetic agents on many pathways and/or pathway interactions. Endothelial cells participate in many disease processes. In inflammation, they control the migration and localization of effector leukocytes and lymphocytes; in cancer, they control the nutrition of tumors and dissemination of metastases; and their dysregulation is centrally important to cardiovascular disease. The members of these pathways associated with particular stages are therefore important in understanding the contours of the pathway and the role of the players in the pathway.

The present invention is useful for identifying regulators of inflammation using human endothelial cells as an indicator cell type. Endothelial cells are found in inflammatory tissues; they are highly responsive to environmental stimuli; and they are a cell type for which primary cells can be readily isolated and cultured such that they retain responsiveness to many of the biologically active factors important to inflammatory and other processes. Vascular endothelial cells are a preferred cell type because they participate in the inflammatory disease process by regulating the type of leukocytes that are recruited to the target tissue. The specificity of recruitment is determined by the combinatorial expression of adhesion molecules and chemokines. A set of culture systems or assay combinations that mimic the response of the endothelial cells to different types of inflammatory processes have been developed in vitro using the methods of the invention.

A number of factors are known to be associated with endothelial cells, such as EGF, FGF, VEGF, insulin, etc., cytokines, such as the interleukins, including IL-1 IL-3, IL-4, IL-8 and IL-13; interferons; including IFN-alpha, IFN-beta, IFN-gamma; chemokines; TNF-alpha, TGF-beta, proangiogenic and anti-angiogenic factors, etc. (See Current Protocols in Immunology, supra).

Endothelial cells in inflammatory tissues from chronic inflammatory disease patients differ from endothelial cells in normal tissues by increased expression parameters including ICAM-1, E-selectin, IL-8 and HLA-DR [Nakamura S, Lab Invest 1993, 69:77-85; Geboes K, Gastroenterology 1992, 103:439-47; Mazzucchelli L, J Pathol 1996, 178:201-6]. In addition, each of these parameters has been demonstrated to function in the inflammatory disease process. ICAM-1 and E-selectin are cell adhesion molecules that contribute to the localization and activity of inflammatory cells including T cells, monocytes, and neutrophils. IL-8 is a neutrophil chemoattractant and HLA-DR participates in the activity of pathologic T cells. Other cell surface or secreted parameters include parameters that are known to be regulated by factors, such as VCAM-1, which is induced on endothelial cells by TNF-alpha or IFN-gamma; IL-10 and MIG which are induced on endothelial cells by IFN-gamma; or GRO-alpha or ENA-78 which are induced on endothelial cells by IL-1 and/or TNF-alpha [Goebeler M, J Invest Dermatol 1997, 108:445-51; Piali L Eur J Immunol. 1998, 28:961-72].

For assay combinations representative of chronic inflammatory diseases, the cytokine IL-1 is often found in combination with TNF-alpha and IFN-gamma in such diseases, for example, in Crohn's disease (Autschbach, 1995, Virchows Arch. 426:51-60). For this inflammation model of endothelial cells, an inhibitor of TNF-alpha, such as a neutralizing antibody against TNF-alpha, provides an example of an active compound. Adding anti-TNF-alpha to the assay combination was shown in reduced expression levels of ICAM-1; VCAM-1; and E-selectin; and increased expression levels of CD31.

Assay combinations that include genetically modified cells are also a preferred source of reference patterns. For example, TNF-alpha signaling in HUVEC involves the NFκB signaling pathway (Collins, 1995, Faseb J, 9:899). Blockade of this pathway can be accomplished by over expression of IκB, for example, through adenoviral gene transfer (Weber, 1999, Blood 93:3685). HUVEC overexpressing IkB-alpha express reduced levels of ICAM-1 or E-selectin in response to TNF-alpha. However, because other cytokines, such as IL-1, can also signal through NFκB, readout patterns due to TNF-alpha inhibition can be distinguished from readout patterns that reflect NFκB inhibition. By having blockades at a particular position in the pathway, over expression of a gene in the pathway without an effect indicates that the product of the gene acts prior to the blockade, while observing an effect indicates that the product of the gene acts after the blockade.

Leukocytes

By a similar iterative process as that described above, appropriate assay, combinations for endothelial cells representing other inflammatory, disease, or physiologic states are established. These conditions include: psoriasis, rheumatoid arthritis, or chronic Th2 disease environments such as asthma, allergy or ulcerative colitis. A chronic Th2 assay combination can be defined by the culture of HUVEC with TNF-alpha and/or IL-1 and IL-4 for 24 hours. Inflammation in chronic Th2 environments, such as asthma, is characterized by the presence of TNF-alpha, IL-1 and IL-4, but not IFN-gamma (Robinson, 1993, J. Allergy Clin. Immunol. 92:313). HUVEC cultured for 24 hours with TNF-alpha and IL-4 express high levels of VCAM and MCP-1, similar to the in vivo situation (Ohkawarea, 1995, Am J. Resp. Cell Mol. Biol. 12:4; Rozyk, 1997, Immunol. Lett. 58:47).

Lymphokine-producing activated lymphocytes (CD45RO+, CD44hi, etc.) are a hallmark of inflammatory diseases including psoriasis, rheumatoid arthritis, Crohn's disease, ulcerative colitis, asthma, etc. Depending on the disease environment and tissue site, activated lymphocytes can differ in their expression and function of adhesion molecules and other receptors, as well as in their production of various cytokines and other factors.

Specific homing and adhesion receptors, as well as chemokine receptors, expressed by lymphocytes differentiating into effector and memory cells target the involved regulatory and cytotoxic T cell populations, as well as B cells responsible for humoral immunity. Upregulation and modulation of homing receptor expression patterns is observed when lymphocytes are activated in defined microenvironments comprising specific cytokines; and in some environments multiple homing receptors (e.g., alpha4beta7, the cutaneous lymphocyte antigen ("CLA"), inflammatory chemokine receptor such as CCR5 and CXCR3 and bonzo, etc.) are induced. Multiplex analysis of each of these homing receptor parameters, which may also be performed in conjunction with other known or discovered parameters in reflecting the cellular state of activation, can be used to identify the role that a gene product may play in the various diseases and whether such gene product may be a target for the treatment of the disease.

The assay conditions for these cells include (1) known activation conditions ((combinations of anti-CD3+IL-2+/−IL-4+/−IFN-gamma (+/−IL-12+/−anti-IL-4 or anti-IFN-gamma. Such conditions are given in: T Cell Protocols: Development and Activation. (Methods in Molecular Biology, 134), Kearse, Ed., Humana Press, 2000.); (2) culture conditions that represent in vivo disease environments; or (3) conditions that emphasize or discriminate known signaling pathways or specific signaling pathways implicated in disease states. Assay combinations and reference BioMAPs are identified for a variety of diseases, including psoriasis; arthritis, Crohn's disease, ulcerative colitis, asthma, etc: by the iterative process as described in Example 1, of defining environmental conditions and initial parameter sets from in vivo data, testing assay combinations in vitro, comparing the in vitro and in vivo BioMAPs, optimizing the assay combination and selection of an optimal parameter set.

The disease environment in psoriasis includes IL-12, IFN-gamma (and TNF-alpha (Yawalker, 1998, J. Invest. Dermatol. 111:1053; Austin, 1999, J. Invest. Dermatol. 113:752), therefore an assay combination for psoriasis will include one or more, usually at least two, and frequently all of these factors. Inflammatory T cells in psoriasis express high levels of the CLA antigen, a carbohydrate antigen related to Sialyl Lewis x (Berg, 1991, J. Exp. Med. 174: 1461; Picker, 1990, Am. J. Pathol. 136:1053). Therefore a parameter set for psoriasis will contain the CLA antigen.

The disease environment in Crohn's disease includes IL-1, TNF-alpha, IL-6, IL-8, IL-12, IL-18, and IFN-gamma (Daig, 1996; Woywodt, 1994; Kakazu, 1999; Pizarro, 1999; Monteleone, 1999), therefore an assay combination for Crohn's disease will include one or more of these factors, generally including at least two of the IL factors, by themselves or in combination with at least one of IFN-gamma and TNF-alpha. T cells in inflammatory bowel disease express high levels of the alphaEbeta7 integrin (Elewaut, 1998, Scand J. Gastroenterol, 33:743), therefore the parameter set for inflammatory bowel diseases preferentially contains alphaEbeta7.

The disease environment in rheumatoid arthritis includes TNF-alpha, IL-1, IL-6, IL-10, IL-15, MIP1alpha, MCP-1, and TGF-beta (Robinson, 1995, Clin. Exp. Immunol. 101: 398; Thurkow, 1997, J. Pathol. 181:444; Suzuki, 1999, Int. Immunol, 11:553), therefore an assay combination for arthritis will include one or more of these factors, generally including at least two of the IL factors and at least one of MIP1 and MCP-1. T cells in rheumatoid arthritis synovial fluid express CCR5 and CXCR3 (Suzuki, 1999; Qin, 1998, J. Clin. Invest. 101:746; Loetscher, 1998, Nature 391:344), therefore the parameter set for rheumatoid arthritis preferentially contains CCR5 and CXCR3.

The disease environment in asthma includes IL-1alpha, IL-4, IL-5, IL-6 and GM-CSF (Miadonna, 1997; Walker, 1994), therefore, an assay combination for asthma will contain one or more of these factors, generally including at least two of the IL factors and GM-CSF.

Once the optimal environmental conditions representing the target disease are determined, cells are treated with the genetic agent in those environments and the selected parameters are measured. Comparing the BioMAPs obtained, in the presence of over expression, with reference BioMAPs enables the identification of proteins that; are involved in the lymphocyte responses to complex environments, and identifies the protein as acting in a selective pathway. Reference BioMAPs can be generated in the presence of genetic constructs or other agents that selectively target, stimulate, inhibit or otherwise modulate specific pathways. In this way, a database of reference BioMAPs is developed. One preferential application of the invention is in immune deviation. Certain inflammatory diseases result or are exacerbated by polarization of an inflammatory response towards Th1 or Th2. For example, conditions that promote Th1 responses (e.g. systemic treatment with IFN-gamma) exacerbate certain diseases such as multiple sclerosis. By the procedure given above, compounds can be screened for their ability to shift BioMAPs from "Thi" to "Th2", vice versa, or from "Th1" or "Th2" to other phenotypes.

Macrophage

The present invention can be applied to the identification of genetic agents that inhibit or alter macrophage activation. Peripheral blood monocytes, tissue macrophages and related cell lines are a preferred cell type for screening for pharmacologically active compounds/interventions due to their ability to discriminate pathophysiological environments. Monocytes/macrophages in different physiological settings have altered responses. IL-4 reduces production of IL-10 in LPS stimulated blood monocytes but not in synovial monocyte/macrophages (Bonder (1999) Immunol. 96:529; Ju (1999) Int. Rev. Immunol. 18:485). In addition to being highly responsive to their environment, monocytes/macrophages participate in a variety of disease processes, including inflammation, fibrosis, and wound healing, through their production of mediators, growth factors, phagocytosis and antigen presentation functions. Assay combinations, e.g. IL-4 and other IL factors, M-CSF, and GM-CSF are used in combination with each other or other factors associated with the physiologic or disease environments of interest and readout parameter sets are selected that allow different states to be distinguished. Readout parameters include integrins, adhesion molecules, and the like. Factors are added to selected assay combinations, parameters are measured and the resulting test patterns are compared to reference BioMAPs. Reference patterns, held in a knowledge database include those developed from the analysis of cells treated under environmental conditions in which single components are removed, or with known drugs that target specific pathways. Alternatively, reference BioMAPs can be generated in the presence of genetic constructs that selectively target, stimulate, inhibit or otherwise modulate specific pathways. In this way, a database of reference BioMAPs is developed, and genetic agents are identified by their ability to produce a desired BioMAP as indicative of participating in a pathway(s).

Mast Cell

The present invention can be applied to the identification of genetic agents that inhibit or alter mast cell activation. The products of such genetic agents may have utility as targets in the treatment of allergy and asthma, where mast cell products mediate disease pathology (Galli, 2000, Curr. Opin. Hematol. 7:32). Mast cells display altered responses depending on their environment. The ability of mast cells to produce IL-3 and GM-CSF is significantly increased in the presence of fibronectin or vitronectin (Kruger-Krasagakes, 1999, Immunology, 98:253). Mast cells in allergen-induced late-phase cutaneous reactions in atopic patients express high levels of the high affinity IgE receptor compared with mast cells in control skin (Ying, 1998, Immunology 93:281). Assay combinations including at least one of fibronectin and vitronectin are developed that reflect physiologic or disease environments and readout parameter sets, including at least one of IL-3, GM-CSF, and IgE-receptor, are selected that allow different states to be distinguished. Reference BioMAPs can be generated in the presence of genetic constructs that selectively target, stimulate, inhibit or otherwise modulate specific pathways. In this way, a database of reference BioMAPs is developed, and role of a genetic construct is identified by its ability to produce a particular BioMAP.

Cancer Applications a. Targets for Cytolytic/Cytostatic Compounds

The subject invention can be used for identifying targets for anticancer agents and for contrasting the effect of over expression of a protein on a BioMAP as compared to the action of an anticancer drug. The unique comparisons between panels of cell types holds the potential to provide therapeutically important information, and allow subclassification, of genes that can alter neoplastic cell proliferation, alter the immunogenicity, or modulate other critical features for cancer therapy. A panel of 60 neoplastic cell lines at the NCI has been used to examine the effects of hundreds of anti-cancer and other compounds on neoplastic cell proliferation (Weinstein, 1997, Science 275:343) and these same cells can be used with genetic agents to determine the effect of expression of the genetic agent on the BioMAP of the cancer cells under selected conditions, e.g. absence of the genetic construct, presence of an anticancer agent, etc. The responses of any individual cell line may carry little, information about the role of the product of the genetic agent in the, same or different cancers from the same or different sources. However the patterns of responses among the 60 cells of the panel should provide a robust ability to distinguish the role of the genetic agent over a spectrum of different cancers, and thus to characterize the mechanisms of action of the genetic agent expression product.

In preparing BioMAPs, the responses of cell surface proteins and/or secreted products such as chemokines and other cytokines and the like, are determined under environmental conditions supportive of the neoplastic proliferative phenotype. Breast cancer environments involve certain growth factors, e.g. angiogenic factors and cytokines, such as IL-10 (Merendino 1999, 68, 355). Alterations in the selected parameters by contact of the cells with anti-cancer agents having known activity as to a target are used to define reference BioMAPs characteristic and diagnostic of mechanisms of action. The use of cell surface parameters to identify cytotoxic and cytostatic states allows a panel of cells to be evaluated in parallel. BioMAPs can be generated from known anti-cancer agents including DNA synthesis inhibitors, nucleoside analogs, topoisomerase inhibitors, microtubule function inhibitors etc. Such compounds are given in Weinstein, 1997, and The Pharmacologic Basis of Therapeutics. Reference patterns that distinguish compounds that are cytostatic or cytolytic versus apoptosis-inducing are developed using a panel of primary tumors and tumor cell lines with and without functioning p53 pathways. The procedure of simultaneous multiplex analyses of normal and cancer cell lines allows discrimination of the role of genetic agents in the neoplastic process.

b. Inhibitors of Metastatic Phenotype

The present invention can be applied to the identification of expression products that alter metastatic phenotypes of cancer cells. Metastatic cancers have altered adhesive and invasive functions. Metastatic cancers are associated with certain features including expression of various oncogenes, such as H-ras, increased levels of proteolytic enzymes, such as TPA (tissue plasminogen activator), production of osteopontin, and altered adhesion molecule expression and function. For example, carcinomas preferentially express alpha6beta1 and less alpha2beta1, alpha3beta1 and alpha5beta1 (Chambers 1993, Crit. Rev. Oncol. 4:95; Dedhar, 1995, Cancer Metastasis Rev. 14:165; Tuck, 1999, Oncogene 18:4237). Simultaneous multiplex analysis of normal and cancer cell lines allows discrimination of the genes that selectively modulate the metastatic phenotype.

c. Inducers of Differentiative Phenotypes.

There is a general inverse relationship between the degree of cellular differentiation and the rate of cell proliferation in tumors. Several anti-cancer agents stimulate, the differentiation and inhibit proliferation of malignant cells, including retinoids, various cytokines and analogs of vitamin D (Bollag, 1994, J. Cell Biochem. 56:427). All-trans retinoic acid, an agent that induces differentiation, gives a high rate of complete clinical remission in the treatment of acute promyelocytic leukemia (Tallman, 1994, Semin Hematol 31 (Suppl 5):38). By introducing over expression of a gene, the role of the gene in enhancing cell proliferation or differentiation can be analyzed. In addition, once the pathway is identified, by using chemical agents that are known to act on members of a pathway, the effect of such agents can be used to identify the position of the gene product in the pathway.

d. Apoptosis of Tumor Endothelial Cells.

The present invention can be applied to the identification of genetic agents that are in the pathway of apoptosis of tumor endothelial cells. For this application, environmental conditions that induce a tumor endothelial cell phenotype on cultured endothelial cells are selected. Typically these environments are proangiogenic and contain a variety of growth factors, such as TGF-beta, VEGF and basic FGF, as well as other tumor or other cell derived factors, where these factors can be used in the assay combination. Tumor endothelium differs from other endothelium by increased expression of alphaVbeta3. A set of conditions that induce apoptosis of these cells is evaluated and a set of parameters that defines a BioMAP diagnostic of apoptosis is identified. Apoptotic conditions are identified as those that induce DNA laddering, and other well described features. These include simple culture conditions that contain one or more factors known to induce or promote endothelial cell apoptosis in vitro, such as ceremide, the combination of TNF-alpha and heat shock or sodium arsenite, TNF-alpha+IFN-gamma, oxysterols; TNF-alpha in the presence of cyclohexamine, etc. (See Ruegg (1998) Nat. Med. 4:408).

Parameters that may be included in the selected set include a variety of molecules involved in adhesion and proteolysis (since a prominent feature of apoptotic endothelial cells is their release from the vessel wall), those that can be modulated by individual factors, such as E-selectin, ICAM-1, VCAM and HLA-DR, and molecules or determinants known to be modulated with apoptosis such as CD95, ICAM-1, CD44, and carbohydrate determinants (Herbst, 1999, J. Cell Physiol. 181:295; Rapaport, 1999, Glycobiology 9:1337; Hirano (1999) Blood; 93:2999; Thomas (1998) J. Immunol: 161:2195; Ma (1998) Eur. J. Hematol. 61:27; Pober (1998) Pathol. Biol. (Paris) 46:159).

Once a reference BioMAP for endothelial cell apoptosis is identified, a genetic construct can be screened for its ability to induce a similar BioMAP from tumor, but not normal, endothelial cells. Reference BioMAPs are generated in the presence of genetic constructs that selectively target specific pathways. In this way, a database of reference BioMAPs is developed that can reveal the contributions of individual pathways to a complex response and identify the role of a particular gene in a pathway.

Angiogenesis Inhibitors

The present invention can be applied to the identification of proteins that activate, inhibit or modulate angiogenesis. Pharmacologic modulation of angiogenesis has applications to the treatment of cancer, where vascularization of tumors contributes to cancer growth; for inflammatory conditions such as arthritis where neovascularization supports inflammatory cell influx; wound healing; and others. A number of biologically active agents are known to induce or promote angiogenesis including VEGF, FGF, IL-8, IL-4, various extracellular matrix components, etc., where at least 2, usually at least 3 of these factors may be used in an assay combination. Physiologically relevant states in vivo are complex, containing combinations of factors and other conditions. The environment of rheumatoid arthritis, in which angiogenic factors are present in a proinflammatory environment, can be distinguished from tumor environments that may be characterized by reduced oxygen and the presence of various growth factors in combination with a pro-angiogenic environment.

Culture environments for endothelial cells that reflect these disease or physiological environments are developed through an iterative process of (a) identifying factors known to be expressed at the disease site. For example, vascularizing arthritis environments contain basic FGF and VEGF in addition to TNF-alpha, IL-1, IL-6, IL-10, IL-15, MIP1$ and MCP-1 (Qu, 1995, Lab Invest., 73:339; Koch, J. Immunol. 1994, 152:4149; Robinson, 1995, Clin. Exp. Immunol. 101: 398; Thurkow, 1997, J. Pathol. 181:444; Suzuki, 1999, Int. Immunol, 11:553). The disease environments of highly vascularized tumors include hypoxia, VEGF, fibrinogen and TGF-β (Senger, 1994 Invasion Metastasis, 95:385; Shweiki, 1992, Nature, 359:843). The iterative process then (b) identifies a set of parameters that includes those that are known to be differentially regulated by one or more of the factors identified in (a), or parameters including adhesion molecules, receptors, chemokines, etc:, that are known to be differentially expressed by angiogenic endothelium at the disease sites. These may include the expression of functional forms of adhesion molecules such as alphaVbeta3, VCAM, proteases, such as matrix metalloproteinases, or other substances. The process then c) evaluates the effects of environments containing, combinations of factors on the expression of parameters on endothelial cells in vitro; and d) selects conditions (factor composition, time course, concentration, etc.) that result in the pattern of expression of parameters that is representative of the in vivo phenotype.

Optimization of the final set of environmental conditions and parameters is carried out by testing larger panels of parameters under the different environmental conditions in vitro and selecting those that can discriminate between two or more environments, said environments differing by one or more individual environmental components. This procedure can be performed in a high throughput manner, and individual selected parameters can be confirmed by evaluating the expression in vivo under normal and disease tissues. The goal of the above process is the identification and selection of a minimal set of parameters, each of which provides a robust readout, and that together enable discrimination of each environmental condition.

Once a panel of environments is identified, and an optimal set of parameters is selected, cells are treated under each condition and a database of reference BioMAPs is developed. These include reference BioMAPs from cells treated under environments that may include known drugs that target specific pathways, as well as reference BioMAPs from the analysis of cells treated under environmental conditions in which single or multiple components are removed. For example, for an assay combination representing endothelial cells in a vascularizing arthritis environment, reference BioMAPs are developed from assay combinations in which single components (e.g. VEGF) might be removed. Reference BioMAPs are also generated from cells containing genetic constructs that selectively target specific pathways. In this way, a database of reference BioMAPs is developed that can reveal the contributions of individual pathways to a complex response.

With such a database, the invention provides for preferential selection of drug compounds that inhibit angiogenic responses in complex environments. Such compounds would be identified by their ability to induce a BioMAP consistent with inhibition of an angiogenic phenotype in the presence of a complex environment. Compounds that selectively block the response to a single factor or component of the complex environment (e.g. FGF receptor signaling, etc.) would be revealed by a BioMAP consistent with the response pattern in the absence of that factor (e.g. FGF, etc.)

Modulators of Bone Development

Modulation of bone development and remodeling has application for the therapy of osteoporosis, atherosclerosis, and rheumatoid arthritis, all situations where undesired bone destruction, bone formation or morphogenesis occurs. Bone-forming osteoblasts are derived from a common precursor in bone marrow that differentiates into osteoblasts or adipocytes depending on the differentiation environment. Factors associated with osteoblast development include estrogen, bone morphogenic proteins and TGF-beta. Differentiation of osteoblasts is associated with the production of alkaline phosphatase, type I collagen, osteopontin and the ability to mineralize calcium. Factors associated with adipocyte development include FGF and glucocorticoids. Differentiation of adipocytes is associated with their production of PPARgamma2, lipoprotein lipase and leptin. Optimized culture environments are defined for the relevant disease or physiologic states as described above and a set of parameters that distinguish adipocyte and osteoblast differentiation are selected. For screening genes as modulators of osteoporosis, genes may be screened for their ability to promote osteoblast development in the relevant disease environment and the pathway(s) associated with this modulation. For example, in the case of older women, that would include low estrogen levels; in the case of autoimmune disease patients on long term glucocorticoid therapy, the environment may contain dexamethasone, and so on.

Modulation of osteoclast development and function has applications for bone remodeling that occurs in rheumatoid arthritis. Osteoclasts develop from CD14+ monocytes. Factors that promote osteoclast development include TRANCE (RANKL or osteoprotegrin ligand), TGF-beta and M-CSF. Rheumatoid arthritis environments also contain TNF-alpha, IL-1, IL-6, IL-10, IL-15, MIP1alpha and MCP-1 (Robinson, 1995, Clin. Exp. Immunol. 101:398; Thurkow, 1997, J. Pathol. 181:444; Suzuki, 1999, Int. Immunol, 11:553). Optimized culture environments are defined for osteoclasts or precursor CD14+ monocytes in pro-osteoclast development arthritis environment. A set of parameters is selected that identifies osteoclasts in such an environment. Osteoclast function is associated with expression of calcitonin, vitronectin receptors, cathepsis k, carbonic anhydrase II, vacuolar (H(+)) ATPase, tartrate-resistant ATPase and osteopontin.

Neurobiologyapplications

Alzheimer's Disease

A prominent feature of Alzheimer's disease patients is activated glia (astrocytes and microglia) in close proximity to amyloid plaques. These cells express increased levels of Class II antigens, alpha-1-antichymotrypsin, IL-1beta, S-100beta and butyrylcholinesterase. The disease environment in Alzheimer's disease contains IL-1, IL-6 and the alpha-amyloid peptide 1-42.

Regulators of Hematopoiesis

Mesenchymyl stem cell cultures can be provided with environments leading to fibroblastic, osteoblastic, or adipocyte differentiation, each associated with unique patterns of cell surface and secreted molecule expression defining these cellular states. A set of parameters that identifies various lineages of hematopoietic cells (e.g. erythroid, myeloid, T versus B, NK, etc.) are selected. Genes that alter the differentiation of selected cell types are selected by their ability to produce BioMAPs characteristic of that population.

Kits

For convenience, the systems of the subject invention may be provided in kits. The kits could include the appropriate additives for providing the simulation, optionally include the cells to be used, which may be frozen, refrigerated or treated in some other manner to maintain viability, reagents for measuring the parameters, and software for preparing the BioMAP. The factors will be selected that in conjunction with the cells would provide the desired physiological state simulating the in vivo situation. The factors could be a mixture in the appropriate proportions or provided individually. For example, IL-1, TNF-alpha, and IFN-gamma would be combined as a powder to be measured for addition to the cell medium and labeled antibodies to parameters, such as ICAM-1, VCAM-1 and E-selectin, in conjunction with second capture antibodies or using antibodies for homogeneous assays, where another reagent is present. The software will receive the results and create a BioMAP and can include data from other assay combinations for comparison. The software can also normalize the results with the results from a basal culture and/or the basal culture including the factors.

The following examples are put forth so as to provide those of ordinary skill in the art with a complete disclosure and description of how to make and use the subject invention, and are not intended to limit the scope of what is regarded as the invention. Efforts have been made to ensure accuracy with respect to the numbers used (e.g. amounts, temperature, concentrations, etc.) but some experimental errors and deviations should be allowed for. Unless otherwise indicated, parts are parts by weight, molecular weight is average molecular weight, and pressure is at or near atmospheric.

EXPERIMENTAL

Example 1

Regulators of Endothelial Cell Responses to Inflammation

The present invention is useful for identifying regulators of inflammation using human endothelial cells as an indicator cell type. A set of assay combinations that reproduces aspects of the response of the endothelial cells to different types of inflammatory processes is developed in vitro. While such methods are described with respect to analysis of chemical compounds, they are also applicable to testing of genetic agents.

Primary human umbilical vein endothelial cells (HUVEC) are used. Other cells that may replace HUVEC in the screen include primary microvascular endothelial cells, aortic or arteriolar endothelial cells or endothelial cell lines such as EAhy926 or E6-E7 4-5-2G cells or human telomerase reverse transcriptase-expressing endothelial cells (Simmons, J. Immunol., 148:267, 1992; Rhim, Carcinogenesis 19:673, 1998; Yang, J. Biol. Chem. 274:26141, 1999). $2 \times 10^4$ cells/ml are cultured to confluence in EGM-2 (Clonetics). Other media that may replace EGM-2 include EGM (Clonetics) and Ham's F12K medium supplemented with 0.1 mg/ml heparin and 0.03-0.05 mg/ml endothelial cell growth supplement (ECGS) and 10% FBS, or medium M199 (Life Technologies, Inc.) containing 20% fetal bovine serum and 2 ng/ml basic fibroblast growth factor (Jaffe, J. Clin. Invest. 52:2745,1973; Hoshi, PNAS 81:6413,1984).

The disease environment present in chronic inflammatory diseases, such as Crohn's disease, differs from the normal condition by increased presence of multiple biologically active agents including IL-1, TNF-α, and IFN-γ (Woywodt, 1994; Kakazu, 1999). Other biologically active agents that may be increased in chronic inflammatory disease environments include IL-4, IL-6, IL-8, IL-12, IL-13, IL-18, TGF-beta, and histamine, as well as activated leukocytes and their products (Daig, 1996, Gut 38:216; Woywodt, 1994, Eur. cytokine Netw. 5:387; Kakazu, 1999 Am J. Gastroenterol. 94:2149; Pizarro, 1999, J. Immunol. 162:6829; Monteleone, 1999, J. Immunol. 163:143; McClane, 1999 J Parenter Enteral Nutr 23:S20; Beck, 1999, Inflam. Bowel Dis. 5:44).

Optimized assay combinations will contain at least two, and preferably three, four or more of these biologically active agents. Concentrations of agents are standard according to, the literature, typically at physiologic concentrations. Concentrations may also be determined experimentally as the amount required to saturate the relevant receptor. A useful feature of the present invention is that combinatorial effects of multiple factors are observed over wide ranges of factor concentrations. Based on the factors included in an assay combination, a set of parameters for including in a biomap are selected.

Selection of parameters is based on the following factors: 1) parameters that are modulated in vivo in the disease environment or condition; 2) parameters that are modulated by one of the components in the assay combination; 3) parameters that are modulated by more than one of the components in the assay combination; 4) parameters that are modulated by the combined action of two or more components in the assay combination; 5) parameters that participate in the disease process, such as validated disease targets; 6) cell surface and secreted molecules. Preferred parameters are functional and are downstream within signaling pathways, so as to provide information on effects of multiple pathways. For assay combinations containing the factors TNFα, IFN-γ and IL-1, parameters examined and chosen by these criteria include ICAM-1 (CD54), VCAM-1 (CD106), E-selectin (CD62E), IL-8, HLA-DR and MIG (CLCX9). Other parameters of interest for including in a Biomap include: IP-10, Eotaxin-1, Eotaxin-3, MCP-1, RANTES, Tarc, CD31, alphavbeta3, and P-selectin (CD62P). Parameters examined but not selected include: CD34, CD40, CD9, CXCR2, CD95, fibronectin, HLA-ABC, GROalpha, MCP-4, TAPA-1, alphaVbeta5, VE-Cadherin, CD44, von Willebrand factor, CD141, 142, 143, and CD151.

Parameters are not selected for inclusion in a biomap for the following reasons: redundancy, function of parameter is not associated with disease pathology, function is upstream in a signaling pathway, parameter is not modulated in response to factors, modulation is not robust or reproducible. Cell death in inflammation, involved for example in cellular remodeling in healing, as well as the consequences of toxicity, involves apoptosis. Parameters of interest also include parameters indicative of cell damage and apoptosis including released cytoplasmic lactate dehydrogenase (LDH) or mitochondrial cytochrome c, appearance of APQ2.7 epitope or active caspase-3 (Zhang, J. Immunol., 157:3980, 1996; Bussing, Cytometry 37:133, 1999). Parameters indicative of cell proliferation are also of interest and include Ki-67 and PCNA (Landberg, Cytometry, 13:230, 1992).

Strategies for optimizing the parameter set include: selecting only one of any group of parameters that are co-regulated under all assay combinations; preferentially selecting parameters that are functionally relevant to the disease process; preferentially selecting parameters that give robust and reproducible results in multiple assays, or reflect cellular toxicity etc. In the present example, whereas both IP-10 and MIG are co-regulated under the assay conditions described, detection of MIG by the cell-based ELISA as described above is more robust, therefore MIG was preferentially included in the optimized set of parameters. For parameter set optimization, additional parameters may be added to the initial parameter set to distinguish assay combinations that result in cellular de-adhesion, toxicity or other activity. Microscopic observation can identify cellular de-adhesion, while release of cytoplasmic substances, such as lactate dehydrogenase, can be measured as an indication of toxicity. For example, CD31 is an endothelial cell adhesion molecule that participates in cell-cell adhesion and complete loss of CD31 expression in an assay indicates loss of cells from the plate. Therefore, CD31 is a useful parameter for monitoring cellular de-adhesion.

Figure 1B:
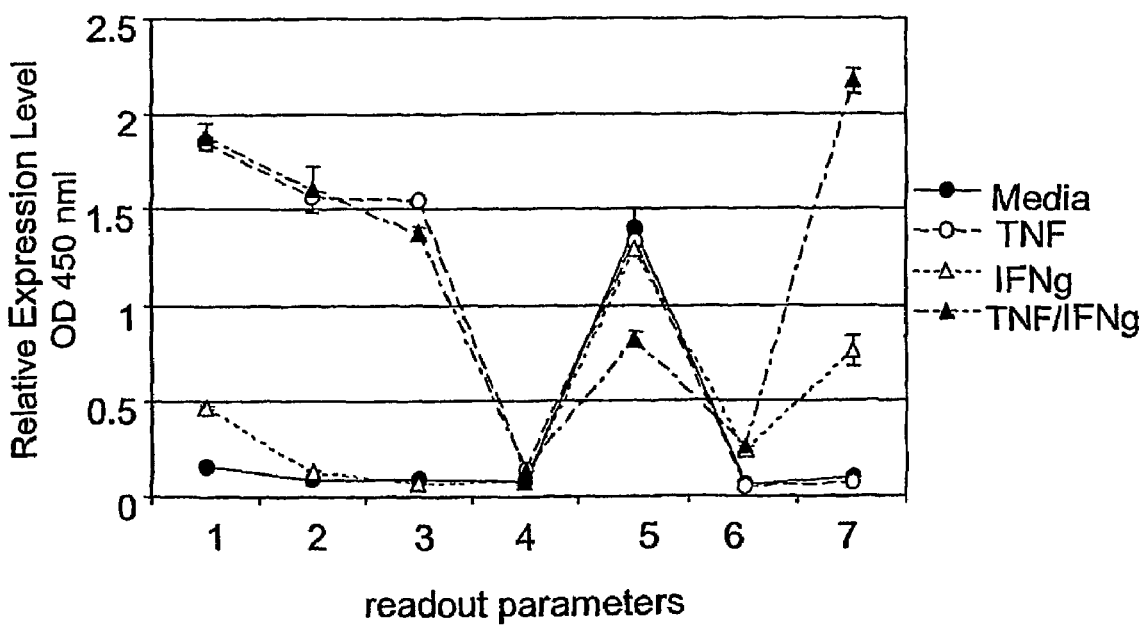
Figure 1C:
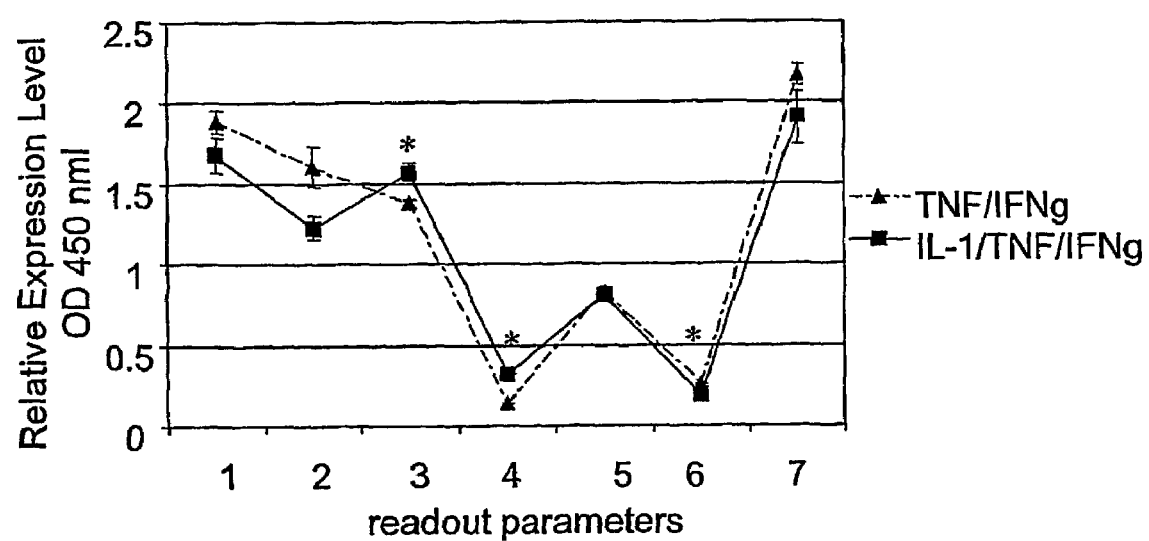

The data provided in FIGS. 1A-1C illustrate the usefulness of the present invention in compound screening applications. FIG. 1A shows the readout patterns from confluent cultures of HUVEC incubated with either of TNF-α (5 ng/ml), IFN-γ (100 ng/ml) or IL-1 (1 ng/ml) or basal medium for 24 hours. After 24 hours, cultures are washed and evaluated for the presence of the parameters ICAM-1 (1), VCAM-1 (2), E-selectin (3), IL-8 (4), CD31 (5), HLA-DR (6) and MIG (7) by cell-based ELISA as described (Melrose, J. Immunol. 161:2457, 1998). For this, plates are blocked with 1% Blotto for 1 hr, and treated with primary antibodies (obtained from Pharmingen and Becton Dickinson) at 1 ng/ml for 2 hr. After washing, secondary peroxidase-conjugated anti-mouse IgG antibody (Promega) at 1:2500 is applied for 45 min. After washing, TMB substrate (Kierkegaard & Perry) is added and color developed. Development is stopped by addition of $H_2SO_4$ and the absorbance at 450 nm (subtracting the background absorbance at 600 nm) is read with a Molecular Dynamics plate reader. The relative expression levels of each parameter are indicated by the OD at 450 nm shown along the y-axis. The mean +/−SD from triplicate samples is shown. The assay combinations are useful in screening compounds that modulate TNF-α, IL-1 and IFN-γ signaling pathways, however, compounds must be evaluated separately in all three assay combinations to identify compounds that selectively modulate one or more of these pathways. In addition, compounds that selectively modulate combinatorial effects of these pathways cannot be distinguished.

FIG. 1B shows the readout patterns from confluent cultures of HUVEC cells treated with TNF-α (5 ng/ml), IFN-γ (100 ng/ml), TNF-α (5 ng/ml)+IFN-γ (100 ng/ml) or base media. After 24 hours, cultures are washed and evaluated for the presence of the parameters ICAM-1 (1), VCAM-1 (2), E-selectin (3), IL-8 (4), CD31 (5), HLA-DR (6) and MIG (7) by cell-based ELISA performed as described above, and are reported as the OD at 450 nm. The mean +/−SD from triplicate samples are shown. * indicates p<0.05 comparing results obtained with the two separate conditions. HUVEC cultured with TNF-α for 24 hours express increased levels of cell surface ICAM-1, VCAM-1, and E-selectin as measured by cell-based ELISA. HUVEC cultured with IFN-γ for 24 hours express increased levels of ICAM-1, HLA-DR and MIG. HUVEC cultured in the presence of both TNF-α and IFN-γ for 24 hours produce a combined phenotype where HUVEC express increased levels of ICAM-1, VCAM-1, E-selectin, HLA-DR and MIG. This phenotype is more similar to the in vivo phenotype of endothelial cells in chronic inflammation and moreover reflects the stimulation of two different known pathways of interest in regulation of inflammatory processes. Concentrations of TNF-α and IFN-γ employed and length of exposure are standard according to the literature. Concentrations and exposure length are also tested experimentally and conditions chosen to achieve an endothelial cell phenotype displaying multiple features of endothelial cells in chronic inflammatory diseases (e.g increased expression of ICAM-1, VCAM-1, E-selectin as well as HLA-DR and MIG).

A particularly useful feature of the invention is that the combined phenotype is observed over a wide range of concentrations of the individual biologically active factors. The results in FIG. 1C demonstrate how an assay combination containing both TNF-α and IFN-γ is useful in screening for compounds that block either the TNF-α or IFN-γ signaling pathways, and furthermore, can be used to distinguish compounds that modulate combinatorial effects of these pathways.

Figures 2A, 2B:
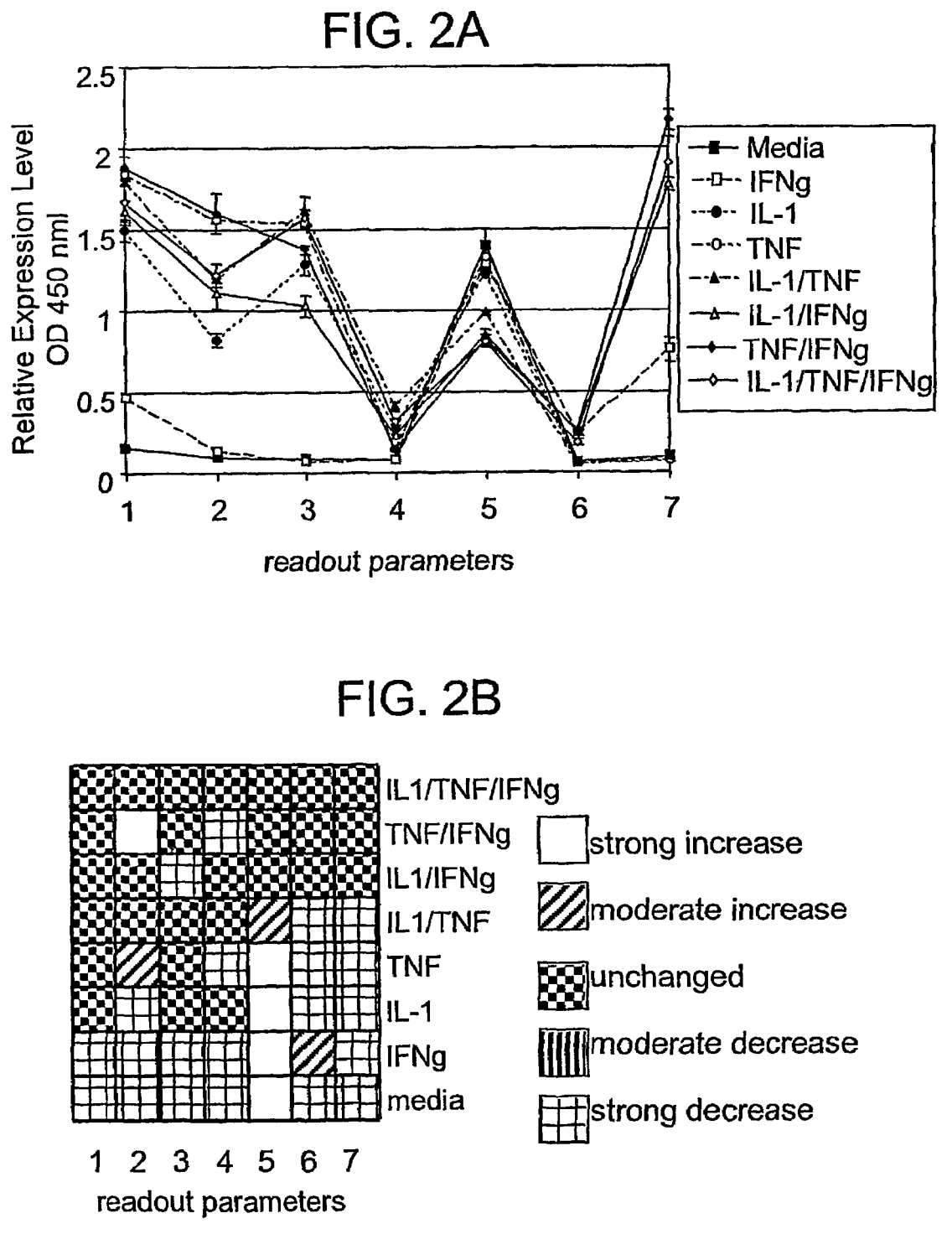

Inclusion of additional biologically active factors further improves the usefulness of the screens provided in the present invention. FIG. 2A shows the readout patterns from confluent cultures of HUVEC cells treated with TNF-α (5 ng/ml)+IFN-γ (100 ng/ml) or TNF-α (5 ng/ml)+IFN-γ (100 ng/ml)+IL-1 (1 ng/ml). After 24 hours, cultures are washed and evaluated for the presence of the parameters ICAM-1 (1), VCAM-1 (2), E-selectin (3), IL-8 (4), CD31 (5), HLA-DR (6) and MIG (7) by cell-based ELISA performed as described above, and are reported as the OD at 450 nm. The mean +/−SD from triplicate samples are shown. * indicates p<0.05 comparing results obtained with the two separate conditions. Addition of IL-1 to the assay combination containing TNF-α and IFN-γ results in increased levels of E-selectin and IL-8, in addition to the increased levels of ICAM-1 VCAM-1, HLA-DR and MIG. E-selectin and IL-8 are particularly correlated with disease stage in chronic inflammatory diseases, including inflammatory bowel disease. Thus an assay combination containing IL-1, TNF-α and IFN-γ represents an optimized assay combination. This assay combination is useful for screening for compounds that modulate aspects of IL-1, TNF-α or IFN-γ signaling pathways. In particular, it provides a useful screen for selecting compounds that are active when a particular target pathway may be modified by the activity of other pathways or when the target is not known.

One or more of IL-4, IL-6, IL-8, IL-12, IL-13, IL-18, TGFbeta, and histamine are applied; and/or neutralizing antibodies to autocrine factors such as IL-6, IL-1 and IL-8. Standard concentrations of agents are employed as described in the literature. Based on the factors selected, a set of parameters for including in a biomap is selected.

Database of readout response patterns. A database of reference biomaps is compiled for the optimized assay combination and parameter set of the examples described in FIG. 2A. These reference biomaps are developed from assay combinations in which specific modifications of the optimized assay combination are made. These modifications included: 1) elimination of one or more assay combination components, 2) addition of compounds or interventions to the assay combination. Biological responses, particularly responses in primary human cells can display significant variability from day to day and from donor to donor. One important aspect of the present invention is that while absolute amounts of parameters can vary substantially between assays, combinatorial responses provide for less variability and the process of normalization to produce a biomap provides cellular activity profiles that are robust and reproducible.

FIG. 2B shows a graphical representation of reference biomaps developed from assay combinations in which one or more of the cytokines, IL1, TNF-α or IFN-γ is eliminated. For each reference assay combination, the selected parameters are measured and the resulting biomaps developed from the data are compared. Measuring the levels of the parameters ICAM-1 (1), VCAM-1 (2), E-selectin (3), IL-8 (4), CD31 (5), HLA-DR (6), and MIG (7), by cell-based ELISA under each of these assay combinations, results in different reference biomaps for each assay combination. The set of parameter measurements under each of these conditions comprises a reference biomap to which test patterns can be compared. The measurement obtained for each parameter is classified according to its relative change from the value obtained in the optimized assay combination (containing IL-1+TNF-α+IFN-γ), and represented by shaded squares. For each parameter and assay combination, the "checkered" squares indicate if the parameter measurement is unchanged (<20% above or below the measurement in the first assay combination (IL-1+TNF-α+IFN-γ)) or p>0.05, n=3; "diagonal striped" squares indicate that the parameter measurement is moderately increased (>20% but <50%), "white" indicates the parameter measurement is strongly increased (>50%); "vertical striped" indicates that the parameter measurement is moderated decreased (>20% but <50%); "hatched" indicates that the parameter measurement is strongly decreased (>50% less than the level measured in the first assay combination).

FIG. 2C shows an alternative visual representation of the set of reference biomaps whereby individual parameter readouts are compared by hierarchical cluster analysis. For this, regression analysis is performed on reference biomaps and correlation coefficients are used in cluster analysis. The clustering relationships can be represented visually, for example, as a tree in which related biomaps are on common branches, and the distance between patterns on the tree reflects the extent of differences in the biomaps. The biomaps derived from assay combinations containing TNF-α and/or IL1 are easily distinguished from those derived from assay combinations containing IFN-γ or the combination of IFN-γ and TNF-α and/or IL-1.

Applying weighting factors to individual parameter readouts allows the biomap analysis to sufficiently distinguish particular signaling pathways of interest. A significant aspect of the invention is the selection of a set of parameters and assay combinations that can optimally distinguish multiple pathways of interest. Active compounds are chosen on the basis of their ability to alter the resulting biomap when included in a selected assay combination. Such alteration may include returning the levels of one or more parameters to their levels in the basal condition, or otherwise altering the cellular responses, particularly when such alterations reflect changes towards a desirable cellular state.

An inhibitor of TNF-α is an active compound in the optimized assay combination described above. Addition of neutralizing anti-TNF-α antibodies to this assay combination results in reduced expression levels of ICAM-1, VCAM-1, E-selectin, IL-8, and MIG, and increased expression levels of CD31, as shown in FIG. 3A. Confluent cultures of HUVEC cells are treated with TNF-α (5 ng/ml)+IFN-γ (100 ng/ml)+IL-1 (1 ng/ml) in the presence or absence of neutralizing anti-TNF-α or control antibody (Goat anti-IgG). After 24 hours, cultures are washed and evaluated for the cell surface expression of ICAM-1 (1), VCAM-1 (2), E-selectin (3), IL-8 (4), CD31 (5), HLA-DR (6) and MIG (7) by cell-based ELISA performed as described in for FIG. 1A. The relative expression of each parameter is shown along the y-axis as average value of the OD measured at 450 nm of triplicate samples. The mean +/−SD from triplicate samples are shown. * indicates p<0.05 comparing results obtained With anti-TNF-α to the control.

FIG. 3B, is a graphical representation of the biomaps developed from the data shown in A. For each parameter and assay combination, the "checkered" squares indicate if the parameter measurement is unchanged (<20% above or below the measurement in the first assay combination (IL-1+TNF-α+IFN-γ)) or p>0.05, n=3; "diagonal striped" squares indicate that the parameter measurement is moderately increased (>20% but <50%); "white" indicates the parameter measurement is strongly increased (>50%); "vertical striped" indicates that the parameter measurement is moderated decreased (>20% but <50%); "hatched" indicates that the parameter measurement is strongly decreased (>50% less than the level measured in the first assay combination).

Figure 4A:
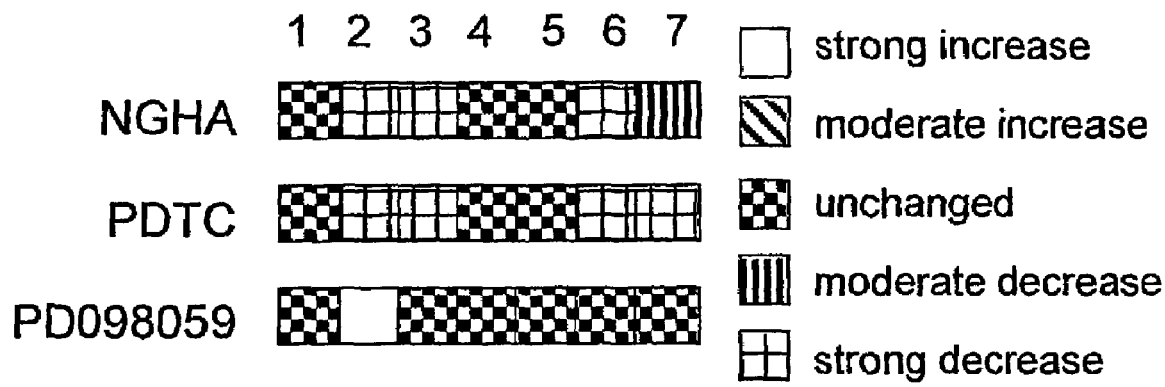
FIGS. 4A-4C. Effect of NFκB inhibitors nordihydroguaiaretic acid (NHGA) and pyrrolidine dithiocarbamate (PDTC), MAP kinase inhibitor PD098059, or ibuprofen on the expression of readout parameters in the inflammatory assay combination containing three factors (IL-1+TNF-α+IFN-γ).

Inhibitors of NFκB, MAP kinases and non-steroidal anti-inflammatory drugs are active compounds in the optimized assay combination described above. FIG. 4A shows results of assaying confluent cultures of HUVEC cells treated with TNF-α (5 ng/ml)+IFN-γ (100 ng/ml)+IL-1 (1 ng/ml) in the presence or absence of (FIG. 4A) 10 μM NHGA, 200 YM PDTC or 9 μM PD098059 or (FIG. 4B) 125-500 μM ibuprofen. Compounds are tested at the highest concentration at which they are soluble, and do not result in cellular toxicity or loss of cells from the plate. After 24 hours, cultures are washed and evaluated for the cell surface expression of ICAM-1 (1), VCAM-1 (2), E-selectin (3), IL-8 (4), CD31 (5), HLA-DR (6) and MIG (7) by cell-based ELISA performed as described above.

A graphical representation of the biomaps developed from the data is shown. For each parameter and assay combination, the "checkered" squares indicate if the parameter measurement is unchanged (<20% above or below the measurement in the first assay combination (IL-1+TNF-α+IFN-γ)) or p>0.05, n=3; "diagonal striped" squares indicate that the parameter measurement is moderately increased (>20% but <50%); "white" indicates the parameter measurement is strongly increased (>50%); "vertical striped" indicates that the parameter measurement is moderated decreased (>20% but <50%); "hatched" indicates that the parameter measurement is strongly decreased (>50% less than the level measured in the first assay combination).

In the present example, addition of the NFκB inhibitors nordihydroguaiaretic acid (NHGA) (Brennen, Biochem. Pharmacol., 55:965, 1998) or pyrrolidine dithiocarbamate (PDTC) (Boyle, Circulation, 98, (19 Suppl):11282, 1998) to the optimized assay combination results in altered biomaps that are distinct from the altered biomaps obtained with the p42/44 MAP kinase inhibitor, PD098059 (Milanini, J. Biol. Chem. 273:18165, 1998). Active compounds that act with a similar mechanism of action as NHGA and PDTC will give a biomap that can be distinguished from active compounds that act with a similar mechanism of action as PD098059.

Figure 4B:
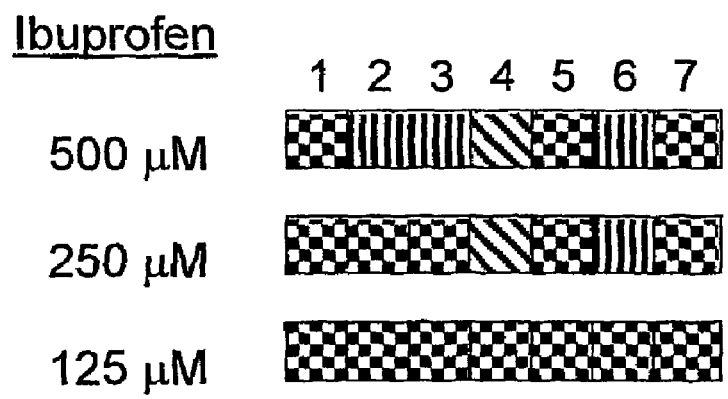

Obtaining biomaps from drug compounds tested at different concentrations also expands the usefulness of the database. In the, present example, ibuprofen gives visually different representations of biomaps when tested at 500, 250 and 125 μM, as shown in FIG. 4B, thus allowing for determination of the dose response and optimal drug concentration for the maximal biological response.

Reference biomaps from assay combinations that include known drug compounds, agents, or with other specific modifications are developed for inclusion in a database. Biomaps from these assay combinations are developed so as to expand the usefulness of the database. Table 1 shows a list of agents or specific modifications evaluated, including N-acetylcysteine (Faruqui, Am. J. Physiol. 273(2 Pt 2):H817, 1997), the corticosteroids dexamethasone and prednisolone, echinacea, AA861 (Lee, J. Immunol. 158, 3401, 1997), apigenin (Gerritsen, Am. J. Pathol. 147:278, 1995), nordihydroguaiaretic acid (NHGA) (Brennen, Biochem. Pharmacol., 55:965, 1998), phenylarsine oxide (PAO) (Dhawan, Eur. J. Immunol. 27:2172, 1997), pyrrolidine dithiocarbamate (PDTC) (Boyle, Circulation, 98, (19 Suppl):11282, 1998), PPM-18 (Yu, Biochem. J., 328:363, 1997), the non-steroidal anti-inflammatory drug (NSAID) buprofen, SB 203580, PD098059 (Milanini, J. Biol. Chem. 273:18165, 1998), AG126 (Novogrodsky, Science 264, 1319, 1994), and neutralizing anti-TNF-α antibody. Graphical representations of the resulting biomaps are shown.

Confluent cultures of HUVEC cells are treated with TNF-α (5 ng/ml)+IFN-γ (100 ng/ml)+IL-1 (1 ng/ml) in the presence or absence of agents or buffers at the concentrations indicated in Table 1. Compounds are obtained from commercial sources and prepared in a suitable buffer (water, base media, DMSO, methanol or ethanol). After 24 hours, cultures are washed and evaluated for the cell surface expression of ICAM-1 (1), VCAM-1 (2), E-selectin (3), IL-8 (4), CD31 (5), HLA-DR (6) and MIG (7) by cell-based ELISA performed as described above. A color-coded representation of the resulting biomaps developed from the data is shown. For each parameter and assay combination, the square is colored light gray if the parameter measurement is unchanged (<20% above or below the measurement in the control assay combination (IL-1+TNF-α+IFN-γ)) or p>0.05, n=3; white/gray hatched indicates that the parameter measurement is moderately increased (>20% but <50%); white indicates the parameter measurement is strongly increased (>50%); black/gray hatched indicates that the parameter measurement is moderately decreased (>20% but <50%); black indicates that the parameter measurement is strongly decreased (>50% less than the level measured in the first. Control assay combinations for each agent include an appropriate concentration of the diluent buffer.

TABLE 1

Reference biomaps.

| Inhibitor Class | UID | Compound | Conc. | Units | 1 | 2 | 3 | 4 | 5 | 6 | 7 |
|---|---|---|---|---|---|---|---|---|---|---|---|
| Antioxidant | 181 | N-acetylcysteine | 5.00 | μM | | | | | | | |
| Antioxidant | 182 | N-acetylcysteine | 2.50 | μM | | | | | | | |
| Antioxidant | 183 | N-acetylcysteine | 1.25 | μM | | | | | | | |
| Antioxidant | 184 | N-acetylcysteine | 1.25 | μM | | | | | | | |
| Corticosteroid | 717 | Dexamethazone | 12.50 | μM | | | | | | | |
| Corticosteroid | 716 | Dexamethazone | 6.25 | μM | | | | | | | |
| Corticosteroid | 715 | Dexamethazone | 3.10 | μM | | | | | | | |
| Corticosteroid | 301 | Dexamethazone | 2.00 | μM | | | | | | | |
| Corticosteroid | 302 | Dexamethazone | 1.00 | μM | | | | | | | |
| Corticosteroid | 303 | Dexamethazone | 0.50 | μM | | | | | | | |
| Corticosteroid | 241 | Prednisolone | 160.00 | μM | | | | | | | |
| Corticosteroid | 242 | Prednisolone | 160.00 | μM | | | | | | | |
| Corticosteroid | 243 | Prednisolone | 80.00 | μM | | | | | | | |
| Corticosteroid | 244 | Prednisolone | 40.00 | μM | | | | | | | |
| Natural Product | 91 | Echinacea | 2.27 | % | | | | | | | |
| Natural Product | 94 | Echinacea | 2.27 | % | | | | | | | |
| Natural Product | 92 | Echinacea | 1.13 | % | | | | | | | |
| Natural Product | 93 | Echinacea | 0.57 | % | | | | | | | |
| NFκB | 4 | AA861 | 20.00 | μM | | | | | ND | | |
| NFκB | 5 | AA861 | 20.00 | μM | | | | | ND | ND | |
| NFκB | 6 | AA861 | 20.00 | μM | | | | | | | |
| NFκB | 701 | AA861 | 20.00 | μM | | | | | | ND | |
| NFκB | 19 | Apigenen | 8.10 | μM | | | | | | | |
| NFκB | 20 | Apigenen | 6.00 | μM | | | | | | | |
| NFκB | 21 | Apigenen | 5.00 | μM | | | | | | | |
| NFκB | 202 | Nordihydroguaiaretic acid (NHGA) | 10.00 | μM | | | | | ND | | |
| NFκB | 203 | Nordihydroguaiaretic acid (NHGA) | 10.00 | μM | | | | | ND | ND | |
| NFκB | 204 | Nordihydroguaiaretic acid (NHGA) | 10.00 | μM | | | | | | | |
| NFκB | 719 | Nordihydroguaiaretic acid (NHGA) | 6.00 | μM | | | | | | | |
| NFκB | 205 | Nordihydroguaiaretic acid (NHGA) | 5.00 | μM | | | | | | | |
| NFκB | 718 | Nordihydroguaiaretic acid (NHGA) | 0.63 | μM | | | | | | | |
| NFκB | 720 | PAO | 50.00 | μM | | | | | | | |
| NFκB | 231 | PDTC | 200.00 | μM | | | | | | | |
| NFκB | 233 | PDTC | 200.00 | μM | | | | | | | |
| NFκB | 234 | PDTC | 200.00 | μM | | | | | | | |
| NFκB | 725 | PDTC | 100.00 | μM | | | | | | | ND |

TABLE 1-continued

Reference biomaps.

| | | | | | |
|---|---|---|---|---|---|
| NFκB | 726 | PDTC | 100.00 | μM | |
| NFκB | 235 | PDTC | 100.00 | μM | |
| NFκB | 232 | PDTC | 50.00 | μM | ND |
| NFκB | 724 | PDTC | 50.00 | μM | ND ND ND |
| NFκB | 236 | PDTC | 50.00 | μM | |
| NFκB | 728 | PPM-18 | 2.50 | μM | |
| NFκB | 727 | PPM-18 | 2.00 | μM | |
| NFκB | 735 | PPM-18 | 2.00 | μM | |
| NSAID | 131 | Ibuprofen | 500.00 | μM | |
| NSAID | 132 | Ibuprofen | 500.00 | μM | |
| p38 MAPK | 730 | SB 203580 | 80.00 | μM | ND |
| p38 MAPK | 729 | SB 203580 | 40.00 | μM | ND |
| p42/44 MAPK | 221 | PD098059 | 18.70 | μM | ND ND |
| p42/44 MAPK | 222 | PD098059 | 9.30 | μM | ND ND |
| p42/44 MAPK | 223 | PD098059 | 9.30 | μM | ND |

| | | | | | |
|---|---|---|---|---|---|
| p42/44 MAPK | 224 | PD098059 | 9.00 | μM | |
| p42/44 MAPK | 723 | PD098059 | 9.00 | μM | ND |
| p42/44 MAPK | 225 | PD098059 | 4.60 | μM | ND ND |
| p42/44 MAPK | 722 | PD098059 | 2.25 | μM | ND |
| p42/44 MAPK | 721 | PD098059 | 0.56 | μM | ND |
| Tyr Kinase | 733 | AG126 | 25.00 | μM | |
| Tyr Kinase | 702 | AG126 | 25.00 | μM | |
| Tyr Kinase | 734 | AG126 | 25.00 | μM | |
| Antibody | 712 | Anti-TNF | 5.00 | μg/ml | ND ND |
| Antibody | 713 | Anti-TNF | 5.00 | μg/ml | ND |
| Antibody | 711 | Anti-TNF | 4.00 | μg/ml | ND ND |
| Antibody | 710 | Anti-TNF | 1.67 | μg/ml | ND ND |
| Antibody | 709 | Anti-TNF | 0.55 | μg/ml | ND ND |
| Antibody | 708 | Anti-TNF | 0.40 | μg/ml | ND ND |
| Antibody | 707 | Anti-TNF | 0.04 | μg/ml | ND ND |

| | | | | | |
|---|---|---|---|---|---|
| Antibody | 714 | Anti-TNF-R (Act) | 5.00 | μg/ml | ND ND |
| N/A | 520 | Control | | | |
| N/A | 521 | Control | | | |
| N/A | 522 | Control | | | |
| N/A | 523 | Control | | | |
| N/A | 524 | Control | | | ND |
| N/A | 525 | No IL1 | | | |
| N/A | 526 | No IL1 | | | |
| N/A | 527 | No IL1 | | | ND |
| N/A | 531 | No TNF | | | |
| N/A | 532 | No TNF | | | |
| N/A | 533 | No TNF | | | ND |
| N/A | 515 | NoIL1IFNg | | | |
| N/A | 516 | NoIL1IFNg | | | |
| N/A | 517 | NoIL1IFNg | | | |

| | | | | | |
|---|---|---|---|---|---|
| N/A | 518 | NoIL1IFNg | | | |
| N/A | 519 | NoIL1IFNg | | | ND |
| N/A | 510 | NoTNFIFNg | | | |
| N/A | 511 | NoTNFIFNg | | | |

TABLE 1-continued

Reference biomaps.

| | | | | | | | |
|---|---|---|---|---|---|---|---|
| N/A | 512 | NoTNFIFNg | | | | | |
| N/A | 513 | NoTNFIFNg | | | | | |
| N/A | 514 | NoTNFIFNg | | | | ND | |
| N/A | 505 | No IL1TNF | | | | | |
| N/A | 506 | No IL1TNF | | | | | |
| N/A | 507 | No IL1TNF | | | | | |
| N/A | 508 | No IL1TNF | | | | | |
| N/A | 509 | No IL1TNF | | | | ND | |
| N/A | 500 | No IL1TNFIFNg | | | | | |
| N/A | 501 | No IL1TNFIFNg | | | | | |
| N/A | 502 | No IL1TNFIFNg | | | | | |
| N/A | 503 | No IL1TNFIFNg | | | | | |
| N/A | 504 | No IL1TNFIFNg | | | | ND | |

Figure 4C:
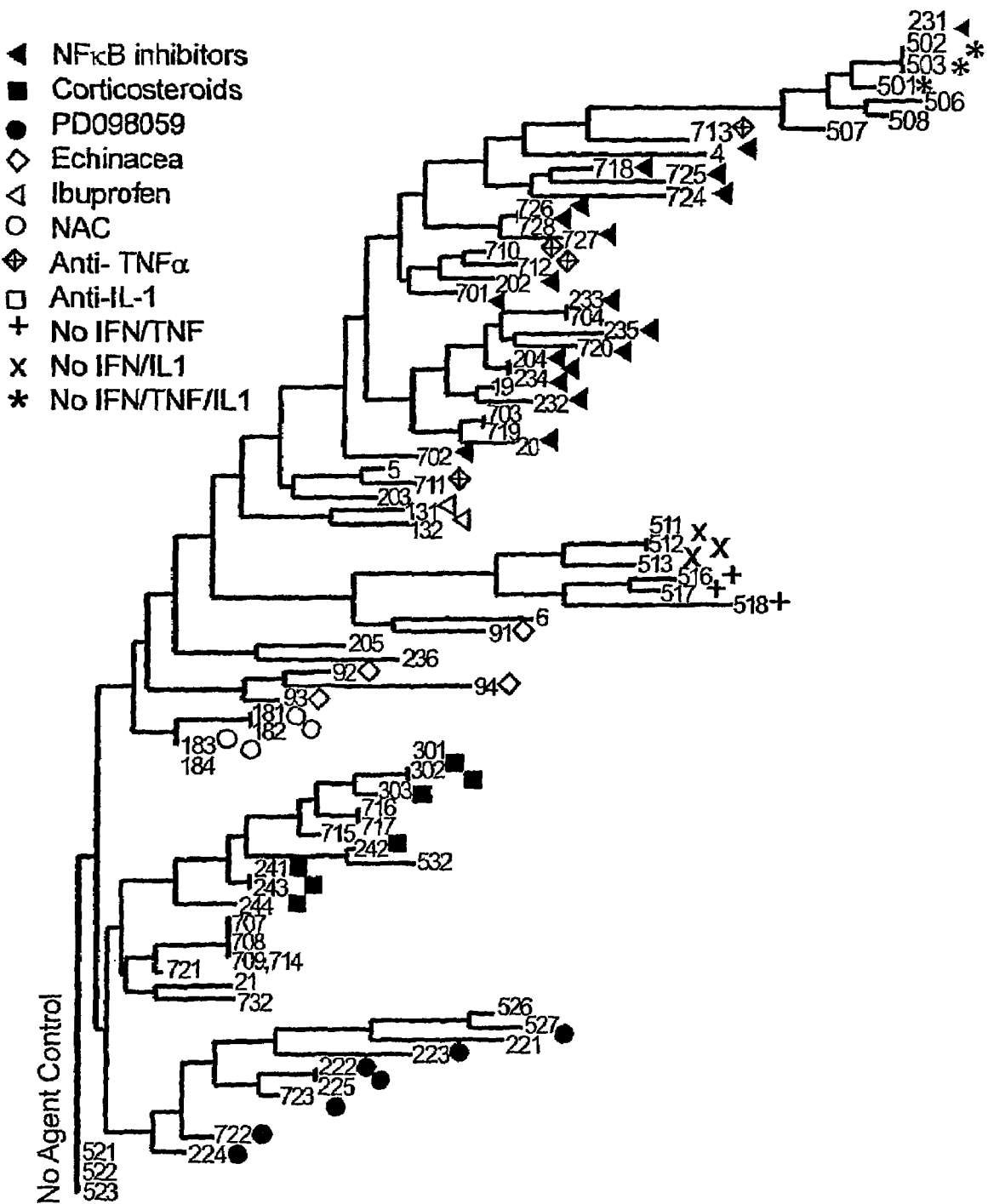

FIG. 4C shows a visual representation of how these reference biomaps can be compared by pattern similarity and cluster analysis. Readout patterns are analyzed by hierarchical clustering techniques, and are visualized as a tree diagram in which a) each terminal branch point represents the readout pattern from one assay combination in one experiment; b) the length of the vertical distance from the upper horizontal line (no change and control patterns) to the termini are related to the extent of difference in the readout pattern from the control environment pattern; and c) the distance along, the branches from one terminal pattern value to another reflects the extent of difference between them. Similar patterns are thus clustered together.

Compounds that inhibit the NFκB pathway, such as the 5-lipoxygenase inhibitors AA861 and nordihydroguaiaretic acid (NHGA) (Lee, J. Immunol. 158, 3401, 1997), pyrrolidine dithiocarbamate (PDTC) (Boyle, Circulation 98:(19 Suppl):11282, 1998), PPM-18, a chemically synthesized naphthoquinone derivative (Yu, Biochem. J., 328:363, 1997) and the flavenoid apigenin (Gerritsen, Am. J. Pathol. 147: 278, 1995), have similar reference biomaps and cluster together. The corticosteroids, dexamethasone and prednisolone also yield a set of related reference biomaps that are distinct from those of NFκB pathway inhibitors.

An important feature of biomap analysis is how biomaps resulting from different concentrations of active agents, although they differ from one another, remain clustered together in the cluster analysis. This can be seen in FIG. 4C, where the biomaps that result from testing PD098059 at different concentrations remain in the same cluster (indicating their similarity with one another), although biomaps resulting from testing PD098059 at higher concentrations are found in the lower branches of the cluster, indicating higher degree of difference (lower correlation coefficient) from the biomaps resulting from no intervention or inactive agents. Thus biomap analysis is useful for distinguishing the mode of action of a variety of compounds.

This example demonstrates that the biomaps are useful in distinguishing the mode of action of candidate compounds, so as to know whether combinations of candidate compounds act on the same pathway or different pathways, their combined effect on parameter levels and whether they provide synergy or act in an antagonistic way.

These assay combinations are highly useful for testing a large number of compounds or agents with many different or unknown mechanisms of action. This procedure balances the desirability of a screening assay that provides in depth information, with the advantages of an assay that is also amenable for scale-up high throughput screening. The assay combinations described are useful for general screening for compounds with anti-inflammatory or proinflammatory activity. Assay combinations tailored for specific inflammatory diseases are developed by altering the combination of input biologically active agents. For example, specific assay combinations useful for inflammatory diseases that are more Th2-like in nature, such as asthma or allergy should include additional agents, such as IL-4 or IL-13, which are preferably found in those disease conditions, and so forth.

Example 2

Multiplex Assay Combinations for Distinguishing Mechanism of Action

The following example demonstrates the utility of the invention in identification of the mechanism of action of a test compound or intervention identified in the optimized assay combination of Example 1. This assay combination is included in a panel that contains specific and targeted alterations. A neutralizing antibody to TNF-α was selected as a test agent, as it is active when tested in the optimized primary assay combination of Example 1. When the test agent is evaluated in the panel of assay combinations, it can be determined if the active compound is acting on a component(s) unique to one receptor-stimulated pathway, or on a common pathway component or pathway activity. The neutralizing antibody to TNF-α as a test agent evaluated in these assay combinations alters the biomap, as shown in FIG. 5.

Confluent cultures of HUVEC cells are treated with TNF-α (5 ng/ml), IFN-γ (100 ng/ml), IL-1 (20 ng/ml), the combination of TNF-α+IFN-γ+IL-1, or media (no cytokine) in the presence or absence of neutralizing anti-TNF-α, 20 μM AA861 or 10 μM NHGA. After 24 hours, cultures are washed and evaluated for the cell surface expression of ICAM-1 (1), VCAM-1 (2), E-selectin (3), IL-8 (4), and MIG (5) by cell-based ELISA performed as described in Example 1. A graphical representation of the resulting biomaps derived from the data is shown in FIG. 5, coded as described above.

These data demonstrate expression of the biomap from the assay combination containing TNF-α alone is altered, but not the biomap in the assay combinations that contain IL-1 or IFN-γ alone. This result demonstrates that the test agent acts on the TNF-α pathway but not on the IL-1 or IFN-γ pathways. FIG. 5 also shows the test compound is distinguished from active compounds that target multiple cytokine signaling pathways, such as the NFκB inhibitors, NHGA and AA861.

The mechanism of action of the test agent is accomplished when identical biomaps are obtained from assay combinations containing the test agent and assay combinations generated from known specific alterations of the assay combination. Eliminating the cytokine TNF-α from the primary assay combination results in the same biomap as the assay combination containing the test agent, the neutralizing TNF-α antibody.

Confirmation is performed by evaluating the test agent in assay combinations that include both physiologic and alternative pathway activators. Confluent cultures of HUVEC cells are treated with TNF-α (5 ng/ml), IL-1 (20 ng/ml), an activating antibody against the TNF-α receptor p55, or media. After 24 hours, cultures are washed and evaluated for the cell surface expression of ICAM-1 (1), VCAM-1 (2), E-selectin (3), CD31 (4), and MIG (5) by cell-based ELISA performed as described above. A graphical representation of the resulting biomap, prepared from the data is shown in FIG. 6, coded as described above.

These data show that among the physiologic and alternative activators of the TNF-α pathway, the biomaps resulting from cultures containing either IL-1 or an activating antibody to p55 are not sensitive to the test agent, whereas the biomap resulting from cultures containing TNF-α is sensitive. As TNF-α is the most upstream component of the TNF-α pathway that is sensitive to the test agent, it is involved in the target pathway step of the test agent.

Example 3

Function of Genes in Cellular Responses in Inflammation

The present invention is useful for identifying functions of genes and their expressed gene products. For example, genes whose products regulate inflammation can be identified in an inflammation model using human endothelial cells as an indicator cell type. A panel of assay combinations that reproduce aspects of the response of the endothelial cells to different types of inflammatory processes is used, as described in Example 1.

Figure 7:
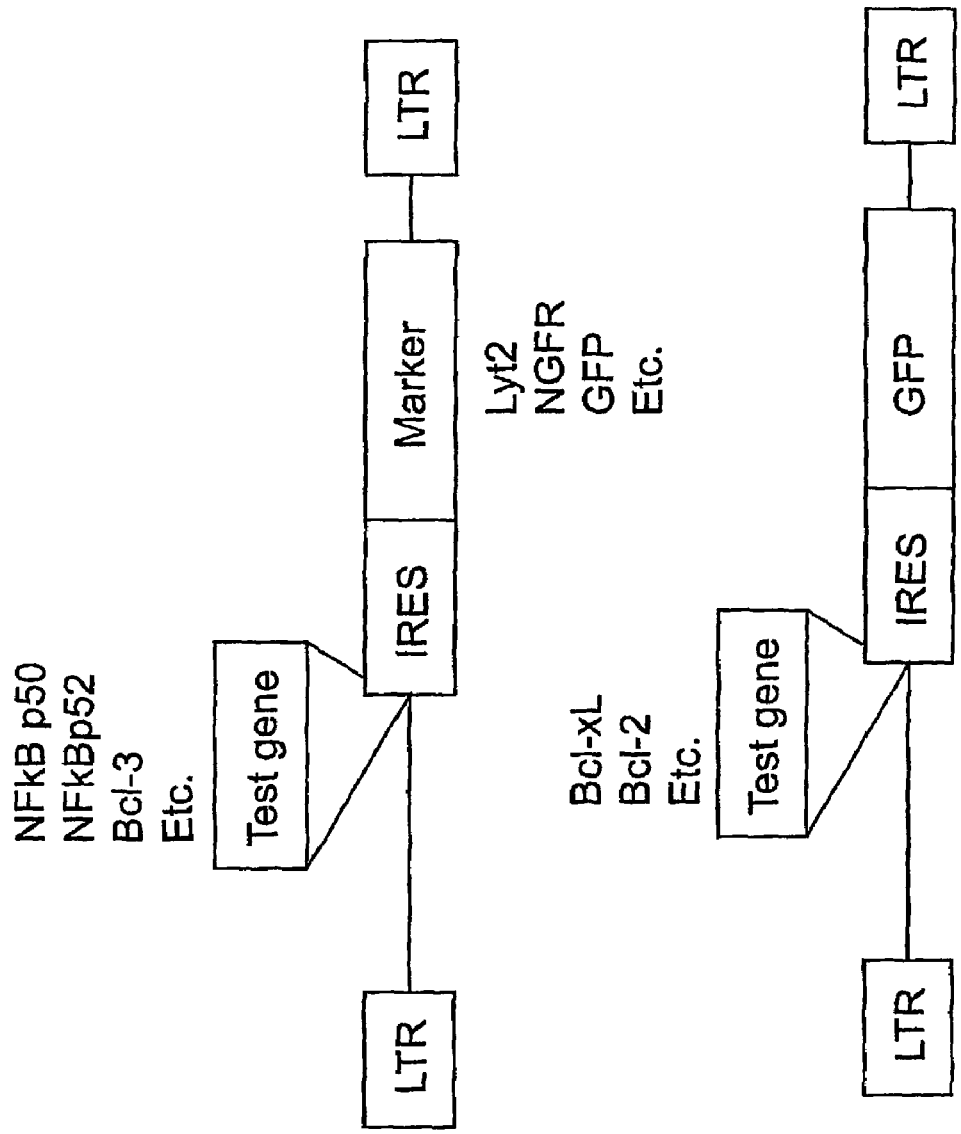
FIG. 7. Schematic representation of retroviral vector constructs (not drawn to scale). LTR, long terminal repeat; IRES, internal ribosomal entry site.

Primary human umbilical vein endothelial cells (HUVEC) are used. Other cells that may replace HUVEC in the screen include primary microvascular endothelial cells, aortic or arteriolar endothelial cells or endothelial cell lines such as EAhy926 or E6-E7 4-5-2G cells or human telomerase reverse transcriptase-expressing endothelial cells (Simmons, J. Immunol., 148:267, 1992; Rhim, Carcinogenesis 19:673, 1998; Yang, J. Biol. Chem. 274:26141, 1999). Endothelial cells in exponential growth phase are transduced with retroviral vectors or transfected with plasmid vectors encoding test genes. A marker gene is incorporated in the vector that allows monitoring of expression. A suitable retroviral vector is described in FIG. 7, and is derived from the MoMLV-based pFB vector (Stratagene). Other standard methods for transduction or transfection of cells for expression of genes can be substituted.

Test genes are inserted downstream of the MoMLV LTR. The marker gene is the truncated form of the human nerve growth factor receptor (NGFR)) (Mavilio, Blood 83:1988, 1994) separated from the test gene by an independent ribosomal entry site sequence (IRES). The IRES is 100 bp fragment from human eIF4G IRES sequence (Gan, J. Biol. Chem. 273:5006, 1988). For example, data presented in FIG. 8 was obtained from the test gene, human I kappa B-related Bcl-3 (Dechend, Oncogene, 18:3316, 1999). Retroviral vector plasmid DNA is transfected into AmphoPack-293 cells (Clonetech) by modified calcium phosphate method according to manufacturer's protocol (MBS transfection kit, Stratagene). Cell supernatants are harvested 48 hours post-transfection, filtered to remove cell debris (0.45 pm) and transferred onto exponentially growing HUVEC cells. DEAE dextran (conc 10 µg/ml) is added to facilitate vector transduction. After 5-8 hour incubation the viral supernatant is removed and cells cultured for an additional 40 hours. Gene transfer efficiency is determined by FACS using NGFR-specific monoclonal antibodies, and in the experiment shown, is >90%. Transduced cells are re-plated into 96-well plates, and cultured to confluence for biomap analysis.

Confluent transduced or control HUVEC cells are treated with the combination of TNF-α (5 ng/ml)+IFN-γ (100 ng/ml)+IL-1 (1 ng/ml); or with TNF-α (5 ng/ml), IL-1 (1 ng/ml) or media only. After 24 hours, cultures are washed and evaluated for the cell surface expression of ICAM-1 (1), VCAM-1 (2), E-selectin (3), IL-8 (4), CD31 (5), HLA-DR (6) and MIG (7) as in Example 1. FIG. 8 shows how over-expression of Bcl-3 results in altered biomaps in the assay panel used. Expression of Bcl-3 results in increased expression of ICAM-1 in endothelial cells under basal conditions, and enhanced expression of ICAM-1, VCAM-1 and E-selectin in cells cultured with IL-1. It does not alter the biomaps resulting from assay combinations containing TNFα or TNF-α+IFN-γ+IL-1. FIG. 8 shows a visual representation of the biomaps derived from the resulting data. Thus expression of Bcl-3 yields a distinctive biomap in the assay panel employed. It can be concluded from this biomap panel that bcl-3 alters the basal reference bioamp and the biomap from IL1, but not that from TNF. The results define bcl-3 as a potential target for modulation of the inflammatory response.

This example demonstrates that the biomap analysis is useful for identifying gene function. In this particular case the biomap analysis shows that Bcl-3 is involved in regulating expression of ICAM-1 and VCAM-1, and thus inflammatory states. Furthermore biomap analysis identifies cellular states in which gene functions alter cellular responses (e.g. IL-1 versus TNF biomap). Information about the function of unknown genes is obtained by comparing biomaps of unknown genes to the distinctive biomaps determined by the known gene products, drugs, antibodies, and other agents in various cellular states.

Example 4

Discrimination of Pathways: Regulation of Apoptosis

The present invention is useful for discriminating biologically active agents and genes that act on different pathways. Pathways involved in cellular apoptosis can be distinguished from those involved in regulation of adhesion molecules and cytokines in inflammation, and agents that modify these pathways can be identified.

A panel of assay combinations that reproduces aspects of the response of the endothelial cells to inflammatory processes and stimuli enhancing apoptosis is used. TNFα and ceramide are factors known to enhance cell apoptosis in endothelial cells (Slowik, Lab Invest. 77:257, 1997). Endothelial cells cultured under basal conditions display a low level of cell damage as measured by release of cytoplasmic lactate dehydrogenase from cells into the supernatant. This level is enhanced in cultures comprising TNF-α, ceramide, or the combination of ceramide and TNF-α.

Retroviral vectors derived from the MSCV-based pMSCVneo vector (Clontech) are used to express genes in the cultured endothelial cells. Other standard vectors or tranfection protocols can be substituted. Test genes are inserted downstream of the MSCV LTR, the marker gene is the enhanced green fluorescent protein (GFP) and the IRES is 600 bp fragment from EMCV virus (Jang, J. Virol. 63:1651, 1989). In this example, the test genes are human Bcl-2 and Bcl-xL. Retroviral vector plasmid DNA is transfected into AmphoPack-293 cells (Clontech) by modified calcium phosphate method according to manufacturer's protocol (MBS transfection kit, Stratagene). Cell supernatants are harvested 48 hours post-transfection, filtered to remove cell debris (0.45 pm) and transferred onto exponentially growing HUVEC cells. DEAE dextran (conc 1opg/ml) is added to facilitate vector transduction. After a 5-8 hour incubation period viral supernatants are removed and cells cultured for an additional 40 hours. Gene transfer efficiency is determined by FACS, and is typically ≧80 percent. Transduced cells are re-plated into 96-well plates for biomap analysis. Confluent HUVEC cells are treated with either ceramide (10 pm), TNF-α (5 ng/ml), ceramide (10 μm)+ TNF-α (5 ng/ml), or TNF-α (5 ng/ml)+IFN-g (100 ng/ml)+ IL-1 (1 ng/ml), or media only. After 24 hours, transduced cells are evaluated for the surface expression ICAM-1 (1), VCAM-1 (2), and MIG (3) by cell-based ELISA for biomap analysis. For the expanded biomap, cell supernatants at 24 hours are collected and analyzed for the presence of LDH (4). In the present example, over-expression of Bcl-2 and Bcl-xL results in altered biomap parameters that reflect an effect on the apoptotic pathway (e.g. parameter 4, LDH), but not biomap parameters that reflect adhesion and cytokine regulation pathways (parameters 1, 2 and 3; ICAM-1, VCAM-1 and MIG, respectively). Data are shown in FIG. 9.

This example clearly, shows the utility of biomap analysis for distinguishing gene effects on multiple cell functions and pathways, and in the present example, for identifying genes modulating apoptosis pathways.

Example 5

Function if Genes in Cellular Responses in Inflammation: Antisense Approach

The present invention is useful for identifying functions of genes and their expressed gene products using antisense approaches. For example, genes whose products regulate inflammation can be identified in an inflammation model using human endothelial cells as an indicator cell type. A panel of assay combinations that reproduce aspects of the response of the endothelial cells to different types of inflammatory processes is used, as described in Example 1.

Primary human umbilical vein endothelial cells (HUVEC) are used. Other cells that may replace HUVEC in the screen include primary microvascular endothelial cells, aortic or arteriolar endothelial cells or endothelial cell lines such as EAhy926 or E6-E7 4-5-2G cells or human telomerase reverse transcriptase-expressing endothelial cells (Simmons, J. Immunol., 148:267, 1992; Rhim, Carcinogenesis 19:673, 1998; Yang, J. Biol. Chem. 274:26141, 1999).

Morpholino phosphorodiamidate (MF) antisense oligonucleotides are used. Other chemical classes of antisense oligonucleotides that can be substituted for morpholinos include but are not limited to phosphorotioate oligonucleotides, N3'-P5' phosphoramidate oligonucleotides (NP), locked nucleic acid (LNA), 2'-O-methoxyethyl nucleic acid (MOE), 2'-fluoro-arabinonucleic acid (FANA), peptide nucleic acids (PNA) (reviewed in Toulme, Nature Biotech. 19:17, 2001); siRNA (Elbashir et al. (2000) Nature 411:494-498); ribozymes (Kawasaki et al. (2002) Nat. Biotech 20:376-380); standard antisense (Veres et al. (1998) J. Virol. 72:1894-1901). In the present example, antisense oligonucleotides for TNF-R1 (p55) (5'-AGGTCAGGCACG-GTGGAGAGGC-3')(SEQ ID NO:1), and the beta-globin control oligo (5'-CCTCTTACCTCAGTTACAATTTATA-3') (SEQ ID NO:2) (Gene Tools Inc.) are used. The transfection mixture is prepared by mixing 5 ml of stock morpholino (0.5 mM), 500 ml water, and 4 ml of 200 mM EPEI (Ethoxylated PolyEthylenlmine), vortexed, incubated at room temperature for 20 minutes, and then mixed with 3.5 ml of serum-free media to give a final 0.6 μM morpholino concentration.

Figure 10:
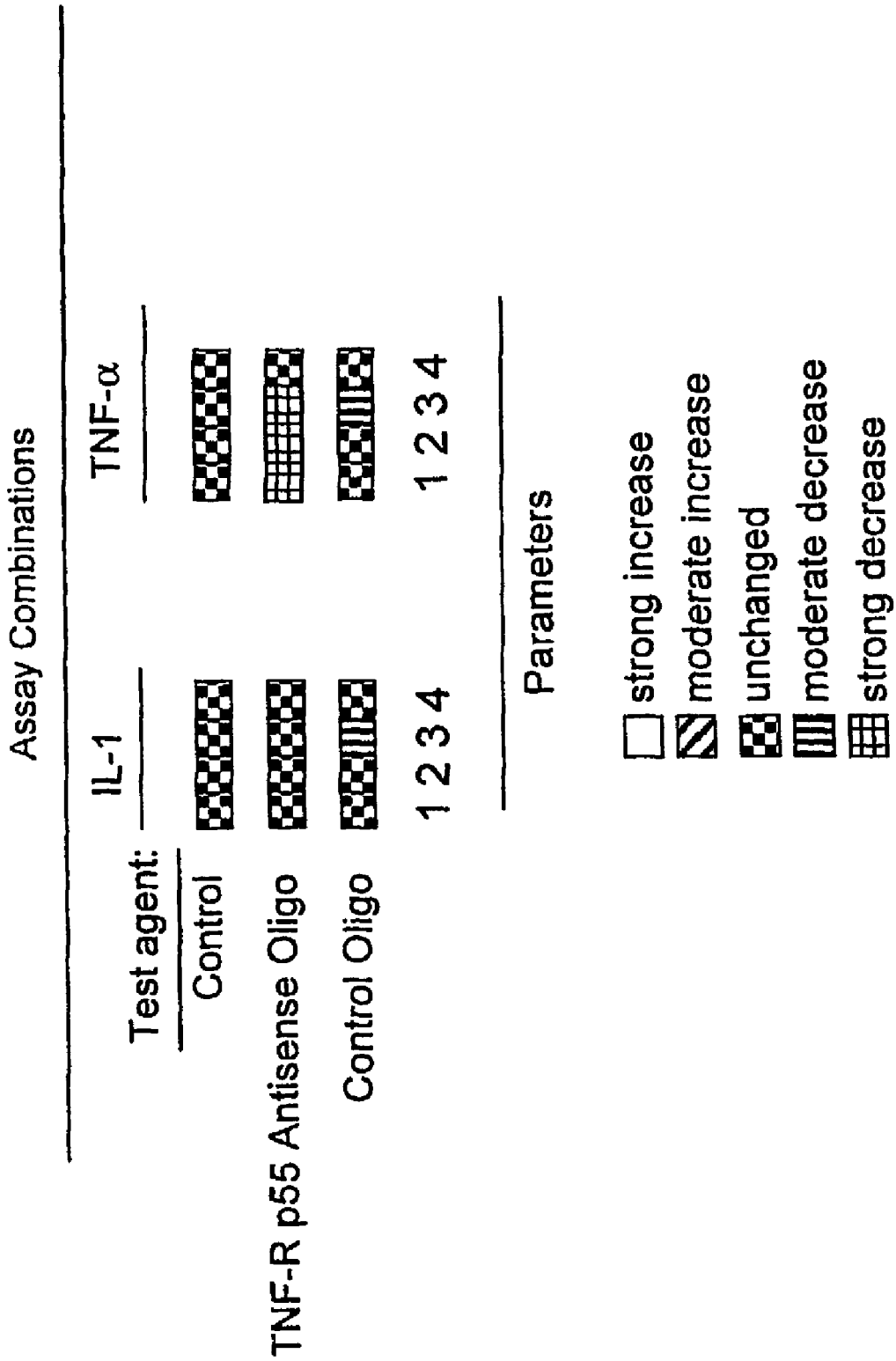
FIG. 10. Effect of TNF-R1-p55 antisense oligonucleotide on multiple assay combinations.

HUVEC cells are plated the day before in 24-well plates at 4-6×10e4 cells/well. Cells are washed once with serum-free media and incubated with 0.4 ml of the morpholino transfection mixture at 37° C. for 3 hours. Morpholino is removed, regular media (Epithelial Growth Media with 2% fetal calf serum, Clonetics) is added and cells allowed to recover overnight. The efficiency of loading of cells with morphino is monitored in cells incubated with a fluorescent morpholino, and is typically essentially 100 percent. HUVEC cells are then treated with either TNF-α (0.5 ng/ml), or IL-1 (1 ng/ml), or media only. After 4 hours, cells are harvested and evaluated for the cell surface expression of ICAM-1 (1), VCAM-1 (2), E-selectin (3), and CD31 (4) by flow cytometry. FIG. 10 shows that TNF-R1 antisense gives an altered biomap that is distinct from the control oligo biomap (with control morpholino) upon treatment with TNF-α, but not upon treatment with IL-1. The TNF-R1 antisense specifically blocks induction of ICAM-1 and VCAM-1 by TNF-α, while it has no effect on induction of the same markers by the independent cell surface receptor for IL-1.

The results illustrate the utility of the invention in identifying the function of genes in different assay combinations in an assay panel. This example clearly shows the utility of biomap analysis for distinguishing gene effects on multiple cell functions and pathways, and in the present example, for identifying genes involved in signaling by a proinflammatory cytokine.

Example 6

Gene Over-Expression Induces a Characteristic Biomap Profile

Multiple signaling pathways contribute to expression of endothelial cell molecules. For example, TNF-alpha and IL-1 activate the NFκB pathway resulting in increased transcription of E-selectin, ICAM-1, VCAM-1 and IL-8 by HUVEC (Collins, et al., Faseb J 1995, 9, 899-909 and FIG. 5). Upon binding to their respective cell surface receptors TNF-alpha and IL-1 induce signal transduction cascade involving multiple kinases, transcription factors and inhibitor proteins (Baeuerle, Curr Biology 1998, 8, R19-R22). The NFκB pathway is a well-studied pathway in endothelial cells. Briefly, NFκB (p65/p50 transcription factor dimer) is constitutively present in the cytoplasm of unstimulated endothelial cells in a complex with IκB protein, which prevents NFκB from entering the nucleus and activating gene transcription. Upon stimulation by TNF-alpha or IL-1, IκB is phosphorylated by IKK kinase, which in turn is activated by NIK kinase. Phosphorylated IκB is ubiquitinylated and degraded releasing the NFκB dimers, which can now move to the nucleus where they bind to NFκB binding promoter sites, and activate gene expression (reviewed in Baeurle, 1998, supra).

Endothelial cells also respond to'the cytokine IFN-gamma, although not through the NFκB pathway. Stimulation of cells with IFN-gamma results in activation of Jak1, Jak2 and STAT1. Activated STAT1 homodimer, or GAF, binds to GAS consensus sequeice and induces expression of GAS-containing primary target genes (Decker, et al., J Interferon Cytokine Res 1997, 17, 121-34). The ICAM-1 promoter contains a GAS sequence and is induced by IFN-gamma. Some primary target genes are themselves transcription factors and mediate delayed expression of other IFN-gamma-regulated genes. For example, IRF-1 is a transcription factor product of an IFN-gamma primary response gene that binds to sites on the VCAM-1 promoter and is required for maximal expression of VCAM-1 in response to TNF-alpha (Collins, et al., 1995, supra). Regulation of HLA-DR Class II expression by IFN-gamma is controlled by the IFN-gamma primary response gene, MHC2TA (Boss, Curr Opin Immunol 1997, 9,107-13).

Figure 11:
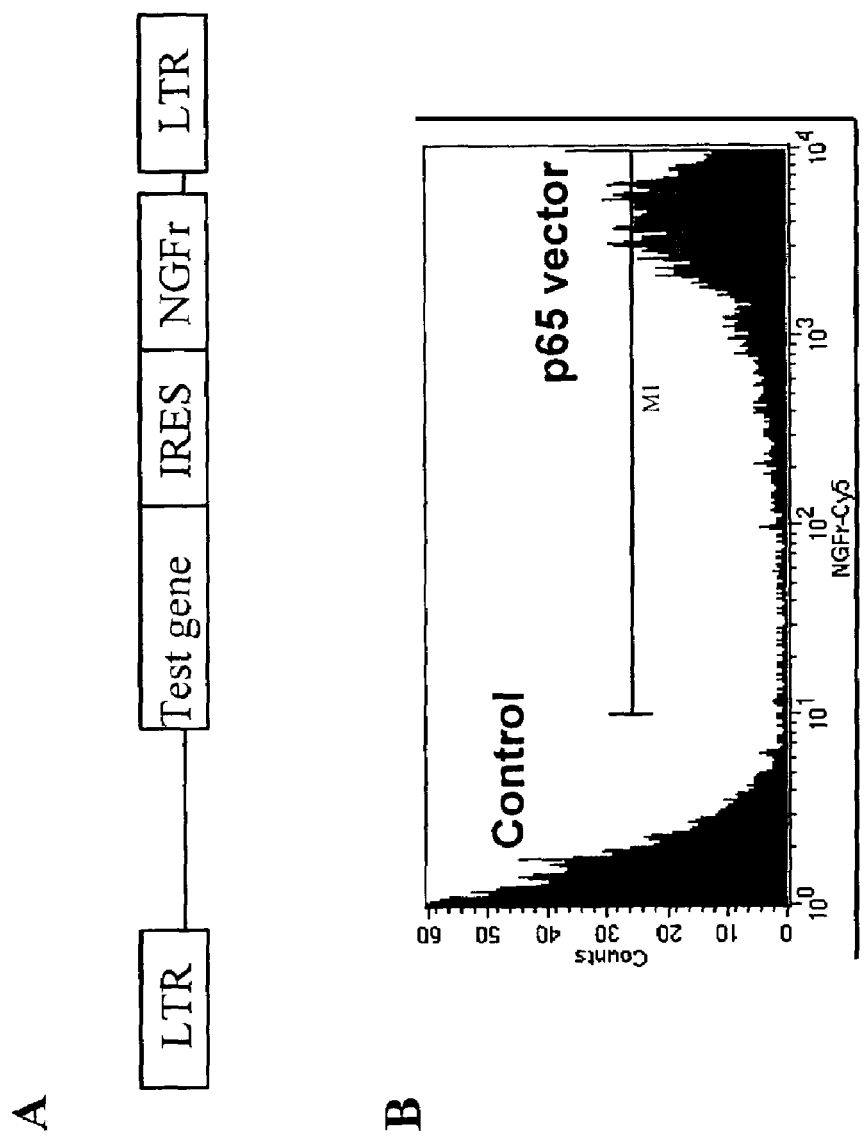
FIGS. 11A and 11B depict a retroviral vector (11A), and a graph of flow cytometry analysis of HUVECs transduced with the NFkBp65 expressing retroviral vector (11B). Cells were stained with the NFGr specific monoclonal antibody (Chemicon).

Over-expression of signaling pathway genes in HUVECs can change the BioMAP pattern in a specific way that is characteristic for each particular gene. Over-expression can be achieved using retroviral vectors. For the present purposes, a vector construct was generated shown in FIG. 11, from which a test gene and a marker gene, linked by IRES sequences, are coordinately expressed (Bonyhadi, et al., J Virol 1997, 71, 4707-16). The marker gene selected was the truncated form of the NGFr (Mavilio, et al., Blood 1994, 83, 1988-97), which has no effect on any signaling processes (Inaba, et al., J Surg Res 1998, 78, 31-36, and control experiments assessing effects on primary endothelial cell responses), and can easily be detected by flow cytometry or ELISA. High-titer retrovirus preparations are generated by transient transfection of vector construct into a retroviral packaging cell line (AmphoPack-293;Clontech). High expression levels and transduction efficiencies of 30-99% (generally>50%) are routinely achieved in primary endothelial cells (FIG. 11). Expression of BioMAP markers (ICAM-1, VCAM, etc.) is measured by a cell-based ELISA technique (Melrose, 1998, supra) that has been optimized such that changes in expression levels of >20% can be routinely detected as statistically significant effects (p<0.05). FIG. 11A, Diagram of retroviral vector. FIG. 11B, flow cytometry analysis of HUVECs transduced with the NFκB p65-expressing retroviral vector. Cells were stained with the NGFr specific monoclonal antibody (Chemicon).

Figure 12:
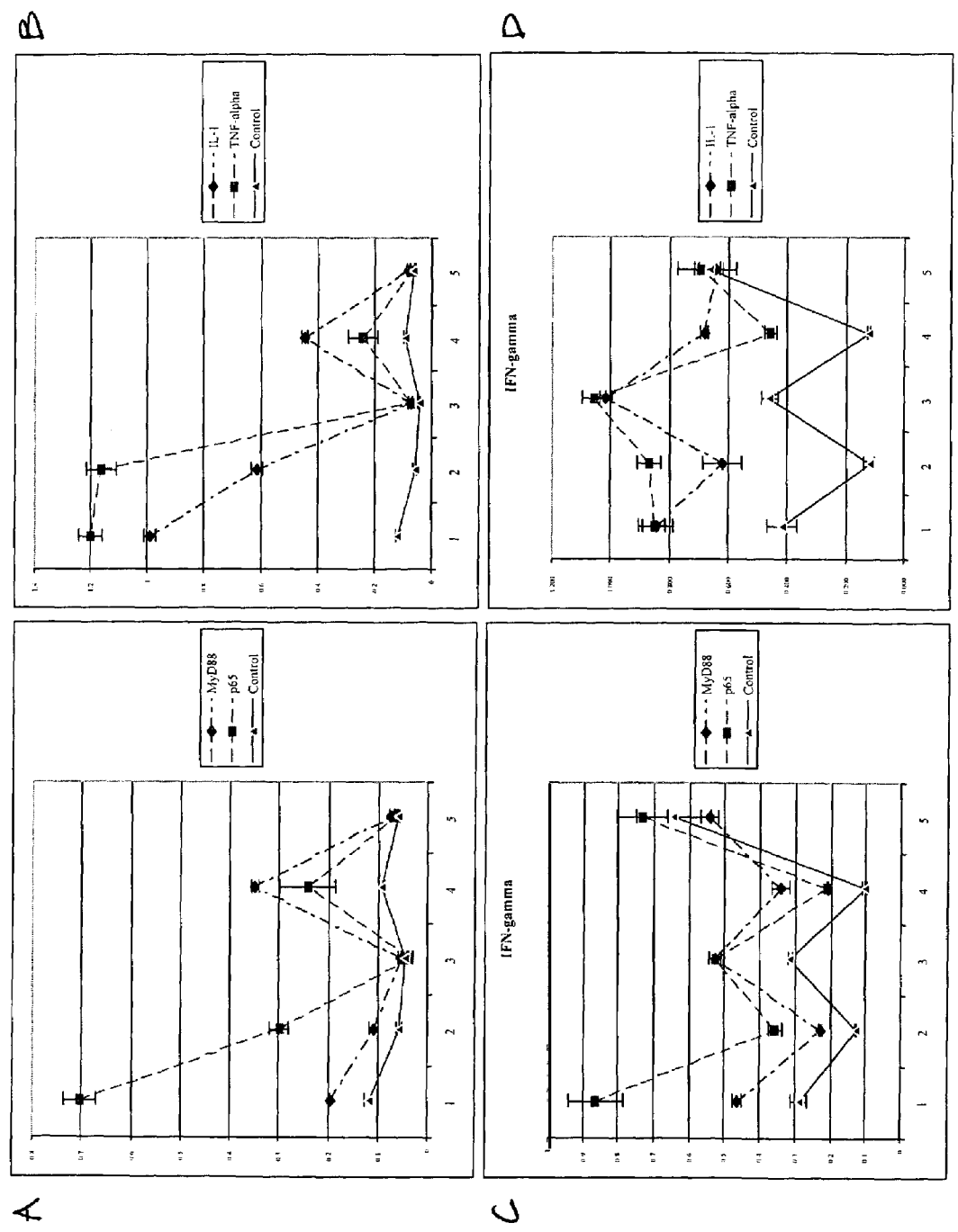
FIGS. 12A-12D are four graphs of HUVEC cells expressing (1) ICAM-1; (2) VCAM-1; (3) Mig; (4) IL-8; and (5) HLA-DR following cytokine activation (right panels), or transduction with the p65- and MyD88-expressing retroviral vector (left panels). In the lower two panels IFN-gamma was added to all samples. Average values (ELISA OD) from triplicate samples are shown, error bars indicate standard deviation. Control is HUVEC transduced with the "empty" vector that only encodes the NGFr marker.

Depicted in FIG. 12 is expression of (1) ICAM-1, (2) VCAM-1, (3) Mig, (4.) IL-8 and (5) HLA-DR on HUVEC cells following cytokine activation (right panels), or transduction with the p65 and MyD88-expressing retroviral vector (left panels). In the lower two panels IFN-gamma was added to all samples. Average values (ELISA OD) from triplicate samples are shown, error bars indicate standard deviation. Control is HUVEC transduced with the "empty" vector, which only encodes NGFr marker. Data are from a representative experiment. Results were reproduced in at least two experiments with HUVEC cells from different donors. FIG. 12 demonstrates how analyzing BioMAP patterns in gene over-expressing cells can differentiate genes (p65 and MyD88) involved in the NFκB pathway. p65 is a DNA-binding subunit of the NFκBdimer (it forms a dimer with p50). MyD88 is an adapter protein associated with the IL-1 receptor, and is involved in IL-1 signaling (Burns, et al., J Biol Chem 1998, 273,12203-12209).

Over expression of p65 and MyD88 in HUVECs results in up-regulated expression of a number of endothelial cell molecules (FIG. 12 upper left panel). When compared to BioMAP profiles from TNF-alpha and IL-1 stimulated HUVECs, the p65 BioMAP is more similar to the TNF-alpha BioMAP, while the MyD88 BioMAP is more similar to the IL-1 BioMAP (FIG. 12, compare upper left and right panels). Note that p65 and TNF-alpha mainly up-regulate ICAM-1 and VCAM-1, and to a lesser extent IL-8, while MyD88 and IL-1 strongly up-regulate IL-8, and less so ICAM-1 and VCAM-1. In addition, similar to TNF-alpha and IL-1, over-expression of either p65 or MyD88 acts in concert with IFN-gamma to further increase Mig expression (FIG. 12 lower panels). Thus, by analyzing expression profiles in gene-modified cells under various cytokine stimuli one can differentiate and categorize genes based on their specialized function, i.e. depending on which signaling pathways they participate in.

Example 7

A Variety of Gene Types are Detected in Biomap Assays

Figure 13:
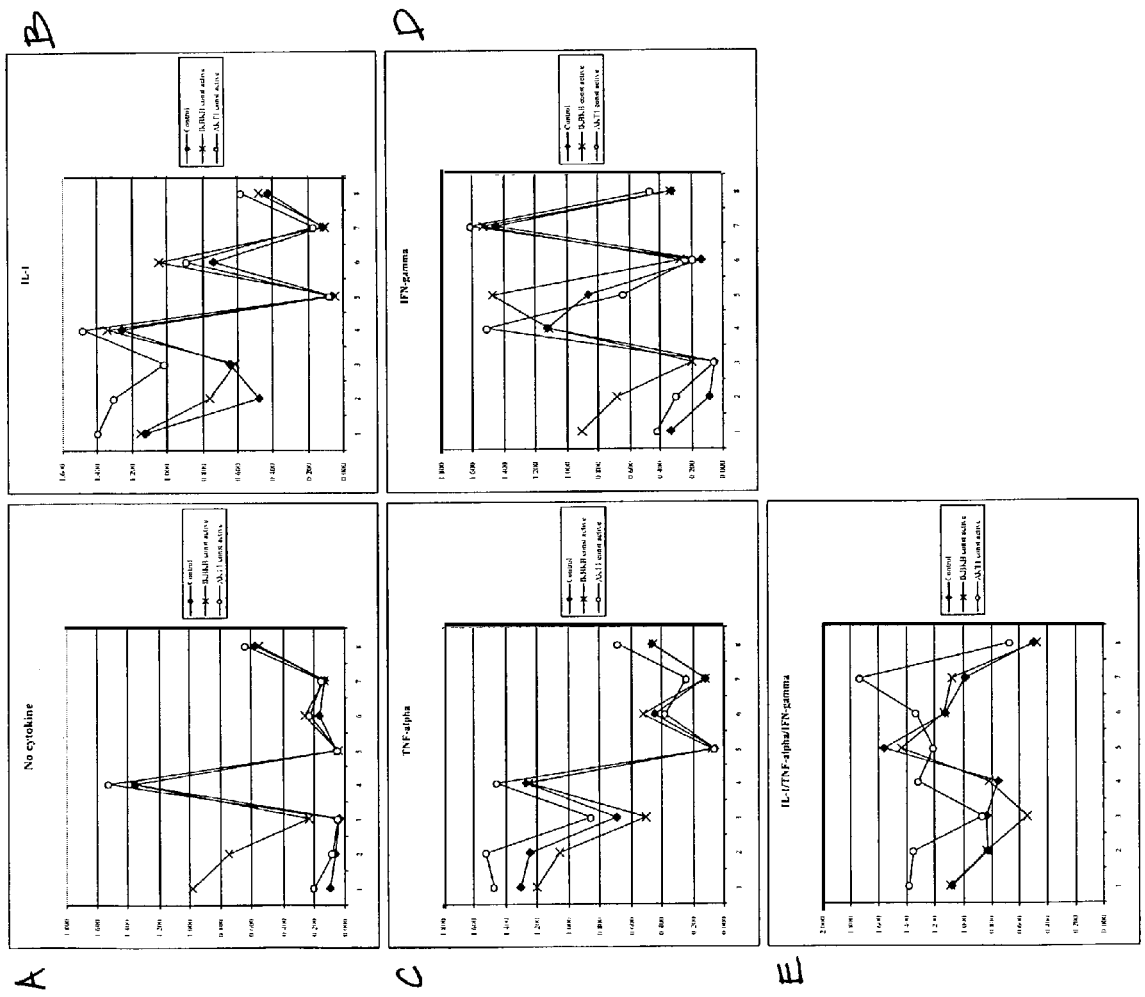
FIGS. 13A-13E are graphs of HUVEC cells expressing (1) ICAM-1; (2) VCAM-1; (3) E-selectin; (4) CD31; (5) Mig; (6) IL-8; (7) HLA-DR; and (8) MCP-1. The HUVEC cells were transduced with retroviral vectors encoding constitutively active IKBKB (x-x) and AKT1 (o-o) genes in the presence of TNF-alpha, IL-1, and IFN-gamma, individually or in combination. Average values (ELISA OD) from triplicate samples are shown. Control (_--_) is HUVEC transduced with the "empty" retroviral vector, which only encodes NGFr marker.

Gene over-expression vectors were generated for many members of the NFκB and Jak/STAT pathways, and measured BioMAP profiles in transduced HUVEC cells by a cell-based ELISA technique (Melrose, 1998, supra), in the presence of TNF-alpha, IL-1, IFN-gamma, individually or in combination. FIG. 13 depicts how the over expression of two kinase genes, IKBKB and AKT1, changes expression profiles of ICAM-1, VCAM-1, E-selectin, CD31, Mig, IL-8, HLA-DR, and MCP-1 on HUVEC cells. A variety of wild-type genes are active when over-expressed in BioMAP systems. These include soluble factors, signaling receptors, receptor-associated factors and transcription factors. (Table 2). In the case of kinase genes, such as AKT1 and IKBKB, over-expression of wild type genes did not result in altered BioMAP1 profiles, but constitutively active mutants were active in the assay (Table 2, AKT1 and IKBKB genes). Overall 16/29 (55%) of the genes tested (shown in Table 2) were active in the BioMAP assays. Shown in FIG. 13 are the results of expression of (1) ICAM-1, (2) VCAM-1, (3) E-selectin, (4) CD31, (5) Mig,(6) IL-8; (7) HLA-DR, and (8) MCP-1 on HUVEC cells transduced with retroviral vectors encoding constitutively active IKBKB (x-x) and AKT1 (o-o) genes, in the presence of TNF-alpha, IL-1, IFN-gamma, individually or in combination. Average values (ELISA OD) from triplicate samples are shown. Control (_-_) is HUVEC transduced with the "empty" retroviral vector, which only encodes NGFr marker. Data shown are from a representative experiment.

TABLE 2

| Gene | NFkB Pathway Type | BioMAP readout | Gene | JAK/STAT pathway Type | BioMAP readout |
|---|---|---|---|---|---|
| AKT1 | kinase | — | IFNGR1 | receptor | — |
| AKT1 const active | kinase | yes | IFNGR2 | receptor | yes |
| IKBKB (IKK β) | kinase | — | IFNG | soluble factor | yes |
| IKBKB const active | kinase | yes | MHC2TA | transcription factor | yes |
| IKBKG (KK γ) | kinase | — | STAT1 | transcription factor | — |
| TNFRSF1A (TNFa receptor) | receptor | yes | | | |
| TNFRSF5 (CD40) | receptor | yes | | | |
| MYD88 | receptor associated factor | yes | | | |
| RIP | receptor associated factor | yes | | | |
| TANK | receptor associated factor | — | | | |
| TRADD | receptor associated factor | yes | | | |
| TRAF2 | receptor associated factor | — | | | |
| TRAF6 | receptor associated factor | — | | | |
| TRIP | receptor associated factor | — | | | |
| NFKBIA (IkB α) | signal transduction | — | | | |
| NFKBIE (IkB ε) | signal transduction | — | | | |
| IL1A | soluble factor | yes | | | |
| IL1B | soluble factor | yes | | | |
| IL1RN | soluble factor | yes | | | |
| TNFA | soluble factor | yes | | | |
| TNFB | soluble factor | yes | | | |
| NFKB1 (P105/p50) | transcription factor | — | | | |
| NFKB2 (p52) | transcription factor | — | | | |
| RELA (p65) | transcription factor | yes | | | |

Table 2. List of genes tested in BioMap assays. HUVEC cells were transduced with retroviral vectors expressing listed genes, and analyzed as in Example 7. Active BioMap profiles (indicated as "yes") were significantly different from the profile obtained with the control vector, i.e. the value obtained for one or more parameter values was significantly and reproducibly different from the control vector ($p < 0.05$, n = 3).
BioMAP profiles that were not different from control vector are indicated as "—".

A required feature for this approach is that the BioMAP systems provide for reproducible profiles of parameter changes (BioMAP profiles) resulting from the same gene tested multiple times with cells from multiple donors. The reproducibility of BioMAP profiles data is demonstrated by comparing correlation coefficients of BioMAP profiles that are produced for same genes under identical conditions. As shown in Table 3, within an individual assay (Intra-assay comparison, cells tested from the same donor, under the same conditions and transduced with the same batch of retroviral vector), correlation coefficients of BioMAP profiles obtained from duplicate samples are very high (r=0.95-0.99). For comparison of data from different experiments, donors or dates, data can be normalized. One method of normalization can be accomplished by taking a ratio of the value obtained for each parameter in gene-transduced cells to the value obtained for that parameter in control vector-transduced cells. Although the efficiency of gene over-expression may vary from donor to donor and experiment to experiment the specific BioMAP patterns caused by gene over-expression are reproducible. Correlation coefficients for replicate treatments/genes between separate experiments, even with different endothelial cell donors and different batches of retroviral vector remain high (0.76-0.94)

TABLE 3

INTER-ASSAY COMPARISON

| | Intra-assay comparison | | | | Inter-assay comparison | | | |
|---|---|---|---|---|---|---|---|---|
| Gene | RELA | MYD88 | IFNG | AKT1 | RELA | MYD88 | IFNG | AKT1 |
| RELA | 0.978 | | | | 0.755 | | | |
| MyD88 | 0.423 | 0.969 | | | 0.521 | 0.943 | | |
| IFNG | −0.080 | −0.137 | 0.986 | | −0.193 | −0.130 | 0.756 | |
| AKT1 | 0.412 | 0.104 | 0.112 | 0.948 | 0.284 | 0.145 | −0.033 | 0.872 |

Table 3 Correlation coefficient comparing BioMAP profiles generated for a panel of genes tested in the same assay (Intra-assay comparison) or in assays performed with cells from two different primary donors, and using different batches of retroviral vector (Inter-assay comparison). The expression of ICAM-1, VCAM-1, E-selectin, CD31, Mig, IL-8, HLA-DR and MCP-1 was measured by ELISA on HUVEC cells transduced with RELA, MYD88, IFN-gamma, and constitutively active AKT1 genes, in the presence of TNF-alpha, IL-1, IFN-gamma, individually or in combination. ELISA OD values from triplicate samples were normalized by dividing the average values for each gene with the values obtained with control vector-transduced cells. For a given gene, normalized data from various cytokine treatments were combined into a single data string, and compared to other gene data strings by correlation analysis. Values in the table are Pearson's correlation coefficients.

Example 8

Validation of the System to Classify Genes into Different Molecular Pathways A feature of the BioMAP assay system is that the selection of parameters to be measured provides the ability to distinguish individual molecular pathways, distinguish genes that belong to different pathways, and to detect pathway interactions. In this example, genes that belong to the TNF-alpha signaling pathway are distinguished from the genes that belong to IFN-gamma signaling pathway. For this analysis, data from a larger set of genes and multiple experiments were compared by correlation analysis, and the correlation coefficients representing relative similarity of gene-specific BioMAP profiles to either TNF-alpha or IFN-gamma specific BioMAPs were ranked from most to least similar (Table 3).

Genes that are members of the NFκB pathway show high correlation (>0.79) to TNF-alpha BioMAP, and at the same time they show low or negative correlation to an IFN-gamma BioMAP. Furthermore, genes that can activate NFκB pathway but are not directly induced by TNF-alpha, such as MYD88 (IL-1 receptor associated factor) and AKT1 (induced by phosphatidylinositol 3-kinase) show moderate correlation (0.49) to the TNF-alpha BioMAP, and low or negative correlation to the IFN-gamma BioMAP. Because the BioMAP assay is directly measuring biological activity of genes, correlation analysis allows for grouping the genes based on the "biological function homology". In the present example the "function homology" indicates whether a particular gene is directly or indirectly associated with the NFkB pathway.

TABLE 4

| Gene | TNFA | Gene | IFNG |
|---|---|---|---|
| TNFA | 1.000 | IFNG | 1.000 |
| TNFB | 0.973 | MHC2TA | 0.985 |
| RELA | 0.933 | IFNG | 0.756 |
| TNFRSF1 | 0.881 | IL1RN | 0.117 |
| IKK const active | 0.845 | AKT1 const act | 0.109 |
| RIP | 0.787 | RIP | −0.012 |
| AKT1 const act | 0.493 | TNFA | −0.090 |
| MYD88 | 0.486 | IKK const active | −0.102 |
| IFNG | −0.025 | TNFB | −0.111 |
| MHC2TA | −0.131 | RELA | −0.116 |
| soluble IFN-gamma | −0.183 | MYD88 | −0.130 |
| IL1RN | −0.296 | TNFRSF1 | −0.181 |

Table 4. Correlation coefficient comparing BioMAP profiles generated for a panel of genes belonging to TNF-alpha or IFN-gamma induced pathways. The expression of adhesion molecules and chemokines, as described in Table 3 was measured on transduced HUVEC cells by ELISA. OD values from triplicate samples were normalized and compared by correlation analysis as described in Table 3. Values in the table are Pearson's correlation coefficients.

These data demonstrate that the response of primary cells to gene over-expression in a complex environment containing single and multiple exogenous cytokines can be sensitive and reproducible enough for utilization as a screening method for novel genetic regulators of inflammation. The system containing primary human endothelial cells stimulated with different proinflammatory cytokines allows a variety of functionally active genes to be detected and distinguished, based on their ability to modulate the expression of an optimized set of parameters. The data generated from this system is collected in a database so that novel genes can be compared to known genes based on biomaps, or "function homology". The current system is validated for its ability to detect and distinguish a variety of genes involved in NFκB and Jak/STAT pathways, as well as other pathways that are linked to the NFκB or Jak/STAT pathways. The ability to detect pathway interactions is shown in FIG. 13, where the AKT1 gene (which is not in the NFκB pathway) affects the BioMAP in, e.g. IL-1 stimulated cells, but not in non-stimulated cells. Thus, the AKT1 gene by itself does not activate the NFκB pathway, but it will modulate marker expression once the NFκB pathway has been activated by IL-1.

The BioMAP system, utilizing retroviral vector-transduced primary human endothelial cells in a complex cytokine environment, can detect a variety of gene classes including soluble factors, signaling receptors, receptor-associated factors, kinases and transcription factors. Gene over-expression, by providing the corresponding protein synthesized "in situ", avoids issues related to protein stability, glycosylation, cellular localization, or "contaminants" that may be present in the assay if a protein is produced in a separate expression system (e.g. baculovirus, yeast, CHO cells) and added exogenously.

A variety of wild-type genes are active when over-expressed in BioMAP systems including soluble factors, signaling receptors, receptor-associated factors and transcription factors (shown in Table 2). For certain genes (e.g. kinases, GTP-binding proteins), over-expression may fail to reveal a gene's function, for example when the gene product is regulated primarily by postranslational means, such as phosphorylation. Examples of this class of genes is AKT1 and IKBKB kinase genes, which were active in BioMAP assays only when expressed as constitutively active mutants (Table 2). For such genes, strategies such as exchange of serine or threonine for glutamic acid, or N-terminal truncation is used to generate constitutively active kinase mutants (Carter, et al., J Biol Chem 2001, 276, 24445-8; Tureckova, et al., ibid 2001, 276, 39264-70), while exchange of serine for alanine can lead to a dominant negative phenotype (Kuroda, et al., Biochem Biophys Res Commun 1998, 249, 781-5).

Some tested genes may not normally be expressed by endothelial cells, thus any activity in this system may not be physiologically relevant. To counter this, any gene that is active in this system will be tested for endogenous expression to confirm the relevance of the detected activity. Interestingly, if a gene is found to be active in this system, but is not found to be expressed by endothelial cells, activity profile obtained can still provide an indication of the pathways that the gene product may be involved in its normal host cell type. For example, IFN-gamma is not normally expressed by endothelial cells, and yet when over-expressed in this system, can be placed in the IFN-gamma pathway, as the resulting BioMAP is highly similar to the BioMAP profiles of the IFN-gamma itself and MHC2TA, known members of the IFN-gamma signaling pathway. Any soluble factor, or surface molecule that has a receptor on HUVEC cells can be expressed and affect the cells by an autocrine mechanism.

Results obtained by over-expression of members of the TNF-alpha and IFN-gamma signaling pathways confirm that the technique does effectively identify and categorize known functions of expressed molecules (Table 4). Over-expression of >200 genes that are known not to be members of the TNF-alpha and IFN-gamma signaling pathways, including trimeric G-proteins, small G-proteins, secreted molecules, receptors and receptor associated proteins and proteins involved in apoptosis did not yield "false positive" results.

The current selection of the BioMAP parameters is optimized for distinguishing key cytokine signaling pathways involved in inflammation, but it can be modified to measure other cellular processes such as apoptosis, cell cycle etc.

It is to be understood that this invention is not limited to the particular methodology, protocols, formulations and reagents described, as such may, of course, vary. It is also to be understood that the terminology used herein is for the purpose of describing particular embodiments only, and is not intended to limit the scope of the present invention, which will be limited only by the appended claims.

It must be noted that as used herein and in the appended claims, the singular forms "a", "and", and "the" include plural referents unless the context clearly dictates otherwise. Thus, for example, reference to "a complex" includes a plurality of such complexes and reference to "the formulation" includes reference to one or more formulations and equivalents thereof known to those skilled in the art, and so forth.

Unless defined otherwise, all technical and scientific terms used herein have the same meaning as commonly understood to one of ordinary skill in the art to which this invention belongs. Although any methods, devices and materials similar or equivalent to those described herein can be used in the practice or testing of the invention, the preferred methods, devices and materials are now described.

All publications mentioned herein are incorporated herein by reference for the purpose of describing and disclosing, for example, the methods and methodologies that are described in the publications, which might be used in connection with the presently described invention. The publications discussed above and throughout the text are provided solely for their disclosure prior to the filing date of the present application. Nothing herein is to be construed as an admission that the inventors are not entitled to antedate such disclosure by virtue of prior invention.

What is claimed is:

1. A method for characterization of a genetic agent according to its mechanism of action on cellular signaling pathways, the method comprising:
    expressing said genetic agent in a cell, wherein said cell is present in a cell culture assay combination, wherein said cell culture assay combination comprises cells and at least two factors sufficient to provide a physiological state of interest involving at least two pathways;
    recording changes in at least two different cellular parameter readouts whose levels vary as a result of introduction of said genetic agent;
    deriving a biomap dataset from said parameter readouts wherein said biomap comprises data normalized to be a ratio of test to control data on the same cell type under control conditions in the absence of said genetic agent, and said parameters are optimized so that the set of data in the biomap is sufficiently informative that it can discriminate the mechanism of action of said agent; and
    analyzing said biomap by a multiparameter pattern recognition algorithm to quantify relatedness of said biomap to reference biomaps that include known genetic agents that target specific pathways, wherein the presence or absence of relatedness to said reference biomaps provides a characterization of said genetic agent mechanism of action.

2. The method according to claim 1, wherein said genetic agent is introduced into said cell by transfection.

3. The method according to claim 1, wherein at least four parameters are measured.

4. The method according to claim 1, wherein said genetic agent is expressed in a panel of cell culture assay combinations; a biomap dataset is derived from each cell culture assay combination in said panel; and each biomap dataset in compared to a reference biomap dataset.

5. The method according to claim 4, wherein said assay combinations in said panel vary in the factors or cells that are present.

SEQUENCE LISTING

<160> NUMBER OF SEQ ID NOS: 2

<210> SEQ ID NO 1
<211> LENGTH: 22
<212> TYPE: DNA
<213> ORGANISM: Artificial Sequence
<220> FEATURE:
<223> OTHER INFORMATION: antisense oligonucleotides for TNF-R1

<400> SEQUENCE: 1
aggtcaggca cggtggagag gc                                    22

<210> SEQ ID NO 2
<211> LENGTH: 25
<212> TYPE: DNA
<213> ORGANISM: Artificial Sequence
<220> FEATURE:
<223> OTHER INFORMATION: beta-globin control oligonucleotides

<400> SEQUENCE: 2
cctcttacct cagttacaat ttata                                 25

6. The method according to claim 1, wherein said cells are endothelial cells.

7. The method according to claim 6, wherein said endothelial cells are primary cells.

8. The method according to claim 7, wherein said cells are primary HUVEC cells.

9. The method according to claim 6, wherein one of said at least two pathways is a pathway associated with inflammation.

10. The method according to claim 9, wherein said parameters include at least two of ICAM-1, VCAM-1, Mig, IL-8, and HLA-DR.

11. The method according to claim 1, wherein said cell is a leukocyte, cancer cell, or mast cell.

12. The method according to claim 1, wherein said genetic agent is constitutively active.

13. The method according to claim 1, wherein said genetic agent encodes an antisense nucleic acid.

14. A method for determining whether a genetic agent influences at least one pathway in a cell in a cell culture, the method comprising:

expressing said genetic agent in a genetically modified cell to overproduce the product of said genetic agent as compared to a cell in the basal state, wherein said cell is present in a cell culture assay combination, wherein said cell culture assay combination comprises at least two factors sufficient to provide a physiological state of interest involving at least two pathways in said cell in said cell culture, said pathways being indicated by levels of selected cellular parameters;

incubating said genetically modified cell in said culture for sufficient time for expression of said genetic agent and growth of said cell;

incubating said basal state cell in said culture for a time analogous to said incubating of said genetically modified cell; and recording changes in at least two different said cellular parameter readouts for said genetically modified cell and said basal level cell whose levels respond to said pathways as a result of introduction of said genetic agent;

deriving a biomap dataset from said changes in parameter readouts wherein said biomap comprises data normalized to be a ratio of test to control data on the same cell type under control conditions in the absence of said genetic agent, and said parameters are optimized so that the set of data in the biomap is sufficiently informative that it can discriminate the pathway influence of said agent; and analyzing said biomap by a multiparameter pattern recognition algorithm to quantify relatedness of said biomap to reference biomaps that include known genetic agents that target specific pathways, wherein the presence or absence of relatedness to said reference biomaps provides a characterization of said genetic agent in influencing said at least one pathway.

15. The method according to claim 14, wherein said genetically modified cell and said basal level cell are endothelial cells.

16. The method according to claim 14, wherein said parameters include at least two of ICAM-1, VCAM-1, Mig, IL-8, and HLA-DR.

17. The method according to claim 14, wherein said at least one pathway includes at least one of NF☐B and Jak/STAT.

18. A method for determining whether a genetic agent influences at least one pathway in a cell in a cell culture, wherein said pathway includes at least one of NF☐B and Jak/STAT, the method comprising:

expressing said genetic agent in a genetically modified cell to overproduce the product of said genetic agent as compared to a cell in the basal state, wherein said cell is present in a cell culture assay combination, wherein said cell culture assay combination comprises at least two factors sufficient to provide a physiological state of interest involving at least two pathways in said cell in said cell culture, wherein said factors include at least one of IL-1, IFN-gamma, and TNF-alpha, said pathways being indicated by levels of selected cellular parameters;

incubating said genetically modified cell in said culture for sufficient time for expression of said genetic agent and growth of said cell;

incubating said basal level cell in said culture for a time analogous to said incubating of said genetically modified cell;

recording changes in at least two different said cellular parameter readouts for said genetically modified cell and said basal level cell whose levels respond to said pathways as a result of introduction of said genetic agent;

deriving a biomap dataset from said changes in parameter readouts wherein said biomap comprises data normalized to be a ratio of test to control data on the same cell type under control conditions in the absence of said genetic agent, and said parameters are optimized so that the set of data in the biomap is sufficiently informative that it can discriminate the pathway influence of said agent; and analyzing said biomap by a multiparameter pattern recognition algorithm to quantify relatedness of said biomap to reference biomaps that include known genetic agents that target specific pathways, wherein the presence or absence of relatedness to said reference biomaps provides a characterization of said genetic agent in influencing said at least one pathway.

19. The method according to claim 18, wherein said at least one pathway is involved with the inflammatory state.

20. The method according to claim 18, wherein said parameters include at least two of ICAM-1, VCAM-1, Mig, IL-8, and HLA-DR.

21. The method according to claim 18, wherein said changes in said levels are compared to at least one BioMAP of levels of parameters for a selected state.

* * * * *